United States Patent
Armstrong et al.

(10) Patent No.: US 7,112,553 B1
(45) Date of Patent: Sep. 26, 2006

(54) PESTICIDAL INDAZOLE OR BENZOTRIAZOLE DERIVATIVES

(75) Inventors: Sarah Armstrong, Bracknell (GB); Nigel John Barnes, Bracknell (GB); Susan Patricia Barnett, Bracknell (GB); Eric Daniel Clarke, Bracknell (GB); Patrick Jelf Crowley, Bracknell (GB); Torquil Eoghan Macleod Fraser, Bracknell (GB); David John Hughes, Bracknell (GB); Christopher John Mathews, Bracknell (GB); Brian Leslie Pilkington, deceased, late of Bracknell (GB); by Joan Pilkington, legal representative, Bracknell (GB); Roger Salmon, Bracknell (GB); Stephen Christopher Smith, Bracknell (GB); Russell Viner, Bracknell (GB); William Guy Whittingham, Bracknell (GB); John Williams, Bracknell (GB); Alan John Whittle, Bracknell (GB)

(73) Assignee: Syngenta Limited, Guildford (GB)

( * ) Notice: Subject to any disclaimer, the term of this patent is extended or adjusted under 35 U.S.C. 154(b) by 0 days.

(21) Appl. No.: 09/959,269

(22) PCT Filed: Apr. 4, 2000

(86) PCT No.: PCT/GB00/01272

§ 371 (c)(1),
(2), (4) Date: Feb. 4, 2003

(87) PCT Pub. No.: WO00/63207

PCT Pub. Date: Oct. 26, 2000

(30) Foreign Application Priority Data

Apr. 20, 1999 (GB) .................. 9909062.3
Jan. 28, 2000 (GB) .................. 0002039.6

(51) Int. Cl.
*C07D 417/12* (2006.01)
*A01N 43/48* (2006.01)
*A01N 43/64* (2006.01)

(52) U.S. Cl. .................. 504/261; 504/281; 548/360.1; 548/360.5; 548/361.1

(58) Field of Classification Search .............. 504/216, 504/261, 281; 548/360.1, 360.5, 361.1
See application file for complete search history.

(56) References Cited

FOREIGN PATENT DOCUMENTS

WO    WO 95/314448    * 11/1995
WO    WO 98/17630    * 4/1998

* cited by examiner

*Primary Examiner*—Zinna N. Davis
(74) *Attorney, Agent, or Firm*—Rebecca A. Gegick

(57) ABSTRACT

A compound of formula (I) wherein G is either (i) or (ii), where $M^1$ or $M^2$ is bonded to A; n is 0 or 1; when G is (i), D is S, $NR^7$, $CR^8=CR^9$, $CR^8=N$, $CR^8=N(O)$, $N=CR^9$ or $N(O)=CR^9$; when G is (ii), D is S or $NR^7$; E is N, N-oxide or $CR^{10}$; $M^1$ is $OC(=Y)$, $N(R^{11})C(=Y)$, $N=C(OR^{12})$, $N=C(SR^{13})$ or $N=C(NR^{14}R^{15})$ where O or N is the atom of attachment to the ring containing D and E; $M^2$ is $N\!-\!C(=Y)$ where N is the atom of attachment to the ring containing D and E; Y is O, S or $NR^{16}$; J is N or $CR^{17}$; and A, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each certain organic or inorganic groups. These compounds are useful in fungicidal, insecticidal, acaricidal, molluscicidal and hematicidal compositions.

12 Claims, No Drawings

PESTICIDAL INDAZOLE OR BENZOTRIAZOLE DERIVATIVES

The present invention relates to azine and azole derivatives, to processes for preparing them, to fungicidal, insecticidal, acaricidal, molluscicidal and nematicidal compositions comprising them, to methods of using them to combat fungal diseases (especially fungal diseases of plants) and to methods of using them to combat and control insect, acarine, mollusc and nematode pests.

Azole and azine derivatives are disclosed in WO95/31448, WO97/18198, WO98/02424 and WO98/05670.

The present invention provides a compound of formula (I):

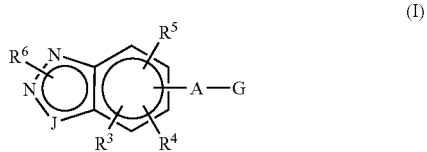

wherein G is either

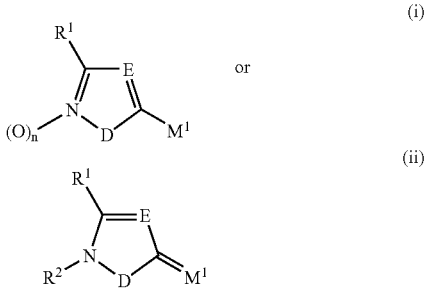

where $M^1$ or $M^2$ is bonded to A; n is 0 or 1; A is optionally substituted $C_{1-6}$ alkylene, optionally substituted $C_{2-6}$ alkenylene, optionally substituted $C_{2-6}$ alkynylene, optionally substituted $C_{1-6}$ alkylenoxy, optionally substituted oxy($C_{1-6}$)alkylene, optionally substituted $C_{1-6}$ alkylenethio, optionally substituted thio($C_{1-6}$)alkylene, optionally substituted $C_{1-6}$ alkylenamino, optionally substituted amino($C_{1-6}$)alkylene, optionally substituted [$C_{1-6}$ alkyleneoxy($C_{1-6}$)alkylene], optionally substituted [$C_{1-6}$ alkylenethio($C_{1-6}$)alkylene], optionally substituted [$C_{1-6}$ alkylenesulfinyl($C_{1-6}$)alkylene], optionally substituted [$C_{1-6}$ alkylenesulfonyl($C_{1-6}$)alkylene] or optionally substituted [$C_{1-6}$ alkyleneamino($C_{1-6}$)alkylene]; when G is (i), D is S, $NR^7$, $CR^8=CR^9$, $CR^8=N$, $CR^8=N(O)$, $N=CR^9$ or $N(O)=CR^9$; when G is (ii), D is S or $NR^7$; E is N, N-oxide or $CR^{10}$; $M^1$ is $OC(=Y)$, $N(R^{11})C(=Y)$, $N=C(OR^{12})$, $N=C(SR^{13})$ or $N=C(NR^{14}R^{15})$ where O or N is the atom of attachment to the ring containing D and E; $M^2$ is $N-C(=Y)$ where N is the atom of attachment to the ring containing D and E; Y is O, S or $NR^{16}$; J is N or $CR^{17}$; $R^1$ is hydrogen, halogen, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ alkylthio, optionally substituted $C_{3-7}$ cycloalkyl, cyano, nitro or $SF_5$; $R^2$ is optionally substituted $C_{1-10}$ alkyl, optionally substituted [$C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$) alkylaminocarbonyl, optionally substituted phenoxycarbonyl, optionally substituted $C_{1-6}$ alkylthio, optionally substituted $C_{1-6}$ alkylsulfinyl, optionally substituted $C_{1-6}$ alkylsulfonyl, optionally substituted arylthio, optionally substituted arylsulfinyl, optionally substituted arylsulfonyl or $R^{18}R^{19}NS$; $R^3$, $R^4$ and $R^5$ are, independently, hydrogen, halogen, optionally substituted $C_{1-6}$ alkyl, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, cyano, nitro, optionally substituted $C_{1-6}$ alkylcarbonyl, optionally substituted $C_{1-6}$ alkoxycarbonyl or $SF_5$; $R^6$ is hydrogen, cyano, optionally substituted $C_{1-20}$ alkyl, optionally substituted substituted $C_{2-20}$ alkenyl ($C_{1-6}$)alkyl, optionally substituted $C_{2-20}$ alkynyl($C_{1-6}$)alkyl, optionally substituted $C_{3-7}$ cycloalkyl, optionally substituted $C_{5-4}$ cycloalkenyl, formyl, optionally substituted $C_{1-20}$ alkoxycarbonyl, optionally substituted $C_{1-20}$ alkylcarbonyl, aminocarbonyl, optionally substituted $C_{1-20}$ alkylaminocarbonyl, optionally substituted di-($C_{1-20}$)alkylaminocarbonyl, optionally substituted aryloxycarbonyl, optionally substituted arylcarbonyl, optionally substituted arylaminocarbonyl, optionally substituted N-alkyl-N-arylaminocarbonyl, optionally substituted diarylaminocarbonyl, optionally substituted heteroaryloxycarbonyl, optionally substituted heteroarylcarbonyl, optionally substituted heteroarylaminocarbonyl, optionally substituted alkylheteroarylaminocarbonyl, optionally substituted diheteroarylaminocarbonyl, optionally substituted phenyl, optionally substituted heteroaryl, optionally substituted heterocyclyl, optionally substituted $C_{1-20}$ alkylsulfonyl or optionally substituted arylsulfonyl; $R^7$ is $C_{1-6}$ alkyl; $R^8$ and $R^9$ are, independently, hydrogen, halogen, cyano, nitro, optionally substituted $C_{1-6}$ alkyl, optionally substituted $C_{2-6}$ alkenyl, optionally substituted $C_{2-6}$ alkynyl or optionally substituted $C_{1-6}$ alkoxy; $R^{10}$ is hydrogen, halogen, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, cyano, nitro, formyl, $R^{20}ON=C(R^{21})$, optionally substituted $C_{1-6}$ alkylcarbonyl, optionally substituted $C_{1-6}$ alkoxycarbonyl or $SF_5$; or $R^1$ and $R^{10}$ together with the atoms to which they are attached may be joined to form a five, six or seven-membered saturated or unsaturated ring carbocylic or heterocyclic ring which may contain one or two hetero atoms selected from O, N or S and which may be optionally substituted by $C_{1-6}$ alkyl, $C_{1-6}$ haloalkyl or halogen; $R^{11}$ is hydrogen, optionally substituted $C_{1-10}$ alkyl, optionally substituted [$C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$)alkylaminocarbonyl, optionally substituted phenoxycarbonyl, optionally substituted $C_{1-6}$ alkylthio, optionally substituted $C_{1-6}$ alkylsulfinyl, optionally substituted $C_{1-6}$ alkylsulfonyl, optionally substituted arylthio, optionally substituted arylsulfinyl, optionally substituted arylsulfonyl or $R^{22}R^{23}NS$; $R^{12}$ is optionally substituted $C_{1-10}$ alkyl, optionally substituted [$C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$)alkyaminocarbonyl, amino, optionally substituted $C_{1-6}$ alkylamino, optionally substituted di($C_{1-6}$) alkylamino, optionally substituted phenoxycarbonyl, tri($C_{1-4}$)alkylsilyl, aryldi($C_{1-4}$)alkylsilyl, ($C_{1-4}$)alkyldiarylsilyl or triarylsilyl; $R^{13}$ is optionally substituted $C_{1-10}$ alkyl, optionally substituted [$C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, optionally substituted $C_{1-10}$ alkylaminocarbonyl, optionally substituted di($C_{1-10}$)alkylaminocarbonyl or optionally substituted phenoxycarbonyl); $R^{14}$ and $R^{15}$ are, independently optionally substituted $C_{1-10}$ alkyl, optionally substituted $C_{1-6}$ alkoxy, optionally substituted [$C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$)alkylaminocarbonyl, hydroxy, amino, optionally substituted $C_{1-6}$ alkylamino, optionally substituted di($C_{1-6}$)alkylamino, or optionally substituted phenoxycarbonyl; $R^{16}$ is hydrogen, cyano, nitro, optionally substituted $C_{1-6}$ alkyl, optionally substituted $C_{3-7}$ cycloalkyl, optionally substituted ($C_{2-6}$)alkenyl($C_{1-6}$)alkyl, optionally substituted ($C_{2-6}$)alkynyl($C_{1-6}$)alkyl, optionally substituted phenyl, optionally substituted heteroaryl, optionally substituted $C_{1-6}$ alkylcarbonyl, optionally substituted $C_{1-6}$ alkoxycarbonyl, optionally substituted $C_{1-6}$ alkylamino, optionally substituted di($C_{1-6}$)alkylamino, optionally substituted $C_{1-6}$ alkylcarbonylamino, optionally substituted $C_{1-6}$ alkoxycarbonylamino, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, optionally substituted arylthio, optionally substituted arylsulfinyl, optionally substituted arylsulfonyl or $C_{1-6}$ acyloxy; $R^{17}$ is hydrogen, halogen, nitro, cyano, optionally substituted $C_{1-8}$ alkyl, optionally substituted $C_{2-6}$ alkenyl, optionally substituted $C_{2-6}$ alkynyl, optionally substituted $C_{3-7}$ cycloalkyl, optionally substituted $C_{1-6}$ alkoxycarbonyl, optionally substituted $C_{1-6}$ alkylcarbonyl, optionally substituted $C_{1-6}$ alkylaminocarbonyl, optionally substituted di($C_{1-6}$)alkylaminocarbonyl, optionally substituted phenyl or optionally substituted heteroaryl; $R^{18}$ and $R^{19}$ are, independently, optionally substituted $C_{1-6}$ alkyl or $R^{18}$ and $R^{19}$ together with the N atom to which they are attached form a five, six or seven-membered heterocyclic ring which may contain one or two further hetero atoms selected from O, N or S and which may be optionally substituted by one or two $C_{1-6}$ alkyl groups; $R^{20}$ is hydrogen, optionally substituted phenyl, optionally substituted phenyl($C_{1-4}$)alkyl or optionally substituted $C_{1-20}$ alkyl; $R^{21}$ is hydrogen, optionally substituted phenyl or optionally substituted $C_{1-6}$ alkyl; and $R^{22}$ and $R^{23}$ are, independently, optionally substituted $C_{1-6}$ alkyl or $R^{22}$ and $R^{23}$ together with the N atom to which they are attached form a five, six or seven-membered heterocyclic ring which may contain one or two further hetero atoms selected from O, N or S and which may be optionally substituted by one or two $C_{1-6}$ alkyl groups.

The compounds of formula (I) may exist in different geometric or optical isomers or tautomeric forms. This invention covers all such isomers and tautomers and mixtures thereof in all proportions.

When present, optional substituents on alkylene, alkenylene or alkynylene moieties include, subject to valency constraints, one or more of halogen, $C_{1-6}$ alkyl, $C_{1-6}$ haloalkyl, $C_{1-6}$ cyanoalkyl, $C_{1-6}$ alkoxy($C_{1-6}$) alkyl, $C_{1-6}$ alkoxy, cyano, $=O$, $=NR^{24}$ and $=CR^{25}R^{26}$, wherein $R^{24}$ is $C_{1-6}$ alkyl, $C_{1-6}$ haloalkyl, $OR^{27}$ or $R^{28}R^{29}N$; where $R^{25}$ and $R^{26}$ are, independently, hydrogen, $C_{1-6}$ alkyl, $C_{1-6}$alkoxy, $C_{1-6}$ haloalkyl, cyano, $C_{1-6}$ alkoxycarbonyl, $C_{1-6}$ alkylcarbonyl or $R^{30}R^{31}N$; $R^{27}$ is $C_{1-6}$ alkyl, $C_{3-7}$ haloalkyl or phenyl ($C_{1-2}$)alkyl; $R^{28}$ and $R^{29}$ are, independently, hydrogen, $C_{1-8}$ alkyl, $C_{3-7}$ cycloalkyl, $C_{2-6}$ alkenyl($C_{1-6}$)alkyl, $C_{2-6}$ alkynyl ($C_{1-6}$)alkyl, $C_{2-6}$ haloalkyl, $C_{1-6}$ alkoxy($C_{1-6}$)alkyl, $C_{1-6}$ alkoxycarbonyl($C_{1-4}$)alkyl, carboxy($C_{1-6}$)alkyl or phenyl ($C_{1-2}$)alkyl or $R^{28}$ and $R^{29}$ together with the N atom to which they are attached form a five, six or seven-membered heterocyclic ring which may contain one or two further hetero atoms selected from O, N or S and which may be optionally substituted by one or two $C_{1-6}$ alkyl groups; $R^{30}$ and $R^{31}$ are, independently, hydrogen, $C_{1-8}$ alkyl, $C_{3-7}$ cycloalkyl, $C_{2-6}$ alkenyl($C_{1-6}$)alkyl, $C_{2-6}$ alkynyl($C_{1-6}$)alkyl, $C_{2-6}$ haloalkyl, $C_{1-6}$ alkoxy-($C_{1-6}$)alkyl, $C_{1-6}$ alkoxycarbonyl ($C_{1-6}$)alkyl, carboxy($C_{1-6}$)alkyl or phenyl($C_{1-2}$)alkyl; or $R^{30}$ and $R^{31}$ together with the N atom to which they are attached form a five, six or seven-membered heterocyclic ring which may contain one or two further hetero atoms selected from O, N or S and which may be optionally substituted by one or two $C_{1-6}$ alkyl groups.

Each alkyl moiety is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. When present, the optional substituents on alkyl include one or more of halogen, nitro, cyano, $HO_2C$, $C_{1-10}$ alkoxy (itself optionally substituted by $C_{1-10}$ alkoxy), aryl-($C_{1-4}$)alkoxy, $C_{1-10}$ alkylthio, $C_{1-10}$ alkylcarbonyl, $C_{1-10}$ alkoxycarbonyl, $C_{1-6}$ alkylaminocarbonyl, di($C_{1-6}$ alkyl) aminocarbonyl, ($C_{1-6}$)alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$)alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri($C_{1-4}$)alkylsilyl, tri($C_{1-4}$)alkylsilyl-($C_{1-6}$) alkoxy, aryldi($C_{1-4}$)alkylsilyl, ($C_{1-4}$)alkyldiarylsilyl, triarylsilyl, $=N-OR'$ and $=N-NR'R''$; where R' and R'' are, independently, $C_{1-6}$ alkyl or $C_{1-6}$ haloalkyl.

Alkenyl and alkynyl moieties can be in the form of straight or branched chains, and the alkenyl moieties, where appropriate, can be of either the (E)- or (Z)-configuration. Examples are vinyl, allyl and propargyl. When present, the optional substituents on alkenyl or alkynyl include one or more of halogen, aryl and $C_{3-7}$ cycloalkyl.

In the context of this specification acyl is optionally substituted $C_{1-6}$ alkylcarbonyl (for example acetyl), optionally substituted $C_{2-6}$ alkenylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are optionally substituted with one or more of the same or different halogen atoms and are, for example, $CF_3$, $CF_2Cl$, $CF_3CH_2$ or $CHF_2CH_2$.

Aryl includes naphthyl, anthracyl, fluorenyl and indenyl but is preferably phenyl.

The term heteroaryl refers to an aromatic ring containing up to 10 atoms including one or more heteroatoms (preferably one or two heteroatoms) selected from O, S and N. Examples of such rings include pyridine, pyrimidine, furan, quinoline, quinazoline, pyrazole, thiophene, thiazole, oxazole and isoxazole.

The terms heterocycle and heterocyclyl refers to a non-aromatic ring containing up to 10 atoms including one or more (preferably one or two) heteroatoms selected from O, S and N. Examples of such rings include 1,3-dioxolane, tetrahydrofuran and morpholine. It is preferred that heterocyclyl is optionally substituted by $C_{1-6}$ alkyl.

Cycloalkyl includes cyclopropyl, cyclopentyl and cyclohexyl. The optional substituents for cycloalkyl include halogen, cyano and $C_{1-3}$ alkyl.

Cycloalkenyl includes cyclopentenyl and cyclohexenyl. The optional substituents for cycloalkenyl include $C_{1-3}$ alkyl, halogen and cyano.

Carbocyclic rings include aryl, cycloalkyl and cycloalkenyl groups.

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy$(C_{1-6})$alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R^{32}R^{33}N$ or $R^{34}R^{35}NC(O)$ wherein $R^{32}$, $R^{33}$, $R^{34}$ and $R^{35}$ are, independently, hydrogen or $C_{1-6}$ alkyl.

It is to be understood that dialkylamino substituents include those where the dialkyl groups together with the N atom to which they are attached form a five, six or seven-membered heterocyclic ring which may contain one or two further hetero atoms selected from O, N or S and which may be optionally substituted by one or two $C_{1-6}$ alkyl groups. When heterocyclic rings are formed by joining two groups on an N atom, the resulting rings are suitably pyrrolidine, piperidine, thiomorpholine and morpholine each of which may be substituted by one or two $(C_{1-6})$alkyl groups.

In a further aspect, the present invention provides a compound of formula (IA):

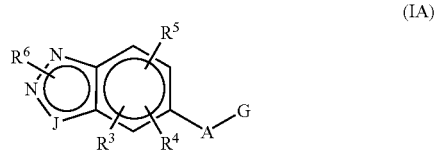

(IA)

wherein A, G, J, $R^3$, $R^4$, $R^5$ and $R^6$ are as defined above for a compound of formula (I).

More preferred compounds of formula (IA) are those wherein n is 0; A is $C_{1-6}$ alkylene, $C_{1-6}$ alkenylene, $C_{1-6}$ alkylenoxy, oxy$(C_{1-6})$alkylene, $C_{1-6}$ alkylenamino or $C_{1-6}$ alkylenethio, each of which is optionally substituted by $C_{1-3}$ alkyl, $C_{1-3}$ haloalkyl, $C_{1-3}$ cyanoalkyl, halogen, $C_{1-3}$ alkoxy, $C_{1-6}$ alkoxycarbonyl, cyano, =O, =$NR^{36}$ or =$CR^{37}R^{38}$; when G is (i), D is S, $NR^7$, $CR^8$=$CR^9$, $CR^8$=N, $CR^8$=N(O), N=$CR^9$ or N(O)=$CR^9$; when G is (ii), D is S or $NR^7$; E is N or $CR^{10}$; $M^1$ is $N(R^{11})C$(=Y) or N=C($SR^{13}$) where O or N is the atom of attachment to the ring containing D and E; $M^2$ is N—C(=Y) where N is the atom of attachment to the ring containing D and E; Y is O, S or $NR^{16}$; J is N or $CR^{17}$; $R^1$ is hydrogen, halogen, $C_{1-6}$ alkyl, $C_{2-6}$ alkenyl, $C_{2-6}$ alkynyl, $C_{1-6}$ cyanoalkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{3-6}$ cycloalkyl, $C_{3-7}$ cycloalkyl$(C_{1-4})$alkyl, $C_{1-6}$ alkoxy$(C_{1-6})$alkyl, cyano, nitro or $SF_5$; $R^2$ is $C_{1-10}$ alkyl, benzyloxymethyl, benzoyloxymethyl, $C_{1-6}$alkoxy$(C_{1-6})$alkyl, $C_{2-6}$ alkenyl$(C_{1-6})$alkyl, $C_{2-6}$ alkynyl$(C_{1-6})$alkyl, $C_{1-10}$ alkylcarbonyl or $C_{1-10}$ alkoxycarbonyl; $R^3$, $R^4$ and $R^5$ are, independently, selected from hydrogen, halogen, $C_{1-6}$ alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{1-6}$ haloalkyl, cyano, nitro, $C_{1-6}$ alkylcarbonyl, $C_{1-6}$ alkoxycarbonyl or $SF_5$; $R^6$ is $C_{1-10}$ alkyl or $C_{1-10}$ haloalkyl (each one of which may be substituted with a $C_{1-6}$ alkyloxime, $C_{1-6}$ haloalkyloxime, $C_{1-6}$ alkylhydrazone or $C_{1-6}$ haloalkylhydrazone group) or cyano, $C_{1-6}$ cyanoalkyl, $C_{2-6}$ alkenyl$(C_{1-6})$alkyl, $C_{2-6}$ alkynyl$(C_{1-6})$alkyl, $C_{3-7}$ cycloalkyl, $C_{3-7}$ halocycloalkyl, $C_{3-7}$ cyanocycloalkyl, $C_{1-3}$ alkyl$(C_{3-7})$cycloalkyl, $C_{1-3}$ alkyl$(C_{3-7})$halocycloalkyl, $C_{5-6}$ cycloalkenyl, $C_{3-7}$ cycloalkyl$(C_{1-6})$alkyl, $C_{5-6}$ cycloalkenyl$(C_{1-6})$alkyl, $C_{2-6}$ haloalkenyl $(C_{1-6})$alkyl, $C_{1-6}$ cyanoalkenyl$(C_{1-6})$alkyl, $C_{1-6}$ alkoxy$(C_{1-6})$alkyl, $C_{3-6}$ alkenyloxy$(C_{1-6})$alkyl, $C_{3-6}$ alkynyloxy$(C_{1-6})$alkyl, aryloxy $(C_{1-6})$alkyl, formyl, $C_{1-6}$ carboxyalkyl, $C_{1-6}$ alkylcarbonyl-$(C_{1-6})$alkyl, $C_{2-6}$ alkenylcarbonyl$(C_{1-6})$alkyl, $C_{2-6}$ alkynylcarbonyl$(C_{1-6}$ alkyl, $C_{1-6}$ alkoxycarbonyl$(C_{1-6})$alkyl, $C_{3-6}$ alkenyloxycarbonyl$(C_{1-6})$alkyl, $C_{3-6}$ alkynyloxycarbonyl-$(C_{1-6})$alkyl, aryloxycarbonyl$(C_{1-6})$alkyl, $C_{1-6}$ alkylthio$(C_{1-6})$ alkyl, $C_{1-6}$ alkylsulfinyl$(C_{1-6})$alkyl, $C_{1-6}$ alkylsulfonyl$(C_{1-6})$ alkyl, aminocarbonyl$(C_{1-6})$alkyl, aminocarbonyl$(C_{2-6})$ alkenyl, aminocarbonyl$(C_{2-6})$alkynyl, $C_{1-6}$ alkylaminocarbonyl$(C_{1-6})$alkyl, di$(C_{1-6})$alkylaminocarbonyl $(C_{1-6})$alkyl, $C_{1-6}$ alkylaminocarbonyl$(C_{2-6})$alkenyl$(C_{1-6})$ alkyl, di$(C_{1-6})$alkylaminocarbonyl$(C_{2-6})$alkenyl$(C_{1-6})$alkyl, alkylaminocarbonyl$(C_{2-6})$alkynyl$(C_{1-6})$alkyl, di-$(C_{1-6})$alkylaminocarbonyl$(C_{1-6})$alkynyl$(C_{1-6})$alkyl, $C_{1-6}$ alkoxycarbonyl, $C_{1-6}$ alkylcarbonyl, aminocarbonyl, $C_{1-6}$ alkylaminocarbonyl, di$(C_{1-6})$alkylaminocarbonyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy), phenyl$(C_{1-4})$alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), phenyl$(C_{2-4})$alkenyl$(C_{1-6})$alkyl, (wherein the phenyl group is optionally substituted by halo, nitro, cyano, $C_{1-6}$ alkyl, $C_{1-6}$ haloalkyl, $C_{1-6}$ alkoxy, $C_{1-6}$ alkylsulfonyl or $C_{1-6}$ haloalkoxy), heteroaryl (optionally substituted by halo, nitro, cyano, $C_{1-6}$ alkyl, $C_{1-6}$ haloalkyl, $C_{1-6}$ alkoxy, $C_{1-6}$ alkylsulfonyl or $C_{1-6}$ haloalkoxy), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl$(C_{1-4})$alkyl (where the heteroaryl may be substituted by halo, nitro, cyano, $C_{1-6}$ alkyl, $C_{1-6}$ haloalkyl, $C_{1-6}$ alkoxy or $C_{1-6}$ haloalkoxy), or heterocyclyl$(C_{1-4})$alkyl (where the heterocyclyl may be substituted by halo, cyano, $C_{1-6}$ alkyl, $C_{1-6}$ haloalkyl, $C_{1-6}$ alkoxy or $C_{1-6}$ haloalkoxy); $R^7$ is $C_{1-6}$ alkyl; $R^8$ and $R^9$ independently are, hydrogen, halogen, $C_{1-6}$ alkyl, $C_{1-6}$ haloalkyl $C_{2-6}$ alkenyl, $C_{1-6}$ alkynyl, $C_{1-6}$ alkoxy or $C_{1-6}$ haloalkoxy; $R^{10}$ is hydrogen, halogen, $C_{1-6}$ alkyl, $C_{2-6}$ alkenyl, $C_{1-6}$ alkynyl, $C_{1-6}$ haloalkyl, $C_{1-6}$ alkoxy, $C_{1-6}$ alkoxy $(C_{1-6})$alkyl, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{1-6}$ haloalkyl, cyano, nitro, formyl, $R^{20}ON$=CH, $C_{1-6}$ alkylcarbonyl, $C_{1-6}$ alkoxycarbonyl or $SF_5$; or together $R^1$ and $R^{10}$ together with the atoms to which they are attached may be joined to form a five, six or seven-membered saturated or unsaturated ring carbocyclic or heterocyclic ring which may contain one or two hetero atoms selected from O, N or S and which may be optionally substituted by $C_{1-6}$ alkyl, $C_{1-6}$ haloalkyl or halogen; $R^{11}$ is hydrogen, $C_{1-10}$ alkyl, benzyloxymethyl, benzoyloxymethyl, $C_{1-6}$alkoxy$(C_{1-6})$alkyl, $C_{2-6}$ alkenyl$(C_{1-6})$ alkyl (especially allyl), $C_{2-6}$ alkynyl$(C_{1-6})$alkyl (especially propargyl), $C_{1-10}$ alkylcarbonyl or $C_{1-10}$ alkoxycarbonyl (especially isobutoxycarbonyl); $R^{13}$ is $C_{1-10}$ alkyl, benzyloxymethyl, benzoyloxymethyl, $C_{1-6}$alkoxy$(C_{1-6})$alkyl, $C_{2-6}$ alkenyl$(C_{1-6})$alkyl (especially allyl), $C_{2-6}$ alkynyl$(C_{1-6})$alkyl (especially propargyl), $C_{1-10}$ alkylcarbonyl or $C_{1-10}$ alkoxycarbonyl (especially isobutoxycarbonyl); $R^{16}$ is cyano, nitro, $C_{1-6}$ alkyl, $C_{1-6}$ haloalkyl, $C_{3-7}$ cycloalkyl, $C_{3-7}$ cycloalkyl($C_{1-6}$)alkyl, $CH_2(C_{2-6})$alkenyl, $CH_2(C_{2-6})$alkynyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy) heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylcarbonyl, $C_{1-6}$ alkoxycarbonyl, $C_{1-6}$ alkylamino, di($C_{1-6}$)alkylamino, $C_{1-6}$ alkylcarbonylamino, $C_{1-6}$ alkoxycarbonylamino, $C_{1-6}$ alkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, arylthio, arylsulfinyl, arylsulfonyl or $(C_{1-6})$alkylC(O)O; $R^{17}$ is hydrogen, halogen, nitro, cyano, $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{2-6}$ haloalkenyl, $C_{3-7}$ cycloalkyl($C_{1-6}$)alkyl, $C_{1-6}$alkox($C_{1-6}$)alkyl, $C_{1-6}$ alkoxycarbonyl, $C_{1-6}$ alkylcarbonyl, $C_{1-6}$ alkylaminocarbonyl, di($C_{1-6}$alkylaminocarbonyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy) or heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy); $R^{20}$ is $C_{1-6}$ alkyl or phenyl($C_{1-2}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy); $R^{36}$ is $C_{1-6}$ alkyl, $OR^{39}$ or $NR^{40}R^{41}$; $R^{37}$ is hydrogen, $C_{1-6}$ alkyl or $C_{1-6}$ haloalkyl; $R^{38}$ is hydrogen, $C_{1-6}$ alkyl, $C_{1-6}$ haloalkyl, $C_{1-6}$ alkoxy, cyano, $C_{1-6}$ alkoxycarbonyl, $C_{1-6}$ alkylcarbonyl or $NR^{42}R^{43}$; $R^{39}$ is $C_{1-6}$ alkyl or optionally substituted phenyl($C_{1-2}$)alkyl; $R^{40}$ and $R^{41}$ independently are, hydrogen, $C_{1-8}$ alkyl or phenyl (optionally substituted by halo, nitro, cyano, $C_{1-6}$ alkyl, $C_{1-6}$ haloalkyl, $C_{1-6}$ alkoxy or $C_{1-6}$ haloalkoxy); and $R^{42}$ and $R^{43}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxy($C_{1-6}$)alkyl, $C_{1-6}$ alkoxycarbonyl($C_{1-6}$)alkyl, carboxy($C_{1-6}$)alkyl or phenyl($C_{1-2}$)alkyl; or $R^{42}$ and $R^{43}$ together with the N atom to which they are attached form a five, six or seven-membered heterocyclic ring which may contain one or two further hetero atoms selected from O, N or S and which may be optionally substituted by one or two $C_{1-6}$ alkyl groups.

Preferably n is 0.

Preferably A is $C_{1-4}$ alkylene, —C(O)— or $C_{1-4}$ alkyleneoxy.

When G is (i), D is preferably S or $CR^8$=$CR^9$, where $R^8$ and $R^9$ are, independently, hydrogen, halogen, $C_{1-6}$ alkyl, $C_{1-6}$ haloalkyl $C_{2-6}$ alkenyl, $C_{1-6}$ alkynyl, $C_{1-6}$ alkoxy or $C_{1-6}$ haloalkoxy.

When G is (ii), D is preferably S.

Preferably E is N or $CR^{10}$ where $R^{10}$ is hydrogen, halogen, $C_{1-6}$ alkyl, $C_{1-6}$ haloalkyl, $C_{1-6}$ alkoxy, $C_{1-6}$ haloalkoxy, $C_{1-6}$ alkoxy ($C_{1-6}$)alkyl, $C_{1-6}$ alkylthio or $SF_5$; or $R^1$ and $R^{10}$ together with the atoms to which they are attached form a benzene ring optionally substituted by $C_{1-6}$ alkyl, $C_{1-6}$ haloalkyl or halogen.

Preferably G is (i).

Preferably $M^1$ is $N(R^{11})C(=O)$ where $R^{11}$ is hydrogen, $C_{1-6}$ alkyl, $C_{1-6}$ alkoxy-($C_{1-6}$)alkyl, benzyloxymethyl or benzoyloxymethyl.

Preferably Y is O.

Preferably J is N or $CR^{17}$ where $R^{17}$ is hydrogen, $C_{1-6}$ alkyl, $C_{1-6}$ haloalkyl, cyano, halogen or nitro.

$R^1$ is preferably hydrogen, halogen, $C_{1-6}$ alkyl, $C_{2-6}$ alkenyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{3-6}$ cycloalkyl, cyano, nitro or $SF_5$.

$R^2$ is preferably $C_{1-10}$ alkyl, $C_{1-6}$ alkoxy($C_{1-6}$)alkyl, allyl or propargyl.

Preferably $R^3$, $R^4$ and $R^5$ are, independently, hydrogen, $C_{1-3}$ alkyl or halogen.

$R^6$ is preferably $C_{1-10}$ alkyl or $C_{1-10}$ haloalkyl (each one of which may be substituted with a $C_{1-6}$ alkyloxime, $C_{1-6}$ haloalkyloxime, $C_{1-6}$ alkylhydrazone or $C_{1-6}$ haloalkylhydrazone group) or $C_{1-6}$ cyanoalkyl, $C_{2-6}$ alkenyl($C_{1-6}$)alkyl, $C_{2-6}$ alkynyl($C_{1-6}$)alkyl, $C_{3-7}$ cycloalkyl, $C_{3-7}$ halocycloalkyl, $C_{3-7}$ cyanocycloalkyl, $C_{1-3}$ alkyl($C_{3-7}$)cycloalkyl, $C_{1-3}$ alkyl($C_{3-7}$)halocycloalkyl, $C_{5-6}$ cycloalkenyl, $C_{3-7}$ cycloalkyl($C_{1-6}$)alkyl, $C_{5-6}$ cycloalkenyl($C_{1-6}$)alkyl, $C_{2-6}$ haloalkenyl-($C_{1-6}$)alkyl, $C_{1-6}$ cyanoalkenyl($C_{1-6}$)alkyl, $C_{1-6}$ alkoxy($C_{1-6}$)alkyl, $C_{3-6}$ alkenyloxy($C_{1-6}$)alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)alkyl, $C_{1-6}$ alkoxycarbonyl($C_{1-6}$)alkyl, $C_{3-6}$ alkenyloxycarbonyl($C_{1-6}$)alkyl, $C_{3-6}$ alkynyloxycarbonyl($C_{1-6}$)alkyl, aryloxycarbonyl-($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, aminocarbonyl($C_{2-6}$)alkenyl, aminocarbonyl($C_{2-6}$)alkynyl, $C_{1-6}$ alkylaminocarbonyl($C_{1-6}$)alkyl, di($C_{1-6}$)alkylaminocarbonyl ($C_{1-6}$)alkyl, $C_{1-6}$ alkylaminocarbonyl($C_{1-6}$)alkenyl($C_{1-6}$)alkyl, di($C_{1-6}$)alkylaminocarbonyl($C_{1-6}$)alkenyl($C_{1-6}$)alkyl, alkylaminocarbonyl($C_{1-6}$)alkynyl($C_{1-6}$)alkyl, di($C_{1-6}$)alkylaminocarbonyl($C_{1-6}$)alkynyl-($C_{1-6}$)alkyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy), phenyl($C_{1-4}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), phenyl($C_{2-4}$)alkenyl($C_{1-6}$)alkyl, (wherein the phenyl group is optionally substituted by halo, nitro, cyano, $C_{1-6}$ alkyl, $C_{1-6}$ haloalkyl, $C_{1-6}$ alkoxy, $C_{1-6}$ alkylsulfonyl or $C_{1-6}$ haloalkoxy), heteroaryl (optionally substituted by halo, nitro, cyano, $C_{1-6}$ alkyl, $C_{1-6}$ haloalkyl, $C_{1-6}$ alkoxy or $C_{1-4}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl-($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy, $C_{1-6}$ alkylsulfonyl or $C_{1-6}$ haloalkoxy)or heterocyclyl-($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy).

Preferably the optionally substituted ring of formula

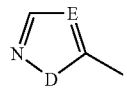

is optionally substituted isothiazolyl, optionally substituted pyridyl, optionally substituted pyrimidinyl, optionally substituted quinazolinyl and optionally substituted quinolinyl groups in which the optional substituents are chosen from halo, $C_{1-6}$ alkyl, $C_{1-6}$ haloalkyl, $C_{1-6}$ alkoxy, $C_{1-6}$ alkoxy($C_{1-6}$)alkyl or $C_{1-6}$ haloalkoxy.

Preferably the optionally substituted ring of formula

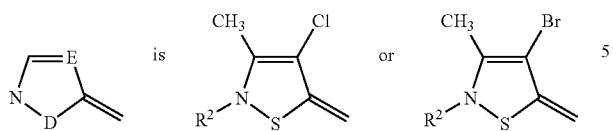

More preferably A is $CH_2$ or $CH_2O$, even more preferably $CH_2$.

More preferably $M^1$ is $N(R^{11})C(=O)$, where $R^{11}$ is hydrogen, $C_{1-4}$ alkyl, $C_{1-4}$ alkoxy-$(C_{1-4})$alkyl, benzyloxymethyl or benzoyloxymethyl. It is especially preferred that $R^{11}$ is hydrogen, ethyl, ethoxymethyl, allyl or propargyl.

More preferably J is N or $CR^{17}$, where $R^{17}$ is hydrogen, methyl or halogen.

More preferably $R^2$ is ethyl, ethoxymethyl, allyl or propargyl.

More preferably $R^3$, $R^4$ and $R^5$ are independently, hydrogen, or halogen (especially fluorine); it is especially preferred that each of $R^3$, $R^4$ and $R^5$ is hydrogen.

More preferably $R^6$ is $C_{1-8}$ alkyl, $C_{2-8}$ haloalkyl, $C_{1-8}$ cyanoalkyl, $C_{3-7}$ cycloalkyl, $C_{1-3}$ alkyl $(C_{3-7})$ cycloalkyl, $C_{1-6}$ alkoxy $(C_{1-6})$ alkyl, heterocyclic (optionally substituted by halo, nitro, cyano, $C_{1-6}$ alkyl, $C_{1-6}$ haloalkyl, $C_{1-6}$ alkoxy or $C_{1-6}$ haloalkoxy), phenyl (optionally substituted by halogen, $C_{1-6}$ alkyl, $C_{1-6}$ haloalkyl, $C_{1-6}$ alkoxy, nitro, cyano or $C_{1-6}$ alkylsulfonyl) or heteroaryl (optionally substituted by halogen, $C_{1-6}$ alkyl, $C_{1-6}$ haloalkyl, $C_{1-6}$ alkoxy, nitro, cyano or $C_{1-6}$ alkylsulfonyl).

Even more preferably $R^6$ is $C_{1-8}$ alkyl, $C_{2-6}$ haloalkyl, $C_{1-6}$alkoxy$(C_{1-6})$alkyl, $C_{3-7}$cycloalkyl or $C_{3-7}$ cycloalkyl $(C_{1-6})$alkyl.

Even more preferably the group

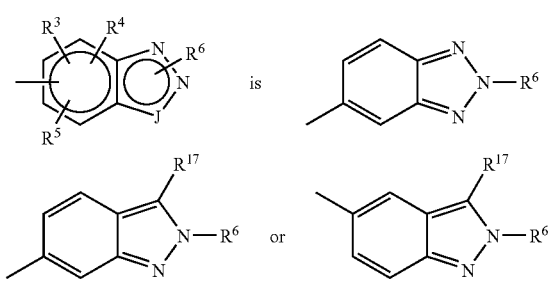

Most preferably the optionally substituted ring of formula

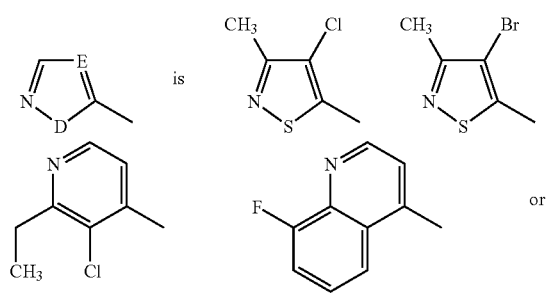

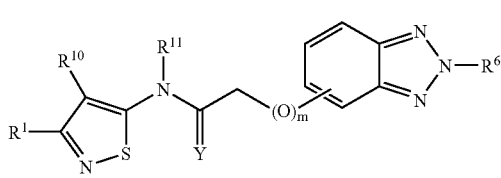

In a further aspect the present invention provides a compound of formula (IB):

(IB)

wherein $R^1$ is hydrogen, halogen, $C_{1-6}$ alkyl, $C_{1-6}$ haloalkyl, $C_{1-6}$ alkoxy, $C_{1-6}$ haloalkoxy, $C_{1-6}$ alkylthio, $C_{3-6}$ cycloalkyl or $C_{1-6}$ alkoxy$(C_{1-6})$alkyl; $R^{10}$ is hydrogen, halogen, $C_{1-6}$ alkyl, $C_{1-6}$ haloalkyl, cyano, nitro, CHO, CH=$NOR^{20}$, $C_{1-6}$ alkylcarbonyl, $C_{1-6}$ alkoxycarbonyl or $C_{1-6}$ alkylS(O)$_q$; or together $R^1$ and $R^{10}$ form a five or six membered saturated or unsaturated carbocyclic ring, optionally substituted by one or two $C_{1-6}$ alkyl groups; $R^{11}$ is hydrogen, $C_{1-6}$ alkyl, $CH_2(C_{1-4}$ haloalkyl), $C_{3-6}$ alkenyl, $C_{3-6}$ alkynyl, $C_{1-6}$ alkoxy $(C_{1-6})$alkyl, $C_{1-6}$ alkylcarbonyl, $C_{1-6}$ alkoxycarbonyl, formyl, optionally substituted phenoxycarbonyl, optionally substituted phenyl$(C_{1-4})$alkyl or $S(O)_pR^{44}$; $R^6$ is hydrogen, $C_{1-8}$ alkyl, $C_{1-6}$ haloalkyl, $C_{1-6}$ cyanoalkyl, $C_{3-6}$ alkenyl, $C_{3-6}$ alkynyl, $C_{3-7}$ cycloalkyl, $C_{3-6}$ cycloalkyl$(C_{1-6})$alkyl, $C_{3-6}$ haloalkenyl, $C_{1-6}$ alkoxy$(C_{1-6})$alkyl, $C_{1-6}$ carboxyalkyl, $C_{1-6}$ alkylcarbonyl$(C_{1-6})$alkyl, $C_{1-6}$ alkoxycarbonyl$(C_{1-6})$alkyl, $C_{1-6}$ alkylthio$(C_{1-6})$alkyl, $C_{1-6}$ alkylsulfinyl$(C_{1-6})$alkyl, $C_{1-6}$ alkylsulfonyl$(C_{1-6})$alkyl, aminocarbonyl$(C_{1-6})$alkyl, $C_{1-6}$ alkylaminocarbonyl$(C_{1-6})$alkyl, di-$(C_{1-6})$alkylaminocarbonyl$(C_{1-6})$alkyl, optionally substituted phenyl, optionally substituted phenyl$(C_{1-4})$alkyl or optionally substituted heteroaryl; $R^{20}$ is hydrogen, $C_{1-6}$ alkyl, optionally substituted phenyl or optionally substituted phenyl$(C_{1-4})$alkyl; $R^{44}$ is $C_{1-6}$ alkyl, $C_{1-6}$ haloalkyl or optionally substituted phenyl; Y is O or S; m is 0 or 1; and p and q are, independently, 0, 1 or 2; provided that when $R^6$ is $C_{3-6}$ alkenyl, $C_{3-6}$ alkynyl or $C_{3-6}$ haloalkenyl, $R^6$ does not have an unsaturated carbon atom attached directly to N and provided that when $R^{11}$ is $C_{3-6}$ alkenyl or $C_{3-6}$ alkynyl, $R^{11}$ does not have an unsaturated carbon atom attached directly to N.

It is preferred that $R^1$ is ethyl or, especially, methyl.

It is preferred that $R^{10}$ is hydrogen, halogen (especially chloro) or cyano.

It is preferred that m is 0.

It is preferred that the compounds of the invention are of formula (Ia).

In one particular aspect the present invention provides a compound of formula (Ia) wherein $R^1$ is $C_{1-4}$ alkyl (especially methyl or ethyl); $R^{10}$ is hydrogen, halogen (especially chloro or bromo) or cyano; or $R^1$ and $R^{10}$ together form a cyclopentyl, cyclohexyl or phenyl ring; $R^{11}$ is hydrogen, $C_{1-4}$ alkyl (especially methyl or ethyl), phenyl$(C_{1-4})$alkyl (especially benzyl), $C_{1-4}$ alkylcarbonyl (especially acetyl) or $C_{1-4}$ alkylsulfonyl (especially methanesulfonyl); m is 0; Y is oxygen; and $R^6$ is $C_{1-6}$ alkyl [optionally substituted with halogen, $C_{1-4}$ alkoxy, phenyl (itself optionally substituted with halogen), $CO_2H$, $CONH_2$ (itself optionally substituted with $C_{1-4}$ alkyl), cyano, $C_{3-6}$ cycloalkyl or $CO(C_{1-4}$ alkoxy)], $C_{3-6}$ alkenyl, $C_{3-6}$ alkynyl, $C_{3-6}$ cycloalkyl, phenyl [optionally substituted with halogen, $C_{1-4}$ haloalkyl (especially $CF_3$), nitro, $CO_2H$, or cyano] or heteroaryl (especially pyridyl or pyrimidinyl) [optionally substituted with $C_{1-4}$ alkyl or $C_{1-4}$ haloalkyl].

In a further aspect the present invention provides a compound of formula (IC):

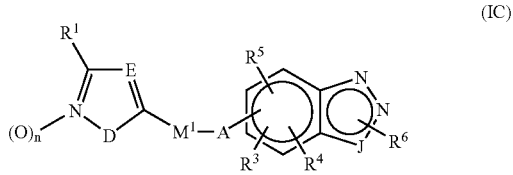

(IC)

wherein n is 0 or 1; A is optionally substituted $C_{1-6}$ alkylene, optionally substituted $C_{2-6}$ alkenylene, optionally substituted $C_{2-6}$ alkynylene, optionally substituted $C_{1-6}$ alkylenoxy, optionally substituted oxy($C_{1-6}$)alkylene, optionally substituted $C_{1-6}$ alkylenethio, optionally substituted thio($C_{1-6}$)alkylene, optionally substituted $C_{1-6}$ alkylenamino, optionally substituted amino($C_{1-6}$)alkylene, optionally substituted [$C_{1-6}$ alkyleneoxy($C_{1-6}$)alkylene], optionally substituted [$C_{1-6}$ alkylenethio($C_{1-6}$)alkylene], optionally substituted [$C_{1-6}$ alkylenesulfinyl-($C_{1-6}$)alkylene], optionally substituted [$C_{1-6}$ alkylenesulfonyl($C_{1-6}$)alkylene] or optionally substituted [$C_{1-6}$ alkyleneamino($C_{1-6}$)alkylene]; D is S, $NR^7$, $CR^8=CR^9$, $CR^8=N$, $CR^8=N(O)$, $N=CR^9$ or $N(O)=CR^9$; $R^7$ is $C_{1-6}$ alkyl; E is N, N-oxide or $CR^{10}$; $M^1$ is $OC(=Y)$, $N(R^{11})C(=Y)$, $N=C(OR^{12})$, $N=C(SR^{13})$ or $N=C(NR^{14}R^{15})$ where O or N is the atom of attachment to the ring containing E and D; Y is O, S or $NR^{16}$; J is N or $CR^{17}$; $R^1$ is hydrogen, halogen, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ alkylthio, optionally substituted $C_{3-7}$ cycloalkyl, cyano, nitro or $SF_5$; $R^{11}$ is hydrogen, optionally substituted $C_{1-10}$ alkyl, optionally substituted [$C_{2-6}$ alkenyl($C_{1-6}$)alkyl], optionally substituted [$C_{2-6}$ alkynyl-($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$)alkylaminocarbonyl, optionally substituted phenoxycarbonyl, optionally substituted $C_{1-6}$ alkylthio, optionally substituted $C_{1-6}$ alkylsulfinyl, optionally substituted $C_{1-6}$ alkylsulfonyl, optionally substituted $C_{1-6}$ arylthio, optionally substituted $C_{1-6}$ arylsulfinyl, optionally substituted $C_{1-6}$ arylsulfonyl or $R^{22}R^{23}NS$; $R^{12}$ is optionally substituted $C_{1-10}$ alkyl, optionally substituted [$C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$)alkylaminocarbonyl, amino, optionally substituted $C_{1-6}$ alkylamino, optionally substituted di-($C_{1-6}$) alkylamino, optionally substituted phenoxycarbonyl, tri($C_{1-4}$)alkylsilyl, aryldi-($C_{1-4}$)alkylsilyl, ($C_{1-4}$)alkyldiarylsilyl or triarylsilyl; $R^{13}$ is optionally substituted $C_{1-10}$ alkyl, optionally substituted [$C_{2-6}$ alkenyl($C_{1-6}$)alkyl], optionally substituted [$C_{2-6}$ alkynyl-($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, optionally substituted $C_{1-10}$ alkylaminocarbonyl, optionally substituted di($C_{1-10}$)alkylaminocarbonyl or optionally substituted phenoxycarbonyl); $R^{14}$ and $R^{15}$ are, independently optionally substituted $C_{1-10}$ alkyl, optionally substituted $C_{1-6}$ alkoxy, optionally substituted [$C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$)alkylaminocarbonyl, hydroxy, amino, optionally substituted $C_{1-6}$ alkylamino, optionally substituted di($C_{1-6}$)alkylamino, or optionally substituted phenoxycarbonyl; $R^3$, $R^4$ and $R^5$ are, independently, hydrogen, halogen, optionally substituted $C_{1-6}$ alkyl, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, cyano, nitro, optionally substituted $C_{1-6}$ alkylcarbonyl, optionally substituted $C_{1-6}$ alkoxycarbonyl or $SF_5$; $R^6$ is hydrogen, cyano, optionally substituted $C_{1-20}$ alkyl, optionally substituted $C_{2-20}$ alkenyl($C_{1-6}$)alkyl, optionally substituted $C_{2-20}$ alkynyl($C_{1-6}$)alkyl, optionally substituted $C_{3-7}$ cycloalkyl, optionally substituted $C_{5-6}$ cycloalkenyl, formyl, optionally substituted $C_{1-20}$ alkoxycarbonyl, optionally substituted $C_{1-20}$ alkylcarbonyl, aminocarbonyl, optionally substituted $C_{1-20}$ alkylaminocarbonyl, optionally substituted di($C_{1-20}$)alkylaminocarbonyl, optionally substituted aryloxycarbonyl, optionally substituted arylcarbonyl, optionally substituted arylaminocarbonyl, optionally substituted N-alkyl-N-arylaminocarbonyl, optionally substituted diarylaminocarbonyl, optionally substituted heteroaryloxycarbonyl, optionally substituted heteroarylcarbonyl, optionally substituted heteroarylaminocarbonyl, optionally substituted alkylheteroarylaminocarbonyl, optionally substituted diheteroarylaminocarbonyl, optionally substituted phenyl, optionally substituted heteroaryl, optionally substituted heterocyclyl, optionally substituted $C_{1-20}$ alkylsulfonyl, or optionally substituted arylsulfonyl; $R^8$ and $R^9$ are, independently, hydrogen, halogen, cyano, nitro, optionally substituted $C_{1-6}$ alkyl, optionally substituted $C_{2-6}$ alkenyl, optionally substituted $C_{2-6}$ alkynyl or optionally substituted $C_{1-6}$ alkoxy; $R^{10}$ is hydrogen, halogen, optionally substituted $C_{1-6}$ alkyl, optionally substituted $C_{2-6}$alkenyl, optionally substituted $C_{2-6}$ alkynyl, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, cyano, nitro, formyl, $R^{20}ON=C(R^{21})$, optionally substituted $C_{1-6}$ alkylcarbonyl, optionally substituted $C_{1-6}$ alkoxycarbonyl or $SF_5$; or $R^1$ and $R^{10}$ together with the atoms to which they are attached may be joined to form a five, six or seven-membered saturated or unsaturated ring carbocylic or heterocyclic ring which may contain one or two hetero atoms selected from O, N or S and which may be optionally substituted by $C_{1-6}$alkyl, $C_{1-6}$ haloalkyl or halogen; $R^{16}$ is hydrogen, cyano, nitro, optionally substituted $C_{1-6}$ alkyl, optionally substituted $C_{3-7}$ cycloalkyl, optionally substituted ($C_{2-6}$)alkenyl($C_{1-6}$)alkyl, optionally substituted ($C_{2-6}$)alkynyl($C_{1-6}$)alkyl, optionally substituted phenyl, optionally substituted heteroaryl, optionally substituted $C_{1-6}$ alkylcarbonyl, optionally substituted $C_{1-6}$ alkoxycarbonyl, optionally substituted $C_{1-6}$ alkylamino, optionally substituted di($C_{1-6}$)alkylamino, optionally substituted $C_{1-6}$ alkylcarbonylamino, optionally substituted $C_{1-6}$ alkoxycarbonylamino, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, optionally substituted arylthio, optionally substituted arylsulfinyl, optionally substituted arylsulfonyl or $C_{1-6}$ acyloxy; $R^{17}$ is hydrogen, halogen, nitro, cyano, optionally substituted-$C_{1-8}$ alkyl, optionally substituted $C_{2-6}$ alkenyl, optionally substituted $C_{2-6}$ alkynyl, optionally substituted $C_{3-7}$ cycloalkyl, optionally substituted $C_{1-6}$ alkoxycarbonyl, optionally substituted $C_{1-6}$ alkylcarbonyl, optionally substituted $C_{1-6}$ alkylaminocarbonyl, optionally substituted di($C_{1-6}$)alkylaminocarbonyl, optionally substituted phenyl or optionally substituted heteroaryl; $R^{22}$ and $R^{23}$ are, independently, optionally substituted $C_{1-6}$ alkyl or $R^{22}$ and $R^{23}$ together with the N atom to which they are attached form a five, six or seven-membered heterocyclic ring which may contain one or two further hetero atoms selected from O, N or S and which may be optionally substituted by one or two $C_{1-6}$ alkyl groups; $R^{21}$ is hydrogen, optionally substituted phenyl or optionally substituted $C_{1-6}$ alkyl; and $R^{20}$ is hydrogen, optionally substituted phenyl ($C_{1-2}$)alkyl or optionally substituted $C_{1-20}$ alkyl.

The compounds of formula (IC) may exist in different geometric or optical isomers or tautomeric forms. This invention covers all such isomers and tautomers and mixtures thereof in all proportions.

In a further aspect, the present invention provides a compound of formula (ID):

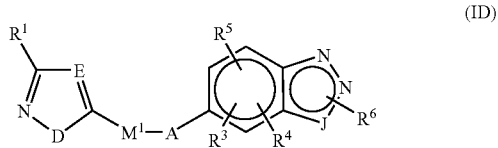
(ID)

wherein A, D, E, $M^1$, Y, J, $R^1$, $R^3$, $R^4$, $R^5$ and $R^6$ are as defined above for a compound of formula (IC). More preferred compounds of formula (ID) are those of formula (IE)

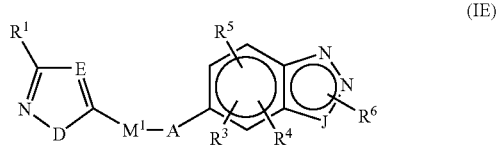
(IE)

wherein D is S, $NR^7$, $CR^8=CR^9$, $CR^8=N$, $CR^8=N(O)$, $N=CR^9$ or $N(O)=CR^9$; E is N or $CR^{10}$; $R^1$ is hydrogen, halogen, $C_{1-6}$ alkyl, $C_{2-6}$ alkenyl, $C_{2-6}$ alkynyl, $C_{1-6}$ cyanoalkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{3-6}$ cycloalkyl, $C_{3-7}$ cycloalkyl($C_{1-4}$)alkyl $C_{1-6}$ alkoxy($C_{1-6}$)alkyl, cyano, nitro or $SF_5$; A is $C_{1-6}$ alkylene, $C_{1-6}$ alkenylene, $C_{1-6}$ alkylenoxy, oxy($C_{1-6}$)alkylene, $C_{1-6}$ alkylenamino or $C_{1-6}$ alkylenethio, each of which is optionally substituted by $C_{1-3}$ alkyl, $C_{1-3}$ haloalkyl, $C_{1-3}$ cyanoalkyl, halogen, $C_{1-3}$ alkoxy, $C_{1-6}$ alkoxycarbonyl, cyano, $=O$, $=NR^{36}$ or $=CR^{37}R^{38}$; $M^1$ is $N(R^{11})C(=Y)$ or $N=C(SR^{13})$ where O or N is the atom of attachment to the ring containing E and D; Y is O, S or $NR^{16}$; J is N or $CR^{17}$; $R^{11}$ is hydrogen, $C_{1-6}$ alkyl, benzyloxymethyl, benzoyloxymethyl, $C_{1-6}$alkoxy($C_{1-6}$)alkyl, $C_{2-6}$ alkenyl($C_{1-6}$)alkyl (especially allyl), $C_{2-6}$ alkynyl($C_{1-6}$)alkyl (especially propargyl), $C_{1-10}$ alkylcarbonyl or $C_{1-10}$ alkoxycarbonyl (especially isobutoxycarbonyl); $R^{13}$ is $C_{1-10}$ alkyl, benzyloxymethyl, benzoyloxymethyl, $C_{1-6}$alkoxy($C_{1-6}$)alkyl, $C_{2-6}$ alkenyl($C_{1-6}$)alkyl (especially allyl), $C_{2-6}$ alkynyl($C_{1-6}$)alkyl (especially propargyl), $C_{1-10}$ alkylcarbonyl or $C_{1-10}$ alkoxycarbonyl (especially isobutoxycarbonyl); $R^3$, $R^4$ and $R^5$ are independently selected from hydrogen, halogen, $C_{1-6}$ alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{1-6}$ haloalkyl, cyano, nitro, $C_{1-6}$ alkylcarbonyl, $C_{1-6}$ alkoxycarbonyl or $SF_5$; $R^6$ is cyano, $C_{1-8}$ alkyl, $C_{2-6}$ haloalkyl, $C_{1-6}$ cyanoalkyl, $C_{2-6}$ alkenyl($C_{1-6}$)alkyl, $C_{2-6}$ alkynyl-($C_{1-6}$)alkyl, $C_{3-7}$ cycloalkyl, $C_{3-7}$ halocycloalkyl, $C_{3-7}$ cyanocycloalkyl, $C_{1-3}$ alkyl($C_{3-7}$)cycloalkyl, $C_{1-3}$ alkyl($C_{3-7}$)halocycloalkyl, $C_{5-6}$ cycloalkenyl, $C_{3-7}$ cycloalkyl($C_{1-6}$)alkyl, $C_{5-6}$ cycloalkenyl ($C_{1-6}$)alkyl, $C_{2-6}$ haloalkenyl($C_{1-6}$)alkyl, $C_{1-6}$ cyanoalkenyl ($C_{1-6}$)alkyl, $C_{1-6}$ alkoxy($C_{1-6}$)alkyl, $C_{3-6}$ alkenyloxy($C_{1-6}$) alkyl, $C_{3-6}$ alkynyloxy($C_{1-6}$)alkyl, aryloxy($C_{1-6}$)alkyl, formyl, $C_{1-6}$ carboxyalkyl, $C_{1-6}$alkylcarbonyl($C_{1-6}$)alkyl, $C_{2-6}$ alkenylcarbonyl($C_{1-6}$)alkyl, $C_{2-6}$ alkynylcarbonyl($C_{1-6}$) alkyl, $C_{1-6}$ alkoxycarbonyl($C_{1-6}$)alkyl, $C_{3-6}$ alkenyloxycarbonyl-($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio-($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl-($C_{1-6}$)alkyl, aminocarbonyl($C_{2-6}$)alkenyl, aminocarbonyl($C_{2-6}$)alkynyl, $C_{1-6}$ alkylaminocarbonyl($C_{1-6}$) alkyl, di($C_{1-6}$)alkylaminocarbonyl($C_{1-6}$)alkyl, $C_{1-6}$ alkylaminocarbonyl-($C_{2-6}$)alkenyl($C_{1-6}$)alkyl, di($C_{1-6}$)alkylaminocarbonyl($C_{2-6}$)alkenyl($C_{1-6}$)alkyl, alkylaminocarbonyl($C_{2-6}$)alkynyl($C_{1-6}$)alkyl, di($C_{1-6}$)alkylaminocarbonyl ($C_{1-6}$)alkenyl($C_{1-6}$)alkyl, $C_{1-6}$ alkoxycarbonyl, $C_{1-6}$ alkylcarbonyl, aminocarbonyl, $C_{1-6}$ alkylaminocarbonyl, di($C_{1-6}$)alkylaminocarbonyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy), phenyl($C_{1-4}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), phenyl($C_{2-4}$)alkenyl($C_{1-6}$)alkyl, (wherein the phenyl group is optionally substituted by halo, nitro, cyano, $C_{1-6}$ alkyl, $C_{1-6}$ haloalkyl, $C_{1-6}$ alkoxy, $C_{1-6}$ alkylsulfonyl or $C_{1-6}$ haloalkoxy), heteroaryl (optionally substituted by halo, nitro, cyano, $C_{1-6}$ alkyl, $C_{1-6}$ haloalkyl, $C_{1-6}$ alkoxy, $C_{1-6}$ alkylsulfonyl or $C_{1-6}$ haloalkoxy), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl($C_{1-4}$)alkyl (where the heteroaryl may be substituted by halo, nitro, cyano, $C_{1-6}$ alkyl, $C_{1-6}$ haloalkyl, $C_{1-6}$ alkoxy or $C_{1-6}$ haloalkoxy), or heterocyclyl($C_{1-4}$)alkyl (where the heterocyclyl may be substituted by halo, cyano, $C_{1-6}$alkyl, $C_{1-6}$ haloalkyl, $C_{1-6}$ alkoxy or $C_{1-6}$ haloalkoxy); $R^8$ and $R^9$ independently are, hydrogen, halogen, $C_{1-6}$ alkyl, $C_{1-6}$ haloalkyl $C_{2-6}$ alkenyl, $C_{1-6}$ alkynyl, $C_{1-6}$ alkoxy or $C_{1-6}$ haloalkoxy; $R^{10}$ is hydrogen, halogen, $C_{1-6}$ alkyl, $C_{2-6}$ alkenyl, $C_{1-6}$ alkynyl, $C_{1-6}$ haloalkyl, $C_{1-6}$ alkoxy, $C_{1-6}$ alkoxy ($C_{1-6}$)alkyl, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{1-6}$ haloalkyl, cyano, nitro, formyl, $CH=NOR^{20}$, $C_{1-6}$alkylcarbonyl, $C_{1-6}$ alkoxycarbonyl or $SF_5$; or together $R^1$ and $R^{10}$ together with the atoms to which they are attached may be joined to form a five, six or seven-membered saturated or unsaturated ring carbocylic or heterocyclic ring which may contain one or two hetero atoms selected from O, N or S and which may be optionally substituted by $C_{1-6}$ alkyl, $C_{1-6}$ haloalkyl or halogen; $R^{16}$ is cyano, nitro, $C_{1-6}$ alkyl, $C_{1-6}$ haloalkyl, $C_{3-7}$ cycloalkyl, $C_{3-7}$ cycloalkyl($C_{1-6}$)alkyl, $CH_2(C_{2-6})$alkenyl, $CH_2(C_{2-6})$alkynyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy) heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylcarbonyl, $C_{1-6}$ alkoxycarbonyl, $C_{1-6}$ alkylamino, di($C_{1-6}$)alkylamino, $C_{1-6}$ alkylcarbonylamino, $C_{1-6}$ alkoxycarbonylamino, $C_{1-6}$ alkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, arylthio, arylsulfinyl, arylsulfonyl or $OCO(C_{1-6})$alkyl; $R^{17}$ is hydrogen, halogen, nitro, cyano, $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{2-6}$ haloalkenyl, $C_{3-7}$ cycloalkyl$(C_{1-6})$alkyl, $C_{1-6}$alkox$(C_{1-6})$alkyl, $C_{1-6}$ alkoxycarbonyl, $C_{1-6}$ alkylcarbonyl, $C_{1-6}$ alkylaminocarbonyl, di($C_{1-6}$alkylaminocarbonyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy) or heteroaryl (optionally substituted by halo,nitro, cyano, $C_{1-6}$ alkyl, $C_{1-6}$ haloalkyl, $C_{1-6}$ alkoxy or $C_{1-6}$ haloalkoxy); $R^{36}$ is $C_{1-6}$ alkyl, $OR^{39}$ or $NR^{40}R^{41}$; $R^{37}$ is hydrogen, $C_{1-6}$ alkyl or $C_{1-6}$ haloalkyl; $R^{38}$ is hydrogen, $C_{1-6}$ alkyl, $C_{1-6}$ haloalkyl, $C_{1-6}$ alkoxy, cyano, $C_{1-6}$ alkoxycarbonyl, $C_{1-6}$ alkylcarbonyl or $NR^{42}R^{43}$; $R^{22}$ and $R^{23}$ independently are, hydrogen, $C_{1-6}$ alkyl, $CH_2(C_{1-4}$ haloalkyl), $C_{1-6}$ cyanoalkyl, $C_{1-6}$ alkoxy$(C_{1-6})$alkyl, $C_{1-6}$ alkylthio$(C_{1-6})$ alkyl, $C_{1-6}$ alkoxy-$(C_{1-6})$alkoxy$(C_{1-6})$alkyl, phenyl$(C_{1-4})$ alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl-$(C_{1-4})$alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl$(C_{1-4})$alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), or $R^{22}$ and $R^{23}$ together with the N atom to which they are attached form a five, six or seven-membered heterocyclic ring which may contain one or two further hetero atoms selected from O, N or S and which may be optionally substituted by one or two $C_{1-6}$ alkyl groups; $R^{39}$ is $C_{1-6}$ alkyl or optionally substituted phenyl$(C_{1-2})$alkyl; $R^{40}$ and $R^{41}$ independently are, hydrogen, $C_{1-8}$ alkyl or phenyl (optionally substituted by halo, nitro, cyano, $C_{1-6}$ alkyl, $C_{1-6}$ haloalkyl, $C_{1-6}$ alkoxy or $C_{1-6}$ haloalkoxy); $R^{21}$ is hydrogen or $C_{1-3}$ alkyl; $R^{20}$ is $C_{1-6}$ alkyl or phenyl$(C_{1-2})$alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy); and $R^{42}$ and $R^{43}$ independently, are, hydrogen, $C_{1-8}$ alkyl, $C_{3-7}$ cycloalkyl, $C_{3-6}$ alkenyl, $C_3$ alkynyl, $C_{2-6}$ haloalkyl, $C_{1-6}$ alkoxy$(C_{1-6})$alkyl, $C_{1-6}$ alkoxycarbonyl$(C_{1-6})$alkyl, carboxy$(C_{1-6})$alkyl or phenyl$(C_{1-2})$alkyl; or $R^{42}$ and $R^{43}$ together with the N atom to which they are attached form a five, six or seven-membered heterocyclic ring which may contain one or two further hetero atoms selected from O, N or S and which may be optionally substituted by one or two $C_{1-6}$ alkyl groups.

Preferably A is $C_{1-4}$ alkylene —C(O)— or $C_{1-4}$ alkyleneoxy.

Preferably D is S or $CR^8$=$CR^9$, where $R^8$ and $R^9$ are, independently, hydrogen, halogen, $C_{1-6}$ alkyl, $C_{1-6}$ haloalkyl $C_{2-6}$ alkenyl, $C_{1-6}$ alkynyl, $C_{1-6}$ alkoxy or $C_{1-6}$ haloalkoxy.

Preferably E is N or $CR^{10}$ where $R^{10}$ is hydrogen, halogen, $C_{1-6}$ alkyl, $C_{1-6}$ haloalkyl, $C_{1-6}$ alkoxy, $C_{1-6}$ haloalkoxy, $C_{1-6}$ alkoxy $(C_{1-6})$alkyl, $C_{1-6}$ alkylthio or $SF_5$; or $R^1$ and $R^{10}$ together with the atoms to which they are attached form a benzene ring optionally substituted by $C_{1-6}$ alkyl, $C_{1-6}$ haloalkyl or halogen.

A preferred value of $M^1$ is $N(R^{11})C(\!=\!O)$ where N is the atom of attachment to the ring containing E and D; and $R^{11}$ is hydrogen, $C_{1-6}$ alkyl, $C_{1-6}$ alkoxy$(C_{1-6})$alkyl, benzyloxymethyl or benzoyloxymethyl.

Preferably Y is O.

Preferably J is N or $CR^{17}$ where $R^{17}$ is hydrogen, $C_{1-6}$ alkyl, $C_{1-6}$ haloalkyl, cyano, halogen or nitro.

$R^1$ is preferably hydrogen, halogen, $C_{1-6}$ alkyl, $C_{2-6}$ alkenyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{3-6}$ cycloalkyl, cyano, nitro or $SF_5$.

Preferably $^3$, $R^4$ and $R^5$ are independently hydrogen, $C_{1-3}$ alkyl or halogen.

$R^6$ is preferably $C_{1-8}$ alkyl, $C_{1-6}$ haloalkyl, $C_{1-6}$ cyanoalkyl, $C_{2-6}$ alkenyl$(C_{1-6})$alkyl, $C_{2-6}$ alkynyl $(C_{1-6})$ alkyl, $C_{3-7}$ cycloalkyl, $C_{3-7}$ halocycloalkyl, $C_{3-7}$ cyanocycloalkyl, $C_{1-3}$ alkyl-$(C_{3-7})$cycloalkyl, $C_{1-3}$ alkyl$(C_{3-7})$halocycloalkyl, $C_{5-6}$ cycloalkenyl, $C_{3-7}$ cycloalkyl$(C_{1-6})$alkyl, $C_{5-6}$ cycloalkenyl$(C_{1-6})$alkyl, $C_{2-6}$ haloalkenyl$(C_{1-6})$alkyl, $C_{1-6}$ cyanoalkenyl$(C_{1-6})$alkyl, $C_{1-6}$ alkoxy$(C_{1-6})$alkyl, $C_{3-6}$ alkenyloxy$(C_{1-6})$alkyl, $C_{3-6}$ alkenyloxy$(C_{1-6})$alkyl, aryloxy $(C_{1-6})$alkyl, $C_{1-6}$ carboxyalkyl, $C_{1-6}$ alkylcarbonyl$(C_{1-6})$ alkyl, $C_{2-6}$ alkenylcarbonyl$(C_{1-6})$alkyl, $C_{2-6}$ alkynylcarbonyl $(C_{1-6})$alkyl, $C_{1-6}$ alkoxycarbonyl$(C_{1-6})$alkyl, $C_{3-6}$ alkenyloxycarbonyl$(C_{1-6})$-alkyl, $C_{3-6}$ alkynyloxycarbonyl $(C_{1-6})$alkyl, aryloxycarbonyl$(C_{1-6})$alkyl, $C_{1-6}$ alkylthio$(C_{1-6})$-alkyl, $C_{1-6}$ alkylsulfinyl$(C_{1-6})$alkyl, $C_{1-6}$ alkylsulfonyl$(C_{1-6})$alkyl, aminocarbonyl$(C_{1-6})$alkyl, aminocarbonyl$(C_{2-6})$alkenyl, aminocarbonyl$(C_{2-6})$alkynyl, $C_{1-6}$ alkylaminocarbonyl$(C_{1-6})$alkyl, di$(C_{1-6})$alkylaminocarbonyl $(C_{1-6})$alkyl, $C_{1-6}$ alkylaminocarbonyl$(C_{1-6})$alkenyl$(C_{1-6})$ alkyl, di $(C_{1-6})$alkylaminocarbonyl$(C_{1-6})$alkenyl$(C_{1-6})$alkyl, alkylaminocarbonyl$(C_{1-6})$alkynyl$(C_{1-6})$alkyl, di$(C_{1-6})$alkylaminocarbonyl$(C_{1-6})$alkynyl$(C_{1-6})$alkyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy), phenyl$(C_{1-4})$alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), phenyl$(C_{2-4})$alkenyl$(C_{1-6})$alkyl, (wherein the phenyl group is optionally substituted by halo, nitro, cyano, $C_{1-6}$ alkyl, $C_{1-6}$ haloalkyl, $C_{1-6}$ alkoxy, $C_{1-6}$ alkylsulfonyl or $C_{1-6}$ haloalkoxy), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl$(C_{1-4})$alkyl (wherein the heteroaryl group is optionally substituted by halo, nitro, cyano, $C_{1-6}$ alkyl, $C_{1-6}$ haloalkyl, $C_{1-6}$alkoxy, $C_{1-6}$ alkylsulfonyl or $C_{1-6}$ haloalkoxy)or heterocyclyl$(C_{1-4})$ alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy).

More preferred optionally substituted rings of formula

include optionally substituted isothiazolyl, optionally substituted pyridyl, optionally substituted pyrimidinyl, optionally substituted quinazolinyl and optionally substituted quinolinyl groups in which the optional substituents are chosen from halo, $C_{1-6}$ alkyl, $C_{1-6}$ haloalkyl, $C_{1-6}$ alkoxy, $C_{1-6}$ alkoxy$(C_{1-6})$alkyl or $C_{1-6}$ haloalkoxy.

Most preferred optionally substituted rings of formula

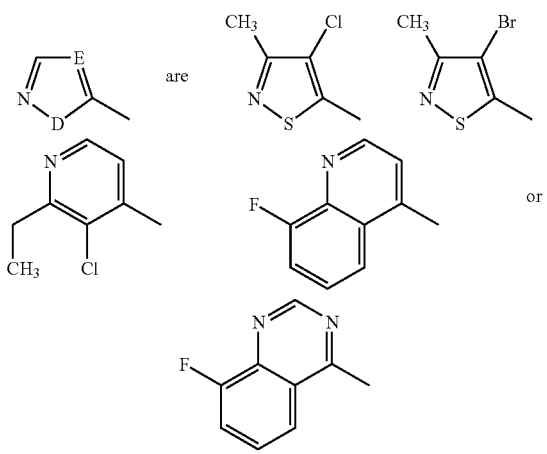

are or

More preferably A is $CH_2$ or $CH_2O$, even more preferably $CH_2$.

It is more preferred that $M^1$ is $NR^{11}=C(=O)$, where $R^{11}$ is hydrogen, $C_{1-4}$ alkyl, $C_{1-4}$ alkoxy $(C_{1-4})$alkyl, benzyloxymethyl or benzoyloxymethyl. It is especially preferred that $R^{11}$ is hydrogen, ethyl, ethoxymethyl, allyl or propargyl.

It is more preferred that $R^3$, $R^4$ and $R^5$ are independently, hydrogen, or halogen (especially fluorine); it is especially preferred that each of $R^3$, $R^4$ and $R^5$ is hydrogen.

More preferably J is N or $CR^{17}$ where $R^{17}$ is hydrogen, methyl, or halogen.

More preferably $R^6$ is $C_{1-8}$ alkyl, $C_{2-8}$ haloalkyl, $C_{1-8}$ cyanoalkyl, $C_{3-7}$ cycloalkyl, $C_{1-3}$ alkyl $(C_{3-7})$ cycloalkyl, $C_{1-6}$ alkoxy $(C_{1-6})$ alkyl, heterocyclic (optionally substituted by halo, nitro, cyano, $C_{1-6}$ alkyl, $C_{1-6}$ haloalkyl, $C_{1-6}$ alkoxy or $C_{1-6}$ haloalkoxy), phenyl (optionally substituted by halogen, $C_{1-6}$ alkyl, $C_{1-6}$ haloalkyl, $C_{1-6}$ alkoxy, nitro, cyano or $C_{1-6}$ alkylsulfonyl) or heteroaryl (optionally substituted by halogen, $C_{1-6}$ alkyl, $C_{1-6}$ haloalkyl, $C_{1-6}$ alkoxy, nitro, cyano or $C_{1-6}$ alkylsulfonyl).

Particularly preferred values of $R_6$ are $C_{1-8}$ alkyl, $C_{2-6}$ haloalkyl, $C_{1-6}$alkoxy$(C_{1-6})$alkyl, $C_{3-7}$cycloalkyl or $C_{3-7}$ cycloalkyl$(C_{1-6})$alkyl.

Particularly preferred values of the group:

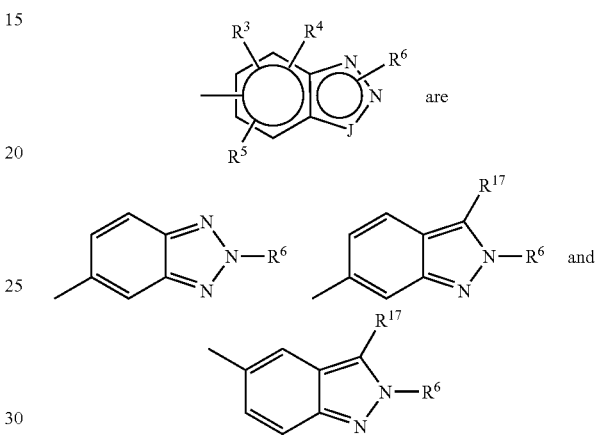

are

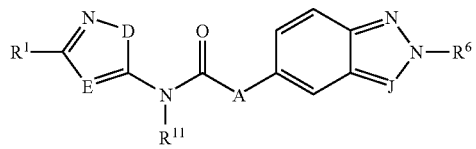

and

The compounds in the following Tables illustrate compounds of the invention.

TABLE A1

Table A1 provides 432 compounds of Formula A1 wherein $R^1$, D, E, $R^{11}$, A and J are as defined in Table A1 and $R^6$ is methyl.

(A1)

| Compound No. | $R^1$ | D | E | $R^{11}$ | A | J |
|---|---|---|---|---|---|---|
| A1.1 | $CH_3$ | S | C—Cl | H | $CH_2$ | N |
| A1.2 | $CH_3$ | S | C—Cl | $CH_2CH_3$ | $CH_2$ | N |
| A1.3 | $CH_3$ | S | C—Cl | $CH_2C=CH_2$ | $CH_2$ | N |
| A1.4 | $CH_3$ | S | C—Cl | $CH_2C.CH$ | $CH_2$ | N |
| A1.5 | $CH_3$ | S | C—Cl | $CH_2OCH_3$ | $CH_2$ | N |
| A1.6 | $CH_3$ | S | C—Cl | $CH_2OCH_2CH_3$ | $CH_2$ | N |
| A1.7 | $CH_3$ | S | C—Br | H | $CH_2$ | N |
| A1.8 | $CH_3$ | S | C—Br | $CH_2CH_3$ | $CH_2$ | N |
| A1.9 | $CH_3$ | S | C—Br | $CH_2C=CH_2$ | $CH_2$ | N |
| A1.10 | $CH_3$ | S | C—Br | $CH_2C.CH$ | $CH_2$ | N |
| A1.11 | $CH_3$ | S | C—Br | $CH_2OCH_3$ | $CH_2$ | N |
| A1.12 | $CH_3$ | S | C—Br | $CH_2OCH_2CH_3$ | $CH_2$ | N |
| A1.13 | $CH_2CH_3$ | S | C—Cl | H | $CH_2$ | N |
| A1.14 | $CH_2CH_3$ | S | C—Cl | $CH_2CH_3$ | $CH_2$ | N |
| A1.15 | $CH_2CH_3$ | S | C—Cl | $CH_2C=CH_2$ | $CH_2$ | N |
| A1.16 | $CH_2CH_3$ | S | C—Cl | $CH_2C.CH$ | $CH_2$ | N |
| A1.17 | $CH_2CH_3$ | S | C—Cl | $CH_2OCH_3$ | $CH_2$ | N |
| A1.18 | $CH_2CH_3$ | S | C—Cl | $CH_2OCH_2CH_3$ | $CH_2$ | N |
| A1.19 | $CH_2CH_3$ | S | C—Br | H | $CH_2$ | N |
| A1.20 | $CH_2CH_3$ | S | C—Br | $CH_2CH_3$ | $CH_2$ | N |
| A1.21 | $CH_2CH_3$ | S | C—Br | $CH_2C=CH_2$ | $CH_2$ | N |

TABLE A1-continued

Table A1 provides 432 compounds of Formula A1 wherein $R^1$, D, E, $R^{11}$, A and J are as defined in Table A1 and $R^6$ is methyl.

(A1)

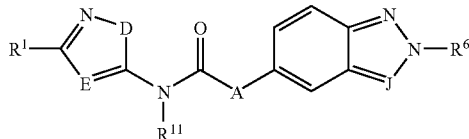

| Compound No. | $R^1$ | D | E | $R^{11}$ | A | J |
|---|---|---|---|---|---|---|
| A1.22 | $CH_2CH_3$ | S | C—Br | $CH_2C.CH$ | $CH_2$ | N |
| A1.23 | $CH_2CH_3$ | S | C—Br | $CH_2OCH_3$ | $CH_2$ | N |
| A1.24 | $CH_2CH_3$ | S | C—Br | $CH_2OCH_2CH_3$ | $CH_2$ | N |
| A1.25 | $CH_3$ | S | C—Cl | H | $CH(CH_3)$ | N |
| A1.26 | $CH_3$ | S | C—Cl | $CH_2CH_3$ | $CH(CH_3)$ | N |
| A1.27 | $CH_3$ | S | C—Cl | $CH_2C=CH_2$ | $CH(CH_3)$ | N |
| A1.28 | $CH_3$ | S | C—Cl | $CH_2C.CH$ | $CH(CH_3)$ | N |
| A1.29 | $CH_3$ | S | C—Cl | $CH_2OCH_3$ | $CH(CH_3)$ | N |
| A1.30 | $CH_3$ | S | C—Cl | $CH_2OCH_2CH_3$ | $CH(CH_3)$ | N |
| A1.31 | $CH_3$ | S | C—Br | H | $CH(CH_3)$ | N |
| A1.32 | $CH_3$ | S | C—Br | $CH_2CH_3$ | $CH(CH_3)$ | N |
| A1.33 | $CH_3$ | S | C—Br | $CH_2C=CH_2$ | $CH(CH_3)$ | N |
| A1.34 | $CH_3$ | S | C—Br | $CH_2C.CH$ | $CH(CH_3)$ | N |
| A1.35 | $CH_3$ | S | C—Br | $CH_2OCH_3$ | $CH(CH_3)$ | N |
| A1.36 | $CH_3$ | S | C—Br | $CH_2OCH_2CH_3$ | $CH(CH_3)$ | N |
| A1.37 | $CH_2CH_3$ | S | C—Cl | H | $CH(CH_3)$ | N |
| A1.38 | $CH_2CH_3$ | S | C—Cl | $CH_2CH_3$ | $CH(CH_3)$ | N |
| A1.39 | $CH_2CH_3$ | S | C—Cl | $CH_2C=CH_2$ | $CH(CH_3)$ | N |
| A1.40 | $CH_2CH_3$ | S | C—Cl | $CH_2C.CH$ | $CH(CH_3)$ | N |
| A1.41 | $CH_2CH_3$ | S | C—Cl | $CH_2OCH_3$ | $CH(CH_3)$ | N |
| A1.42 | $CH_2CH_3$ | S | C—Cl | $CH_2OCH_2CH_3$ | $CH(CH_3)$ | N |
| A1.43 | $CH_2CH_3$ | S | C—Br | H | $CH(CH_3)$ | N |
| A1.44 | $CH_2CH_3$ | S | C—Br | $CH_2CH_3$ | $CH(CH_3)$ | N |
| A1.45 | $CH_2CH_3$ | S | C—Br | $CH_2C=CH_2$ | $CH(CH_3)$ | N |
| A1.46 | $CH_2CH_3$ | S | C—Br | $CH_2C.CH$ | $CH(CH_3)$ | N |
| A1.47 | $CH_2CH_3$ | S | C—Br | $CH_2OCH_3$ | $CH(CH_3)$ | N |
| A1.48 | $CH_2CH_3$ | S | C—Br | $CH_2OCH_2CH_3$ | $CH(CH_3)$ | N |
| A1.49 | $CH_3$ | S | C—Cl | H | CHF | N |
| A1.50 | $CH_3$ | S | C—Cl | $CH_2CH_3$ | CHF | N |
| A1.51 | $CH_3$ | S | C—Cl | $CH_2C=CH_2$ | CHF | N |
| A1.52 | $CH_3$ | S | C—Cl | $CH_2C.CH$ | CHF | N |
| A1.53 | $CH_3$ | S | C—Cl | $CH_2OCH_3$ | CHF | N |
| A1.54 | $CH_3$ | S | C—Cl | $CH_2OCH_2CH_3$ | CHF | N |
| A1.55 | $CH_3$ | S | C—Br | H | CHF | N |
| A1.56 | $CH_3$ | S | C—Br | $CH_2CH_3$ | CHF | N |
| A1.57 | $CH_3$ | S | C—Br | $CH_2C=CH_2$ | CHF | N |
| A1.58 | $CH_3$ | S | C—Br | $CH_2C.CH$ | CHF | N |
| A1.59 | $CH_3$ | S | C—Br | $CH_2OCH_3$ | CHF | N |
| A1.60 | $CH_3$ | S | C—Br | $CH_2OCH_2CH_3$ | CHF | N |
| A1.61 | $CH_2CH_3$ | S | C—Cl | H | CHF | N |
| A1.62 | $CH_2CH_3$ | S | C—Cl | $CH_2CH_3$ | CHF | N |
| A1.63 | $CH_2CH_3$ | S | C—Cl | $CH_2C=CH_2$ | CHF | N |
| A1.64 | $CH_2CH_3$ | S | C—Cl | $CH_2C.CH$ | CHF | N |
| A1.65 | $CH_2CH_3$ | S | C—Cl | $CH_2OCH_3$ | CHF | N |
| A1.66 | $CH_2CH_3$ | S | C—Cl | $CH_2OCH_2CH_3$ | CHF | N |
| A1.67 | $CH_2CH_3$ | S | C—Br | H | CHF | N |
| A1.68 | $CH_2CH_3$ | S | C—Br | $CH_2CH_3$ | CHF | N |
| A1.69 | $CH_2CH_3$ | S | C—Br | $CH_2C=CH_2$ | CHF | N |
| A1.70 | $CH_2CH_3$ | S | C—Br | $CH_2C.CH$ | CHF | N |
| A1.71 | $CH_2CH_3$ | S | C—Br | $CH_2OCH_3$ | CHF | N |
| A1.72 | $CH_2CH_3$ | S | C—Br | $CH_2OCH_2CH_3$ | CHF | N |
| A1.73 | $CH_3$ | S | C—Cl | H | $CH_2O$ | N |
| A1.74 | $CH_3$ | S | C—Cl | $CH_2CH_3$ | $CH_2O$ | N |
| A1.75 | $CH_3$ | S | C—Cl | $CH_2C=CH_2$ | $CH_2O$ | N |
| A1.76 | $CH_3$ | S | C—Cl | $CH_2C.CH$ | $CH_2O$ | N |
| A1.77 | $CH_3$ | S | C—Cl | $CH_2OCH_3$ | $CH_2O$ | N |
| A1.78 | $CH_3$ | S | C—Cl | $CH_2OCH_2CH_3$ | $CH_2O$ | N |
| A1.79 | $CH_3$ | S | C—Br | H | $CH_2O$ | N |
| A1.80 | $CH_3$ | S | C—Br | $CH_2CH_3$ | $CH_2O$ | N |
| A1.81 | $CH_3$ | S | C—Br | $CH_2C=CH_2$ | $CH_2O$ | N |
| A1.82 | $CH_3$ | S | C—Br | $CH_2C.CH$ | $CH_2O$ | N |
| A1.83 | $CH_3$ | S | C—Br | $CH_2OCH_3$ | $CH_2O$ | N |
| A1.84 | $CH_3$ | S | C—Br | $CH_2OCH_2CH_3$ | $CH_2O$ | N |
| A1.85 | $CH_2CH_3$ | S | C—Cl | H | $CH_2O$ | N |
| A1.86 | $CH_2CH_3$ | S | C—Cl | $CH_2CH_3$ | $CH_2O$ | N |

TABLE A1-continued

Table A1 provides 432 compounds of Formula A1 wherein $R^1$, D, E, $R^{11}$, A and J are as defined in Table A1 and $R^6$ is methyl.

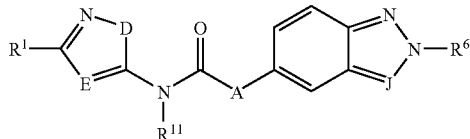

(A1)

| Compound No. | $R^1$ | D | E | $R^{11}$ | A | J |
|---|---|---|---|---|---|---|
| A1.87 | $CH_2CH_3$ | S | C—Cl | $CH_2C=CH_2$ | $CH_2O$ | N |
| A1.88 | $CH_2CH_3$ | S | C—Cl | $CH_2C.CH$ | $CH_2O$ | N |
| A1.89 | $CH_2CH_3$ | S | C—Cl | $CH_2OCH_3$ | $CH_2O$ | N |
| A1.90 | $CH_2CH_3$ | S | C—Cl | $CH_2OCH_2CH_3$ | $CH_2O$ | N |
| A1.91 | $CH_2CH_3$ | S | C—Br | H | $CH_2O$ | N |
| A1.92 | $CH_2CH_3$ | S | C—Br | $CH_2CH_3$ | $CH_2O$ | N |
| A1.93 | $CH_2CH_3$ | S | C—Br | $CH_2C=CH_2$ | $CH_2O$ | N |
| A1.94 | $CH_2CH_3$ | S | C—Br | $CH_2C.CH$ | $CH_2O$ | N |
| A1.95 | $CH_2CH_3$ | S | C—Br | $CH_2OCH_3$ | $CH_2O$ | N |
| A1.96 | $CH_2CH_3$ | S | C—Br | $CH_2OCH_2CH_3$ | $CH_2O$ | N |
| A1.97 | $CH_3$ | CH=CH | C—Cl | H | $CH_2$ | N |
| A1.98 | $CH_3$ | CH=CH | C—Cl | $CH_2CH_3$ | $CH_2$ | N |
| A1.99 | $CH_3$ | CH=CH | C—Cl | $CH_2C=CH_2$ | $CH_2$ | N |
| A1.100 | $CH_3$ | CH=CH | C—Cl | $CH_2C.CH$ | $CH_2$ | N |
| A1.101 | $CH_3$ | CH=CH | C—Cl | $CH_2OCH_3$ | $CH_2$ | N |
| A1.102 | $CH_3$ | CH=CH | C—Cl | $CH_2OCH_2CH_3$ | $CH_2$ | N |
| A1.103 | $CH_2CH_3$ | CH=CH | C—Cl | H | $CH_2$ | N |
| A1.104 | $CH_2CH_3$ | CH=CH | C—Cl | $CH_2CH_3$ | $CH_2$ | N |
| A1.105 | $CH_2CH_3$ | CH=CH | C—Cl | $CH_2C=CH_2$ | $CH_2$ | N |
| A1.106 | $CH_2CH_3$ | CH=CH | C—Cl | $CH_2C.CH$ | $CH_2$ | N |
| A1.107 | $CH_2CH_3$ | CH=CH | C—Cl | $CH_2OCH_3$ | $CH_2$ | N |
| A1.108 | $CH_2CH_3$ | CH=CH | C—Cl | $CH_2OCH_2CH_3$ | $CH_2$ | N |
| A1.109 | $CH_3$ | CH=CH | C—Cl | H | $CH(CH_3)$ | N |
| A1.110 | $CH_3$ | CH=CH | C—Cl | $CH_2CH_3$ | $CH(CH_3)$ | N |
| A1.111 | $CH_3$ | CH=CH | C—Cl | $CH_2C=CH_2$ | $CH(CH_3)$ | N |
| A1.112 | $CH_3$ | CH=CH | C—Cl | $CH_2C.CH$ | $CH(CH_3)$ | N |
| A1.113 | $CH_3$ | CH=CH | C—Cl | $CH_2OCH_3$ | $CH(CH_3)$ | N |
| A1.114 | $CH_3$ | CH=CH | C—Cl | $CH_2OCH_2CH_3$ | $CH(CH_3)$ | N |
| A1.115 | $CH_2CH_3$ | CH=CH | C—Cl | H | $CH(CH_3)$ | N |
| A1.116 | $CH_2CH_3$ | CH=CH | C—Cl | $CH_2CH_3$ | $CH(CH_3)$ | N |
| A1.117 | $CH_2CH_3$ | CH=CH | C—Cl | $CH_2C=CH_2$ | $CH(CH_3)$ | N |
| A1.118 | $CH_2CH_3$ | CH=CH | C—Cl | $CH_2C.CH$ | $CH(CH_3)$ | N |
| A1.119 | $CH_2CH_3$ | CH=CH | C—Cl | $CH_2OCH_3$ | $CH(CH_3)$ | N |
| A1.120 | $CH_2CH_3$ | CH=CH | C—Cl | $CH_2OCH_2CH_3$ | $CH(CH_3)$ | N |
| A1.121 | $CH_3$ | CH=CH | C—Cl | H | CHF | N |
| A1.122 | $CH_3$ | CH=CH | C—Cl | $CH_2CH_3$ | CHF | N |
| A1.123 | $CH_3$ | CH=CH | C—Cl | $CH_2C=CH_2$ | CHF | N |
| A1.124 | $CH_3$ | CH=CH | C—Cl | $CH_2C.CH$ | CHF | N |
| A1.125 | $CH_3$ | CH=CH | C—Cl | $CH_2OCH_3$ | CHF | N |
| A1.126 | $CH_3$ | CH=CH | C—Cl | $CH_2OCH_2CH_3$ | CHF | N |
| A1.127 | $CH_2CH_3$ | CH=CH | C—Cl | H | CHF | N |
| A1.128 | $CH_2CH_3$ | CH=CH | C—Cl | $CH_2CH_3$ | CHF | N |
| A1.129 | $CH_2CH_3$ | CH=CH | C—Cl | $CH_2C=CH_2$ | CHF | N |
| A1.130 | $CH_2CH_3$ | CH=CH | C—Cl | $CH_2C.CH$ | CHF | N |
| A1.131 | $CH_2CH_3$ | CH=CH | C—Cl | $CH_2OCH_3$ | CHF | N |
| A1.132 | $CH_2CH_3$ | CH=CH | C—Cl | $CH_2OCH_2CH_3$ | CHF | N |
| A1.133 | $CH_3$ | CH=CH | C—Cl | H | $CH_2O$ | N |
| A1.134 | $CH_3$ | CH=CH | C—Cl | $CH_2CH_3$ | $CH_2O$ | N |
| A1.135 | $CH_3$ | CH=CH | C—Cl | $CH_2C=CH_2$ | $CH_2O$ | N |
| A1.136 | $CH_3$ | CH=CH | C—Cl | $CH_2C.CH$ | $CH_2O$ | N |
| A1.137 | $CH_3$ | CH=CH | C—Cl | $CH_2OCH_3$ | $CH_2O$ | N |
| A1.138 | $CH_3$ | CH=CH | C—Cl | $CH_2OCH_2CH_3$ | $CH_2O$ | N |
| A1.139 | $CH_2CH_3$ | CH=CH | C—Cl | H | $CH_2O$ | N |
| A1.140 | $CH_2CH_3$ | CH=CH | C—Cl | $CH_2CH_3$ | $CH_2O$ | N |
| A1.141 | $CH_2CH_3$ | CH=CH | C—Cl | $CH_2C=CH_2$ | $CH_2O$ | N |
| A1.142 | $CH_2CH_3$ | CH=CH | C—Cl | $CH_2C.CH$ | $CH_2O$ | N |
| A1.143 | $CH_2CH_3$ | CH=CH | C—Cl | $CH_2OCH_3$ | $CH_2O$ | N |
| A1.144 | $CH_2CH_3$ | CH=CH | C—Cl | $CH_2OCH_2CH_3$ | $CH_2O$ | N |
| A1.145 | $CH_3$ | S | C—Cl | H | $CH_2$ | C—H |
| A1.146 | $CH_3$ | S | C—Cl | $CH_2CH_3$ | $CH_2$ | C—H |
| A1.147 | $CH_3$ | S | C—Cl | $CH_2C=CH_2$ | $CH_2$ | C—H |
| A1.148 | $CH_3$ | S | C—Cl | $CH_2C.CH$ | $CH_2$ | C—H |
| A1.149 | $CH_3$ | S | C—Cl | $CH_2OCH_3$ | $CH_2$ | C—H |
| A1.150 | $CH_3$ | S | C—Cl | $CH_2OCH_2CH_3$ | $CH_2$ | C—H |
| A1.151 | $CH_3$ | S | C—Br | H | $CH_2$ | C—H |

TABLE A1-continued

Table A1 provides 432 compounds of Formula A1 wherein $R^1$, D, E, $R^{11}$, A and J are as defined in Table A1 and $R^6$ is methyl.

(A1)

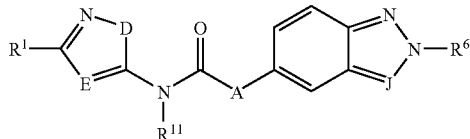

| Compound No. | $R^1$ | D | E | $R^{11}$ | A | J |
|---|---|---|---|---|---|---|
| A1.152 | $CH_3$ | S | C—Br | $CH_2CH_3$ | $CH_2$ | C—H |
| A1.153 | $CH_3$ | S | C—Br | $CH_2C=CH_2$ | $CH_2$ | C—H |
| A1.154 | $CH_3$ | S | C—Br | $CH_2C.CH$ | $CH_2$ | C—H |
| A1.155 | $CH_3$ | S | C—Br | $CH_2OCH_3$ | $CH_2$ | C—H |
| A1.156 | $CH_3$ | S | C—Br | $CH_2OCH_2CH_3$ | $CH_2$ | C—H |
| A1.157 | $CH_2CH_3$ | S | C—Cl | H | $CH_2$ | C—H |
| A1.158 | $CH_2CH_3$ | S | C—Cl | $CH_2CH_3$ | $CH_2$ | C—H |
| A1.159 | $CH_2CH_3$ | S | C—Cl | $CH_2C=CH_2$ | $CH_2$ | C—H |
| A1.160 | $CH_2CH_3$ | S | C—Cl | $CH_2C.CH$ | $CH_2$ | C—H |
| A1.161 | $CH_2CH_3$ | S | C—Cl | $CH_2OCH_3$ | $CH_2$ | C—H |
| A1.162 | $CH_2CH_3$ | S | C—Cl | $CH_2OCH_2CH_3$ | $CH_2$ | C—H |
| A1.163 | $CH_2CH_3$ | S | C—Br | H | $CH_2$ | C—H |
| A1.164 | $CH_2CH_3$ | S | C—Br | $CH_2CH_3$ | $CH_2$ | C—H |
| A1.165 | $CH_2CH_3$ | S | C—Br | $CH_2C=CH_2$ | $CH_2$ | C—H |
| A1.166 | $CH_2CH_3$ | S | C—Br | $CH_2C.CH$ | $CH_2$ | C—H |
| A1.167 | $CH_2CH_3$ | S | C—Br | $CH_2OCH_3$ | $CH_2$ | C—H |
| A1.168 | $CH_2CH_3$ | S | C—Br | $CH_2OCH_2CH_3$ | $CH_2$ | C—H |
| A1.169 | $CH_3$ | S | C—Cl | H | $CH_2$ | C—Cl |
| A1.170 | $CH_3$ | S | C—Cl | $CH_2CH_3$ | $CH_2$ | C—Cl |
| A1.171 | $CH_3$ | S | C—Cl | $CH_2C=CH_2$ | $CH_2$ | C—Cl |
| A1.172 | $CH_3$ | S | C—Cl | $CH_2C.CH$ | $CH_2$ | C—Cl |
| A1.173 | $CH_3$ | S | C—Cl | $CH_2OCH_3$ | $CH_2$ | C—Cl |
| A1.174 | $CH_3$ | S | C—Cl | $CH_2OCH_2CH_3$ | $CH_2$ | C—Cl |
| A1.175 | $CH_3$ | S | C—Br | H | $CH_2$ | C—Cl |
| A1.176 | $CH_3$ | S | C—Br | $CH_2CH_3$ | $CH_2$ | C—Cl |
| A1.177 | $CH_3$ | S | C—Br | $CH_2C=CH_2$ | $CH_2$ | C—Cl |
| A1.178 | $CH_3$ | S | C—Br | $CH_2C.CH$ | $CH_2$ | C—Cl |
| A1.179 | $CH_3$ | S | C—Br | $CH_2OCH_3$ | $CH_2$ | C—Cl |
| A1.180 | $CH_3$ | S | C—Br | $CH_2OCH_2CH_3$ | $CH_2$ | C—Cl |
| A1.181 | $CH_2CH_3$ | S | C—Cl | H | $CH_2$ | C—Cl |
| A1.182 | $CH_2CH_3$ | S | C—Cl | $CH_2CH_3$ | $CH_2$ | C—Cl |
| A1.183 | $CH_2CH_3$ | S | C—Cl | $CH_2C=CH_2$ | $CH_2$ | C—Cl |
| A1.184 | $CH_2CH_3$ | S | C—Cl | $CH_2C.CH$ | $CH_2$ | C—Cl |
| A1.185 | $CH_2CH_3$ | S | C—Cl | $CH_2OCH_3$ | $CH_2$ | C—Cl |
| A1.186 | $CH_2CH_3$ | S | C—Cl | $CH_2OCH_2CH_3$ | $CH_2$ | C—Cl |
| A1.187 | $CH_2CH_3$ | S | C—Br | H | $CH_2$ | C—Cl |
| A1.188 | $CH_2CH_3$ | S | C—Br | $CH_2CH_3$ | $CH_2$ | C—Cl |
| A1.189 | $CH_2CH_3$ | S | C—Br | $CH_2C=CH_2$ | $CH_2$ | C—Cl |
| A1.190 | $CH_2CH_3$ | S | C—Br | $CH_2C.CH$ | $CH_2$ | C—Cl |
| A1.191 | $CH_2CH_3$ | S | C—Br | $CH_2OCH_3$ | $CH_2$ | C—Cl |
| A1.192 | $CH_2CH_3$ | S | C—Br | $CH_2OCH_2CH_3$ | $CH_2$ | C—Cl |
| A1.193 | $CH_3$ | S | C—Cl | H | $CH(CH_3)$ | C—H |
| A1.194 | $CH_3$ | S | C—Cl | $CH_2CH_3$ | $CH(CH_3)$ | C—H |
| A1.195 | $CH_3$ | S | C—Cl | $CH_2C=CH_2$ | $CH(CH_3)$ | C—H |
| A1.196 | $CH_3$ | S | C—Cl | $CH_2C.CH$ | $CH(CH_3)$ | C—H |
| A1.197 | $CH_3$ | S | C—Cl | $CH_2OCH_3$ | $CH(CH_3)$ | C—H |
| A1.198 | $CH_3$ | S | C—Cl | $CH_2OCH_2CH_3$ | $CH(CH_3)$ | C—H |
| A1.199 | $CH_3$ | S | C—Br | H | $CH(CH_3)$ | C—H |
| A1.200 | $CH_3$ | S | C—Br | $CH_2CH_3$ | $CH(CH_3)$ | C—H |
| A1.201 | $CH_3$ | S | C—Br | $CH_2C=CH_2$ | $CH(CH_3)$ | C—H |
| A1.202 | $CH_3$ | S | C—Br | $CH_2C.CH$ | $CH(CH_3)$ | C—H |
| A1.203 | $CH_3$ | S | C—Br | $CH_2OCH_3$ | $CH(CH_3)$ | C—H |
| A1.204 | $CH_3$ | S | C—Br | $CH_2OCH_2CH_3$ | $CH(CH_3)$ | C—H |
| A1.205 | $CH_2CH_3$ | S | C—Cl | H | $CH(CH_3)$ | C—H |
| A1.206 | $CH_2CH_3$ | S | C—Cl | $CH_2CH_3$ | $CH(CH_3)$ | C—H |
| A1.207 | $CH_2CH_3$ | S | C—Cl | $CH_2C=CH_2$ | $CH(CH_3)$ | C—H |
| A1.208 | $CH_2CH_3$ | S | C—Cl | $CH_2C.CH$ | $CH(CH_3)$ | C—H |
| A1.209 | $CH_2CH_3$ | S | C—Cl | $CH_2OCH_3$ | $CH(CH_3)$ | C—H |
| A1.210 | $CH_2CH_3$ | S | C—Cl | $CH_2OCH_2CH_3$ | $CH(CH_3)$ | C—H |
| A1.211 | $CH_2CH_3$ | S | C—Br | H | $CH(CH_3)$ | C—H |
| A1.212 | $CH_2CH_3$ | S | C—Br | $CH_2CH_3$ | $CH(CH_3)$ | C—H |
| A1.213 | $CH_2CH_3$ | S | C—Br | $CH_2C=CH_2$ | $CH(CH_3)$ | C—H |
| A1.214 | $CH_2CH_3$ | S | C—Br | $CH_2C.CH$ | $CH(CH_3)$ | C—H |
| A1.215 | $CH_2CH_3$ | S | C—Br | $CH_2OCH_3$ | $CH(CH_3)$ | C—H |
| A1.216 | $CH_2CH_3$ | S | C—Br | $CH_2OCH_2CH_3$ | $CH(CH_3)$ | C—H |

TABLE A1-continued

Table A1 provides 432 compounds of Formula A1 wherein $R^1$, D, E, $R^{11}$, A and J are as defined in Table A1 and $R^6$ is methyl.

(A1)

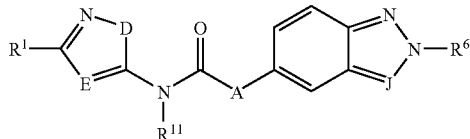

| Compound No. | $R^1$ | D | E | $R^{11}$ | A | J |
|---|---|---|---|---|---|---|
| A1.217 | $CH_3$ | S | C—Cl | H | $CH(CH_3)$ | C—Cl |
| A1.218 | $CH_3$ | S | C—Cl | $CH_2CH_3$ | $CH(CH_3)$ | C—Cl |
| A1.219 | $CH_3$ | S | C—Cl | $CH_2C=CH_2$ | $CH(CH_3)$ | C—Cl |
| A1.220 | $CH_3$ | S | C—Cl | $CH_2C.CH$ | $CH(CH_3)$ | C—Cl |
| A1.221 | $CH_3$ | S | C—Cl | $CH_2OCH_3$ | $CH(CH_3)$ | C—Cl |
| A1.222 | $CH_3$ | S | C—Cl | $CH_2OCH_2CH_3$ | $CH(CH_3)$ | C—Cl |
| A1.223 | $CH_3$ | S | C—Br | H | $CH(CH_3)$ | C—Cl |
| A1.224 | $CH_3$ | S | C—Br | $CH_2CH_3$ | $CH(CH_3)$ | C—Cl |
| A1.225 | $CH_3$ | S | C—Br | $CH_2C=CH_2$ | $CH(CH_3)$ | C—Cl |
| A1.226 | $CH_3$ | S | C—Br | $CH_2C.CH$ | $CH(CH_3)$ | C—Cl |
| A1.227 | $CH_3$ | S | C—Br | $CH_2OCH_3$ | $CH(CH_3)$ | C—Cl |
| A1.228 | $CH_3$ | S | C—Br | $CH_2OCH_2CH_3$ | $CH(CH_3)$ | C—Cl |
| A1.229 | $CH_2CH_3$ | S | C—Cl | H | $CH(CH_3)$ | C—Cl |
| A1.230 | $CH_2CH_3$ | S | C—Cl | $CH_2CH_3$ | $CH(CH_3)$ | C—Cl |
| A1.231 | $CH_2CH_3$ | S | C—Cl | $CH_2C=CH_2$ | $CH(CH_3)$ | C—Cl |
| A1.232 | $CH_2CH_3$ | S | C—Cl | $CH_2C.CH$ | $CH(CH_3)$ | C—Cl |
| A1.233 | $CH_2CH_3$ | S | C—Cl | $CH_2OCH_3$ | $CH(CH_3)$ | C—Cl |
| A1.234 | $CH_2CH_3$ | S | C—Cl | $CH_2OCH_2CH_3$ | $CH(CH_3)$ | C—Cl |
| A1.235 | $CH_2CH_3$ | S | C—Br | H | $CH(CH_3)$ | C—Cl |
| A1.236 | $CH_2CH_3$ | S | C—Br | $CH_2CH_3$ | $CH(CH_3)$ | C—Cl |
| A1.237 | $CH_2CH_3$ | S | C—Br | $CH_2C=CH_2$ | $CH(CH_3)$ | C—Cl |
| A1.238 | $CH_2CH_3$ | S | C—Br | $CH_2C.CH$ | $CH(CH_3)$ | C—Cl |
| A1.239 | $CH_2CH_3$ | S | C—Br | $CH_2OCH_3$ | $CH(CH_3)$ | C—Cl |
| A1.240 | $CH_2CH_3$ | S | C—Br | $CH_2OCH_2CH_3$ | $CH(CH_3)$ | C—Cl |
| A1.241 | $CH_3$ | S | C—Cl | H | CHF | C—H |
| A1.242 | $CH_3$ | S | C—Cl | $CH_2CH_3$ | CHF | C—H |
| A1.243 | $CH_3$ | S | C—Cl | $CH_2C=CH_2$ | CHF | C—H |
| A1.244 | $CH_3$ | S | C—Cl | $CH_2C.CH$ | CHF | C—H |
| A1.245 | $CH_3$ | S | C—Cl | $CH_2OCH_3$ | CHF | C—H |
| A1.246 | $CH_3$ | S | C—Cl | $CH_2OCH_2CH_3$ | CHF | C—H |
| A1.247 | $CH_3$ | S | C—Br | H | CHF | C—H |
| A1.248 | $CH_3$ | S | C—Br | $CH_2CH_3$ | CHF | C—H |
| A1.249 | $CH_3$ | S | C—Br | $CH_2C=CH_2$ | CHF | C—H |
| A1.250 | $CH_3$ | S | C—Br | $CH_2C.CH$ | CHF | C—H |
| A1.251 | $CH_3$ | S | C—Br | $CH_2OCH_3$ | CHF | C—H |
| A1.252 | $CH_3$ | S | C—Br | $CH_2OCH_2CH_3$ | CHF | C—H |
| A1.253 | $CH_2CH_3$ | S | C—Cl | H | CHF | C—H |
| A1.254 | $CH_2CH_3$ | S | C—Cl | $CH_2CH_3$ | CHF | C—H |
| A1.255 | $CH_2CH_3$ | S | C—Cl | $CH_2C=CH_2$ | CHF | C—H |
| A1.256 | $CH_2CH_3$ | S | C—Cl | $CH_2C.CH$ | CHF | C—H |
| A1.257 | $CH_2CH_3$ | S | C—Cl | $CH_2OCH_3$ | CHF | C—H |
| A1.258 | $CH_2CH_3$ | S | C—Cl | $CH_2OCH_2CH_3$ | CHF | C—H |
| A1.259 | $CH_2CH_3$ | S | C—Br | H | CHF | C—H |
| A1.260 | $CH_2CH_3$ | S | C—Br | $CH_2CH_3$ | CHF | C—H |
| A1.261 | $CH_2CH_3$ | S | C—Br | $CH_2C=CH_2$ | CHF | C—H |
| A1.262 | $CH_2CH_3$ | S | C—Br | $CH_2C.CH$ | CHF | C—H |
| A1.263 | $CH_2CH_3$ | S | C—Br | $CH_2OCH_3$ | CHF | C—H |
| A1.264 | $CH_2CH_3$ | S | C—Br | $CH_2OCH_2CH_3$ | CHF | C—H |
| A1.265 | $CH_3$ | S | C—Cl | H | CHF | C—Cl |
| A1.266 | $CH_3$ | S | C—Cl | $CH_2CH_3$ | CHF | C—Cl |
| A1.267 | $CH_3$ | S | C—Cl | $CH_2C=CH_2$ | CHF | C—Cl |
| A1.268 | $CH_3$ | S | C—Cl | $CH_2C.CH$ | CHF | C—Cl |
| A1.269 | $CH_3$ | S | C—Cl | $CH_2OCH_3$ | CHF | C—Cl |
| A1.270 | $CH_3$ | S | C—Cl | $CH_2OCH_2CH_3$ | CHF | C—Cl |
| A1.271 | $CH_3$ | S | C—Br | H | CHF | C—Cl |
| A1.272 | $CH_3$ | S | C—Br | $CH_2CH_3$ | CHF | C—Cl |
| A1.273 | $CH_3$ | S | C—Br | $CH_2C=CH_2$ | CHF | C—Cl |
| A1.274 | $CH_3$ | S | C—Br | $CH_2C.CH$ | CHF | C—Cl |
| A1.275 | $CH_3$ | S | C—Br | $CH_2OCH_3$ | CHF | C—Cl |
| A1.276 | $CH_3$ | S | C—Br | $CH_2OCH_2CH_3$ | CHF | C—Cl |
| A1.277 | $CH_2CH_3$ | S | C—Cl | H | CHF | C—Cl |
| A1.278 | $CH_2CH_3$ | S | C—Cl | $CH_2CH_3$ | CHF | C—Cl |
| A1.279 | $CH_2CH_3$ | S | C—Cl | $CH_2C=CH_2$ | CHF | C—Cl |
| A1.280 | $CH_2CH_3$ | S | C—Cl | $CH_2C.CH$ | CHF | C—Cl |
| A1.281 | $CH_2CH_3$ | S | C—Cl | $CH_2OCH_3$ | CHF | C—Cl |

TABLE A1-continued

Table A1 provides 432 compounds of Formula A1 wherein $R^1$, D, E, $R^{11}$, A and J are as defined in Table A1 and $R^6$ is methyl.

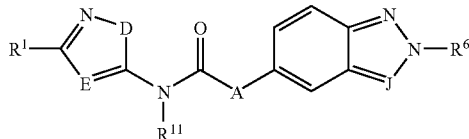

(A1)

| Compound No. | $R^1$ | D | E | $R^{11}$ | A | J |
|---|---|---|---|---|---|---|
| A1.282 | $CH_2CH_3$ | S | C—Cl | $CH_2OCH_2CH_3$ | CHF | C—Cl |
| A1.283 | $CH_2CH_3$ | S | C—Br | H | CHF | C—Cl |
| A1.284 | $CH_2CH_3$ | S | C—Br | $CH_2CH_3$ | CHF | C—Cl |
| A1.285 | $CH_2CH_3$ | S | C—Br | $CH_2C=CH_2$ | CHF | C—Cl |
| A1.286 | $CH_2CH_3$ | S | C—Br | $CH_2C.CH$ | CHF | C—Cl |
| A1.287 | $CH_2CH_3$ | S | C—Br | $CH_2OCH_3$ | CHF | C—Cl |
| A1.288 | $CH_2CH_3$ | S | C—Br | $CH_2OCH_2CH_3$ | CHF | C—Cl |
| A1.289 | $CH_3$ | S | C—Cl | H | $CH_2O$ | C—H |
| A1.290 | $CH_3$ | S | C—Cl | $CH_2CH_3$ | $CH_2O$ | C—H |
| A1.291 | $CH_3$ | S | C—Cl | $CH_2C=CH_2$ | $CH_2O$ | C—H |
| A1.292 | $CH_3$ | S | C—Cl | $CH_2C.CH$ | $CH_2O$ | C—H |
| A1.293 | $CH_3$ | S | C—Cl | $CH_2OCH_3$ | $CH_2O$ | C—H |
| A1.294 | $CH_3$ | S | C—Cl | $CH_2OCH_2CH_3$ | $CH_2O$ | C—H |
| A1.295 | $CH_3$ | S | C—Br | H | $CH_2O$ | C—H |
| A1.296 | $CH_3$ | S | C—Br | $CH_2CH_3$ | $CH_2O$ | C—H |
| A1.297 | $CH_3$ | S | C—Br | $CH_2C=CH_2$ | $CH_2O$ | C—H |
| A1.298 | $CH_3$ | S | C—Br | $CH_2C.CH$ | $CH_2O$ | C—H |
| A1.299 | $CH_3$ | S | C—Br | $CH_2OCH_3$ | $CH_2O$ | C—H |
| A1.300 | $CH_3$ | S | C—Br | $CH_2OCH_2CH_3$ | $CH_2O$ | C—H |
| A1.301 | $CH_2CH_3$ | S | C—Cl | H | $CH_2O$ | C—H |
| A1.302 | $CH_2CH_3$ | S | C—Cl | $CH_2CH_3$ | $CH_2O$ | C—H |
| A1.303 | $CH_2CH_3$ | S | C—Cl | $CH_2C=CH_2$ | $CH_2O$ | C—H |
| A1.304 | $CH_2CH_3$ | S | C—Cl | $CH_2C.CH$ | $CH_2O$ | C—H |
| A1.305 | $CH_2CH_3$ | S | C—Cl | $CH_2OCH_3$ | $CH_2O$ | C—H |
| A1.306 | $CH_2CH_3$ | S | C—Cl | $CH_2OCH_2CH_3$ | $CH_2O$ | C—H |
| A1.307 | $CH_2CH_3$ | S | C—Br | H | $CH_2O$ | C—H |
| A1.308 | $CH_2CH_3$ | S | C—Br | $CH_2CH_3$ | $CH_2O$ | C—H |
| A1.309 | $CH_2CH_3$ | S | C—Br | $CH_2C=CH_2$ | $CH_2O$ | C—H |
| A1.310 | $CH_2CH_3$ | S | C—Br | $CH_2C.CH$ | $CH_2O$ | C—H |
| A1.311 | $CH_2CH_3$ | S | C—Br | $CH_2OCH_3$ | $CH_2O$ | C—H |
| A1.312 | $CH_2CH_3$ | S | C—Br | $CH_2OCH_2CH_3$ | $CH_2O$ | C—H |
| A1.313 | $CH_3$ | S | C—Cl | H | $CH_2O$ | C—H |
| A1.314 | $CH_3$ | S | C—Cl | $CH_2CH_3$ | $CH_2O$ | C—H |
| A1.315 | $CH_3$ | S | C—Cl | $CH_2C=CH_2$ | $CH_2O$ | C—H |
| A1.316 | $CH_3$ | S | C—Cl | $CH_2C.CH$ | $CH_2O$ | C—H |
| A1.317 | $CH_3$ | S | C—Cl | $CH_2OCH_3$ | $CH_2O$ | C—H |
| A1.318 | $CH_3$ | S | C—Cl | $CH_2OCH_2CH_3$ | $CH_2O$ | C—H |
| A1.319 | $CH_3$ | S | C—Br | H | $CH_2O$ | C—H |
| A1.320 | $CH_3$ | S | C—Br | $CH_2CH_3$ | $CH_2O$ | C—H |
| A1.321 | $CH_3$ | S | C—Br | $CH_2C=CH_2$ | $CH_2O$ | C—H |
| A1.322 | $CH_3$ | S | C—Br | $CH_2C.CH$ | $CH_2O$ | C—H |
| A1.323 | $CH_3$ | S | C—Br | $CH_2OCH_3$ | $CH_2O$ | C—H |
| A1.324 | $CH_3$ | S | C—Br | $CH_2OCH_2CH_3$ | $CH_2O$ | C—H |
| A1.325 | $CH_2CH_3$ | S | C—Cl | H | $CH_2O$ | C—Cl |
| A1.326 | $CH_2CH_3$ | S | C—Cl | $CH_2CH_3$ | $CH_2O$ | C—Cl |
| A1.327 | $CH_2CH_3$ | S | C—Cl | $CH_2C=CH_2$ | $CH_2O$ | C—Cl |
| A1.328 | $CH_2CH_3$ | S | C—Cl | $CH_2C.CH$ | $CH_2O$ | C—Cl |
| A1.329 | $CH_2CH_3$ | S | C—Cl | $CH_2OCH_3$ | $CH_2O$ | C—Cl |
| A1.330 | $CH_2CH_3$ | S | C—Cl | $CH_2OCH_2CH_3$ | $CH_2O$ | C—Cl |
| A1.331 | $CH_2CH_3$ | S | C—Br | H | $CH_2O$ | C—Cl |
| A1.332 | $CH_2CH_3$ | S | C—Br | $CH_2CH_3$ | $CH_2O$ | C—Cl |
| A1.333 | $CH_2CH_3$ | S | C—Br | $CH_2C=CH_2$ | $CH_2O$ | C—Cl |
| A1.334 | $CH_2CH_3$ | S | C—Br | $CH_2C.CH$ | $CH_2O$ | C—Cl |
| A1.335 | $CH_2CH_3$ | S | C—Br | $CH_2OCH_3$ | $CH_2O$ | C—Cl |
| A1.336 | $CH_2CH_3$ | S | C—Br | $CH_2OCH_2CH_3$ | $CH_2O$ | C—Cl |
| A1.337 | $CH_3$ | CH=CH | C—Cl | H | $CH_2$ | C—H |
| A1.338 | $CH_3$ | CH=CH | C—Cl | $CH_2CH_3$ | $CH_2$ | C—H |
| A1.339 | $CH_3$ | CH=CH | C—Cl | $CH_2C=CH_2$ | $CH_2$ | C—H |
| A1.340 | $CH_3$ | CH=CH | C—Cl | $CH_2C.CH$ | $CH_2$ | C—H |
| A1.341 | $CH_3$ | CH=CH | C—Cl | $CH_2OCH_3$ | $CH_2$ | C—H |
| A1.342 | $CH_3$ | CH=CH | C—Cl | $CH_2OCH_2CH_3$ | $CH_2$ | C—H |
| A1.343 | $CH_2CH_3$ | CH=CH | C—Cl | H | $CH_2$ | C—H |
| A1.344 | $CH_2CH_3$ | CH=CH | C—Cl | $CH_2CH_3$ | $CH_2$ | C—H |
| A1.345 | $CH_2CH_3$ | CH=CH | C—Cl | $CH_2C=CH_2$ | $CH_2$ | C—H |
| A1.346 | $CH_2CH_3$ | CH=CH | C—Cl | $CH_2C.CH$ | $CH_2$ | C—H |

TABLE A1-continued

Table A1 provides 432 compounds of Formula A1 wherein $R^1$, D, E, $R^{11}$, A and J are as defined in Table A1 and $R^6$ is methyl.

(A1)

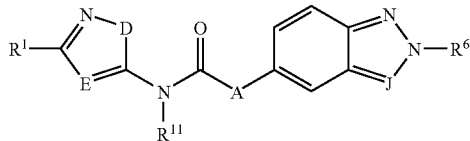

| Compound No. | $R^1$ | D | E | $R^{11}$ | A | J |
|---|---|---|---|---|---|---|
| A1.347 | $CH_2CH_3$ | CH=CH | C—Cl | $CH_2OCH_3$ | $CH_2$ | C—H |
| A1.348 | $CH_2CH_3$ | CH=CH | C—Cl | $CH_2OCH_2CH_3$ | $CH_2$ | C—H |
| A1.349 | $CH_3$ | CH=CH | C—Cl | H | $CH_2$ | C—Cl |
| A1.350 | $CH_3$ | CH=CH | C—Cl | $CH_2CH_3$ | $CH_2$ | C—Cl |
| A1.351 | $CH_3$ | CH=CH | C—Cl | $CH_2C=CH_2$ | $CH_2$ | C—Cl |
| A1.352 | $CH_3$ | CH=CH | C—Cl | $CH_2C.CH$ | $CH_2$ | C—Cl |
| A1.353 | $CH_3$ | CH=CH | C—Cl | $CH_2OCH_3$ | $CH_2$ | C—Cl |
| A1.354 | $CH_3$ | CH=CH | C—Cl | $CH_2OCH_2CH_3$ | $CH_2$ | C—Cl |
| A1.355 | $CH_2CH_3$ | CH=CH | C—Cl | H | $CH_2$ | C—Cl |
| A1.356 | $CH_2CH_3$ | CH=CH | C—Cl | $CH_2CH_3$ | $CH_2$ | C—Cl |
| A1.357 | $CH_2CH_3$ | CH=CH | C—Cl | $CH_2C=CH_2$ | $CH_2$ | C—Cl |
| A1.358 | $CH_2CH_3$ | CH=CH | C—Cl | $CH_2C.CH$ | $CH_2$ | C—Cl |
| A1.359 | $CH_2CH_3$ | CH=CH | C—Cl | $CH_2OCH_3$ | $CH_2$ | C—Cl |
| A1.360 | $CH_2CH_3$ | CH=CH | C—Cl | $CH_2OCH_2CH_3$ | $CH_2$ | C—Cl |
| A1.361 | $CH_3$ | CH=CH | C—Cl | H | $CH(CH_3)$ | C—H |
| A1.362 | $CH_3$ | CH=CH | C—Cl | $CH_2CH_3$ | $CH(CH_3)$ | C—H |
| A1.363 | $CH_3$ | CH=CH | C—Cl | $CH_2C=CH_2$ | $CH(CH_3)$ | C—H |
| A1.364 | $CH_3$ | CH=CH | C—Cl | $CH_2C.CH$ | $CH(CH_3)$ | C—H |
| A1.365 | $CH_3$ | CH=CH | C—Cl | $CH_2OCH_3$ | $CH(CH_3)$ | C—H |
| A1.366 | $CH_3$ | CH=CH | C—Cl | $CH_2OCH_2CH_3$ | $CH(CH_3)$ | C—H |
| A1.367 | $CH_2CH_3$ | CH=CH | C—Cl | H | $CH(CH_3)$ | C—H |
| A1.368 | $CH_2CH_3$ | CH=CH | C—Cl | $CH_2CH_3$ | $CH(CH_3)$ | C—H |
| A1.369 | $CH_2CH_3$ | CH=CH | C—Cl | $CH_2C=CH_2$ | $CH(CH_3)$ | C—H |
| A1.370 | $CH_2CH_3$ | CH=CH | C—Cl | $CH_2C.CH$ | $CH(CH_3)$ | C—H |
| A1.371 | $CH_2CH_3$ | CH=CH | C—Cl | $CH_2OCH_3$ | $CH(CH_3)$ | C—H |
| A1.372 | $CH_2CH_3$ | CH=CH | C—Cl | $CH_2OCH_2CH_3$ | $CH(CH_3)$ | C—H |
| A1.373 | $CH_3$ | CH=CH | C—Cl | H | $CH(CH_3)$ | C—Cl |
| A1.374 | $CH_3$ | CH=CH | C—Cl | $CH_2CH_3$ | $CH(CH_3)$ | C—Cl |
| A1.375 | $CH_3$ | CH=CH | C—Cl | $CH_2C=CH_2$ | $CH(CH_3)$ | C—Cl |
| A1.376 | $CH_3$ | CH=CH | C—Cl | $CH_2C.CH$ | $CH(CH_3)$ | C—Cl |
| A1.377 | $CH_3$ | CH=CH | C—Cl | $CH_2OCH_3$ | $CH(CH_3)$ | C—Cl |
| A1.378 | $CH_3$ | CH=CH | C—Cl | $CH_2OCH_2CH_3$ | $CH(CH_3)$ | C—Cl |
| A1.379 | $CH_2CH_3$ | CH=CH | C—Cl | H | $CH(CH_3)$ | C—Cl |
| A1.380 | $CH_2CH_3$ | CH=CH | C—Cl | $CH_2CH_3$ | $CH(CH_3)$ | C—Cl |
| A1.381 | $CH_2CH_3$ | CH=CH | C—Cl | $CH_2C=CH_2$ | $CH(CH_3)$ | C—Cl |
| A1.382 | $CH_2CH_3$ | CH=CH | C—Cl | $CH_2C.CH$ | $CH(CH_3)$ | C—Cl |
| A1.383 | $CH_2CH_3$ | CH=CH | C—Cl | $CH_2OCH_3$ | $CH(CH_3)$ | C—Cl |
| A1.384 | $CH_2CH_3$ | CH=CH | C—Cl | $CH_2OCH_2CH_3$ | $CH(CH_3)$ | C—Cl |
| A1.385 | $CH_3$ | CH=CH | C—Cl | H | CHF | C—H |
| A1.386 | $CH_3$ | CH=CH | C—Cl | $CH_2CH_3$ | CHF | C—H |
| A1.387 | $CH_3$ | CH=CH | C—Cl | $CH_2C=CH_2$ | CHF | C—H |
| A1.388 | $CH_3$ | CH=CH | C—Cl | $CH_2C.CH$ | CHF | C—H |
| A1.389 | $CH_3$ | CH=CH | C—Cl | $CH_2OCH_3$ | CHF | C—H |
| A1.390 | $CH_3$ | CH=CH | C—Cl | $CH_2OCH_2CH_3$ | CHF | C—H |
| A1.391 | $CH_2CH_3$ | CH=CH | C—Cl | H | CHF | C—H |
| A1.392 | $CH_2CH_3$ | CH=CH | C—Cl | $CH_2CH_3$ | CHF | C—H |
| A1.393 | $CH_2CH_3$ | CH=CH | C—Cl | $CH_2C=CH_2$ | CHF | C—H |
| A1.394 | $CH_2CH_3$ | CH=CH | C—Cl | $CH_2C.CH$ | CHF | C—H |
| A1.395 | $CH_2CH_3$ | CH=CH | C—Cl | $CH_2OCH_3$ | CHF | C—H |
| A1.396 | $CH_2CH_3$ | CH=CH | C—Cl | $CH_2OCH_2CH_3$ | CHF | C—H |
| A1.397 | $CH_3$ | CH=CH | C—Cl | H | CHF | C—Cl |
| A1.398 | $CH_3$ | CH=CH | C—Cl | $CH_2CH_3$ | CHF | C—Cl |
| A1.399 | $CH_3$ | CH=CH | C—Cl | $CH_2C=CH_2$ | CHF | C—Cl |
| A1.400 | $CH_3$ | CH=CH | C—Cl | $CH_2C.CH$ | CHF | C—Cl |
| A1.401 | $CH_3$ | CH=CH | C—Cl | $CH_2OCH_3$ | CHF | C—Cl |
| A1.402 | $CH_3$ | CH=CH | C—Cl | $CH_2OCH_2CH_3$ | CHF | C—Cl |
| A1.403 | $CH_2CH_3$ | CH=CH | C—Cl | H | CHF | C—Cl |
| A1.404 | $CH_2CH_3$ | CH=CH | C—Cl | $CH_2CH_3$ | CHF | C—Cl |
| A1.405 | $CH_2CH_3$ | CH=CH | C—Cl | $CH_2C=CH_2$ | CHF | C—Cl |
| A1.406 | $CH_2CH_3$ | CH=CH | C—Cl | $CH_2C.CH$ | CHF | C—Cl |
| A1.407 | $CH_2CH_3$ | CH=CH | C—Cl | $CH_2OCH_3$ | CHF | C—Cl |
| A1.408 | $CH_2CH_3$ | CH=CH | C—Cl | $CH_2OCH_2CH_3$ | CHF | C—Cl |
| A1.409 | $CH_3$ | CH=CH | C—Cl | H | $CH_2O$ | C—H |
| A1.410 | $CH_3$ | CH=CH | C—Cl | $CH_2CH_3$ | $CH_2O$ | C—H |
| A1.411 | $CH_3$ | CH=CH | C—Cl | $CH_2C=CH_2$ | $CH_2O$ | C—H |

TABLE A1-continued

Table A1 provides 432 compounds of Formula A1 wherein $R^1$, D, E, $R^{11}$, A and J are as defined in Table A1 and $R^6$ is methyl.

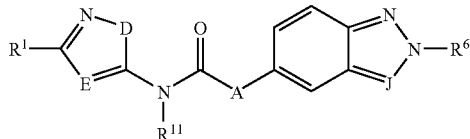

(A1)

| Compound No. | $R^1$ | D | E | $R^{11}$ | A | J |
|---|---|---|---|---|---|---|
| A1.412 | $CH_3$ | CH=CH | C—Cl | $CH_2C.CH$ | $CH_2O$ | C—H |
| A1.413 | $CH_3$ | CH=CH | C—Cl | $CH_2OCH_3$ | $CH_2O$ | C—H |
| A1.414 | $CH_3$ | CH=CH | C—Cl | $CH_2OCH_2CH_3$ | $CH_2O$ | C—H |
| A1.415 | $CH_2CH_3$ | CH=CH | C—Cl | H | $CH_2O$ | C—H |
| A1.416 | $CH_2CH_3$ | CH=CH | C—Cl | $CH_2CH_3$ | $CH_2O$ | C—H |
| A1.417 | $CH_2CH_3$ | CH=CH | C—Cl | $CH_2C=CH_2$ | $CH_2O$ | C—H |
| A1.418 | $CH_2CH_3$ | CH=CH | C—Cl | $CH_2C.CH$ | $CH_2O$ | C—H |
| A1.419 | $CH_2CH_3$ | CH=CH | C—Cl | $CH_2OCH_3$ | $CH_2O$ | C—H |
| A1.420 | $CH_2CH_3$ | CH=CH | C—Cl | $CH_2OCH_2CH_3$ | $CH_2O$ | C—H |
| A1.421 | $CH_3$ | CH=CH | C—Cl | H | $CH_2O$ | C—Cl |
| A1.422 | $CH_3$ | CH=CH | C—Cl | $CH_2CH_3$ | $CH_2O$ | C—Cl |
| A1.423 | $CH_3$ | CH=CH | C—Cl | $CH_2C=CH_2$ | $CH_2O$ | C—Cl |
| A1.424 | $CH_3$ | CH=CH | C—Cl | $CH_2C.CH$ | $CH_2O$ | C—Cl |
| A1.425 | $CH_3$ | CH=CH | C—Cl | $CH_2OCH_3$ | $CH_2O$ | C—Cl |
| A1.426 | $CH_3$ | CH=CH | C—Cl | $CH_2OCH_2CH_3$ | $CH_2O$ | C—Cl |
| A1.427 | $CH_2CH_3$ | CH=CH | C—Cl | H | $CH_2O$ | C—Cl |
| A1.428 | $CH_2CH_3$ | CH=CH | C—Cl | $CH_2CH_3$ | $CH_2O$ | C—Cl |
| A1.429 | $CH_2CH_3$ | CH=CH | C—Cl | $CH_2C=CH_2$ | $CH_2O$ | C—Cl |
| A1.430 | $CH_2CH_3$ | CH=CH | C—Cl | $CH_2C.CH$ | $CH_2O$ | C—Cl |
| A1.431 | $CH_2CH_3$ | CH=CH | C—Cl | $CH_2OCH_3$ | $CH_2O$ | C—Cl |
| A1.432 | $CH_2CH_3$ | CH=CH | C—Cl | $CH_2OCH_2CH_3$ | $CH_2O$ | C—Cl |

Table A2

Table A2 provides 432 compounds of Formula A1 wherein $R^1$, D, E, $R^{11}$, A and J are as defined in Table A1 and $R^6$ is ethyl.

Table A3

Table A3 provides 432 compounds of Formula A1 wherein $R^1$, D, E, $R^{11}$, A and J are as defined in Table A1 and $R^6$ is n-propyl.

Table A4

Table A4 provides 432 compounds of Formula A1 wherein $R^1$, D, E, $R^{11}$, A and J are as defined in Table A1 and $R^6$ is iso-propyl.

Table A5

Table A5 provides 432 compounds of Formula A1 wherein $R^1$, D, E, $R^{11}$, A and J are as defined in Table A1 and $R^6$ is n-butyl.

Table A6

Table A6 provides 432 compounds of Formula A1 wherein $R^1$, D, E, $R^{11}$, A and J are as defined in Table A1 and $R^6$ is sec-butyl.

Table A7

Table A7 provides 432 compounds of Formula A1 wherein $R^1$, D, E, $R^{11}$, A and J are as defined in Table A1 and $R^6$ is iso-butyl.

Table A8

Table A8 provides 432 compounds of Formula A1 wherein $R^1$, D, E, $R^{11}$, A and J are as defined in Table A1 and $R^6$ is tert-butyl.

Table A9

Table A9 provides 432 compounds of Formula A1 wherein $R^1$, D, E, $R^{11}$, A and J are as defined in Table A1 and $R^6$ is n-pentyl.

Table A10

Table A10 provides 432 compounds of Formula A1 wherein $R^1$, D, E, $R^{11}$, A and J are as defined in Table A1 and $R^6$ is 1-methylbutyl.

Table A11

Table A11 provides 432 compounds of Formula A1 wherein $R^1$, D, E, $R^{11}$, A and J are as defined in Table A1 and $R^6$ is 2-methylbutyl.

Table A12

Table A12 provides 432 compounds of Formula A1 wherein $R^1$, D, E, $R^{11}$, A and J are as defined in Table A1 and $R^6$ is 3-methylbutyl.

Table A13

Table A13 provides 432 compounds of Formula A1 wherein $R^1$, D, E, $R^{11}$, A and J are as defined in Table A1 and $R^6$ is neopentyl.

Table A14

Table A14 provides 432 compounds of Formula A1 wherein $R^1$, D, E, $R^{11}$, A and J are as defined in Table A1 and $R^6$ is 2,2-dimethylbutyl.

Table A15

Table A15 provides 432 compounds of Formula A1 wherein $R^1$, D, E, $R^{11}$, A and J are as defined in Table A1 and $R^6$ is 2,2,2-trifluoroethyl.

Table A16

Table A16 provides 432 compounds of Formula A1 wherein $R^1$, D, E, $R^{11}$, A and J are as defined in Table A1 and $R^6$ is 2,2-difluoro-2-methoxyethyl.

Table A17

Table A17 provides 432 compounds of Formula A1 wherein $R^1$, D, E, $R^{11}$, A and J are as defined in Table A1 and $R^6$ is 3,3,3-trifluoropropyl.

Table A18

Table A18 provides 432 compounds of Formula A1 wherein $R^1$, D, E, $R^{11}$, A and J are as defined in Table A1 and $R^6$ is para-fluorobenzyl.

Table A19

Table A19 provides 432 compounds of Formula A1 wherein $R^1$, D, E, $R^{11}$, A and J are as defined in Table A1 and $R^6$ is 2,4-dichlorophenyl.

Table A20

Table A20 provides 432 compounds of Formula A1 wherein $R^1$, D, E, $R^{11}$, A and J are as defined in Table A1 and $R^6$ is 2-chloro-4-trifluoromethylphenyl.

Table A21

Table A21 provides 432 compounds of Formula A1 wherein $R^1$, D, E, $R^{11}$, A and J are as defined in Table A1 and $R^6$ is 4-trifluoromethylphenyl.

TABLE B1

Table B1 provides 288 compounds of Formula B1 wherein $R^1$, D, E, $R^{11}$, A and J are as defined in Table B1 and $R^6$ is methyl.

(B1)

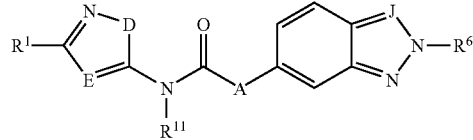

| Compound No. | $R^1$ | D | E | $R^{11}$ | A | J |
|---|---|---|---|---|---|---|
| B1.1 | $CH_3$ | S | C—Cl | H | $CH_2$ | C—H |
| B1.2 | $CH_3$ | S | C—Cl | $CH_2CH_3$ | $CH_2$ | C—H |
| B1.3 | $CH_3$ | S | C—Cl | $CH_2C=CH_2$ | $CH_2$ | C—H |
| B1.4 | $CH_3$ | S | C—Cl | $CH_2C.CH$ | $CH_2$ | C—H |
| B1.5 | $CH_3$ | S | C—Cl | $CH_2OCH_3$ | $CH_2$ | C—H |
| B1.6 | $CH_3$ | S | C—Cl | $CH_2OCH_2CH_3$ | $CH_2$ | C—H |
| B1.7 | $CH_3$ | S | C—Br | H | $CH_2$ | C—H |
| B1.8 | $CH_3$ | S | C—Br | $CH_2CH_3$ | $CH_2$ | C—H |
| B1.9 | $CH_3$ | S | C—Br | $CH_2C=CH_2$ | $CH_2$ | C—H |
| B1.10 | $CH_3$ | S | C—Br | $CH_2C.CH$ | $CH_2$ | C—H |
| B1.11 | $CH_3$ | S | C—Br | $CH_2OCH_3$ | $CH_2$ | C—H |
| B1.12 | $CH_3$ | S | C—Br | $CH_2OCH_2CH_3$ | $CH_2$ | C—H |
| B1.13 | $CH_2CH_3$ | S | C—Cl | H | $CH_2$ | C—H |
| B1.14 | $CH_2CH_3$ | S | C—Cl | $CH_2CH_3$ | $CH_2$ | C—H |
| B1.15 | $CH_2CH_3$ | S | C—Cl | $CH_2C=CH_2$ | $CH_2$ | C—H |
| B1.16 | $CH_2CH_3$ | S | C—Cl | $CH_2C.CH$ | $CH_2$ | C—H |
| B1.17 | $CH_2CH_3$ | S | C—Cl | $CH_2OCH_3$ | $CH_2$ | C—H |
| B1.18 | $CH_2CH_3$ | S | C—Cl | $CH_2OCH_2CH_3$ | $CH_2$ | C—H |
| B1.19 | $CH_2CH_3$ | S | C—Br | H | $CH_2$ | C—H |
| B1.20 | $CH_2CH_3$ | S | C—Br | $CH_2CH_3$ | $CH_2$ | C—H |
| B1.21 | $CH_2CH_3$ | S | C—Br | $CH_2C=CH_2$ | $CH_2$ | C—H |
| B1.22 | $CH_2CH_3$ | S | C—Br | $CH_2C.CH$ | $CH_2$ | C—H |
| B1.23 | $CH_2CH_3$ | S | C—Br | $CH_2OCH_3$ | $CH_2$ | C—H |
| B1.24 | $CH_2CH_3$ | S | C—Br | $CH_2OCH_2CH_3$ | $CH_2$ | C—H |
| B1.25 | $CH_3$ | S | C—Cl | H | $CH(CH_3)$ | C—H |
| B1.26 | $CH_3$ | S | C—Cl | $CH_2CH_3$ | $CH(CH_3)$ | C—H |
| B1.27 | $CH_3$ | S | C—Cl | $CH_2C=CH_2$ | $CH(CH_3)$ | C—H |
| B1.28 | $CH_3$ | S | C—Cl | $CH_2C.CH$ | $CH(CH_3)$ | C—H |
| B1.29 | $CH_3$ | S | C—Cl | $CH_2OCH_3$ | $CH(CH_3)$ | C—H |
| B1.30 | $CH_3$ | S | C—Cl | $CH_2OCH_2CH_3$ | $CH(CH_3)$ | C—H |
| B1.31 | $CH_3$ | S | C—Br | H | $CH(CH_3)$ | C—H |
| B1.32 | $CH_3$ | S | C—Br | $CH_2CH_3$ | $CH(CH_3)$ | C—H |
| B1.33 | $CH_3$ | S | C—Br | $CH_2C=CH_2$ | $CH(CH_3)$ | C—H |
| B1.34 | $CH_3$ | S | C—Br | $CH_2C.CH$ | $CH(CH_3)$ | C—H |
| B1.35 | $CH_3$ | S | C—Br | $CH_2OCH_3$ | $CH(CH_3)$ | C—H |
| B1.36 | $CH_3$ | S | C—Br | $CH_2OCH_2CH_3$ | $CH(CH_3)$ | C—H |

TABLE B1-continued

Table B1 provides 288 compounds of Formula B1 wherein $R^1$, D, E, $R^{11}$, A and J are as defined in Table B1 and $R^6$ is methyl.

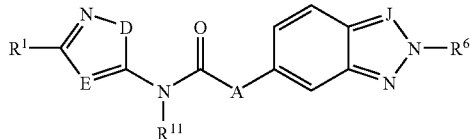

(B1)

| Compound No. | $R^1$ | D | E | $R^{11}$ | A | J |
|---|---|---|---|---|---|---|
| B1.37 | $CH_2CH_3$ | S | C—Cl | H | $CH(CH_3)$ | C—H |
| B1.38 | $CH_2CH_3$ | S | C—Cl | $CH_2CH_3$ | $CH(CH_3)$ | C—H |
| B1.39 | $CH_2CH_3$ | S | C—Cl | $CH_2C$=$CH_2$ | $CH(CH_3)$ | C—H |
| B1.40 | $CH_2CH_3$ | S | C—Cl | $CH_2C.CH$ | $CH(CH_3)$ | C—H |
| B1.41 | $CH_2CH_3$ | S | C—Cl | $CH_2OCH_3$ | $CH(CH_3)$ | C—H |
| B1.42 | $CH_2CH_3$ | S | C—Cl | $CH_2OCH_2CH_3$ | $CH(CH_3)$ | C—H |
| B1.43 | $CH_2CH_3$ | S | C—Br | H | $CH(CH_3)$ | C—H |
| B1.44 | $CH_2CH_3$ | S | C—Br | $CH_2CH_3$ | $CH(CH_3)$ | C—H |
| B1.45 | $CH_2CH_3$ | S | C—Br | $CH_2C$=$CH_2$ | $CH(CH_3)$ | C—H |
| B1.46 | $CH_2CH_3$ | S | C—Br | $CH_2C.CH$ | $CH(CH_3)$ | C—H |
| B1.47 | $CH_2CH_3$ | S | C—Br | $CH_2OCH_3$ | $CH(CH_3)$ | C—H |
| B1.48 | $CH_2CH_3$ | S | C—Br | $CH_2OCH_2CH_3$ | $CH(CH_3)$ | C—H |
| B1.49 | $CH_3$ | S | C—Cl | H | CHF | C—H |
| B1.50 | $CH_3$ | S | C—Cl | $CH_2CH_3$ | CHF | C—H |
| B1.51 | $CH_3$ | S | C—Cl | $CH_2C$=$CH_2$ | CHF | C—H |
| B1.52 | $CH_3$ | S | C—Cl | $CH_2C.CH$ | CHF | C—H |
| B1.53 | $CH_3$ | S | C—Cl | $CH_2OCH_3$ | CHF | C—H |
| B1.54 | $CH_3$ | S | C—Cl | $CH_2OCH_2CH_3$ | CHF | C—H |
| B1.55 | $CH_3$ | S | C—Br | H | CHF | C—H |
| B1.56 | $CH_3$ | S | C—Br | $CH_2CH_3$ | CHF | C—H |
| B1.57 | $CH_3$ | S | C—Br | $CH_2C$=$CH_2$ | CHF | C—H |
| B1.58 | $CH_3$ | S | C—Br | $CH_2C.CH$ | CHF | C—H |
| B1.59 | $CH_3$ | S | C—Br | $CH_2OCH_3$ | CHF | C—H |
| B1.60 | $CH_3$ | S | C—Br | $CH_2OCH_2CH_3$ | CHF | C—H |
| B1.61 | $CH_2CH_3$ | S | C—Cl | H | CHF | C—H |
| B1.62 | $CH_2CH_3$ | S | C—Cl | $CH_2CH_3$ | CHF | C—H |
| B1.63 | $CH_2CH_3$ | S | C—Cl | $CH_2C$=$CH_2$ | CHF | C—H |
| B1.64 | $CH_2CH_3$ | S | C—Cl | $CH_2C.CH$ | CHF | C—H |
| B1.65 | $CH_2CH_3$ | S | C—Cl | $CH_2OCH_3$ | CHF | C—H |
| B1.66 | $CH_2CH_3$ | S | C—Cl | $CH_2OCH_2CH_3$ | CHF | C—H |
| B1.67 | $CH_2CH_3$ | S | C—Br | H | CHF | C—H |
| B1.68 | $CH_2CH_3$ | S | C—Br | $CH_2CH_3$ | CHF | C—H |
| B1.69 | $CH_2CH_3$ | S | C—Br | $CH_2C$=$CH_2$ | CHF | C—H |
| B1.70 | $CH_2CH_3$ | S | C—Br | $CH_2C.CH$ | CHF | C—H |
| B1.71 | $CH_2CH_3$ | S | C—Br | $CH_2OCH_3$ | CHF | C—H |
| B1.72 | $CH_2CH_3$ | S | C—Br | $CH_2OCH_2CH_3$ | CHF | C—H |
| B1.73 | $CH_3$ | S | C—Cl | H | $CH_2O$ | C—H |
| B1.74 | $CH_3$ | S | C—Cl | $CH_2CH_3$ | $CH_2O$ | C—H |
| B1.75 | $CH_3$ | S | C—Cl | $CH_2C$=$CH_2$ | $CH_2O$ | C—H |
| B1.76 | $CH_3$ | S | C—Cl | $CH_2C.CH$ | $CH_2O$ | C—H |
| B1.77 | $CH_3$ | S | C—Cl | $CH_2OCH_3$ | $CH_2O$ | C—H |
| B1.78 | $CH_3$ | S | C—Cl | $CH_2OCH_2CH_3$ | $CH_2O$ | C—H |
| B1.79 | $CH_3$ | S | C—Br | H | $CH_2O$ | C—H |
| B1.80 | $CH_3$ | S | C—Br | $CH_2CH_3$ | $CH_2O$ | C—H |
| B1.81 | $CH_3$ | S | C—Br | $CH_2C$=$CH_2$ | $CH_2O$ | C—H |
| B1.82 | $CH_3$ | S | C—Br | $CH_2C.CH$ | $CH_2O$ | C—H |
| B1.83 | $CH_3$ | S | C—Br | $CH_2OCH_3$ | $CH_2O$ | C—H |
| B1.84 | $CH_3$ | S | C—Br | $CH_2OCH_2CH_3$ | $CH_2O$ | C—H |
| B1.85 | $CH_2CH_3$ | S | C—Cl | H | $CH_2O$ | C—H |
| B1.86 | $CH_2CH_3$ | S | C—Cl | $CH_2CH_3$ | $CH_2O$ | C—H |
| B1.87 | $CH_2CH_3$ | S | C—Cl | $CH_2C$=$CH_2$ | $CH_2O$ | C—H |
| B1.88 | $CH_2CH_3$ | S | C—Cl | $CH_2C.CH$ | $CH_2O$ | C—H |
| B1.89 | $CH_2CH_3$ | S | C—Cl | $CH_2OCH_3$ | $CH_2O$ | C—H |
| B1.90 | $CH_2CH_3$ | S | C—Cl | $CH_2OCH_2CH_3$ | $CH_2O$ | C—H |
| B1.91 | $CH_2CH_3$ | S | C—Br | H | $CH_2O$ | C—H |
| B1.92 | $CH_2CH_3$ | S | C—Br | $CH_2CH_3$ | $CH_2O$ | C—H |
| B1.93 | $CH_2CH_3$ | S | C—Br | $CH_2C$=$CH_2$ | $CH_2O$ | C—H |
| B1.94 | $CH_2CH_3$ | S | C—Br | $CH_2C.CH$ | $CH_2O$ | C—H |
| B1.95 | $CH_2CH_3$ | S | C—Br | $CH_2OCH_3$ | $CH_2O$ | C—H |
| B1.96 | $CH_2CH_3$ | S | C—Br | $CH_2OCH_2CH_3$ | $CH_2O$ | C—H |
| B1.97 | $CH_3$ | S | C—Cl | H | $CH_2$ | C—Cl |
| B1.98 | $CH_3$ | S | C—Cl | $CH_2CH_3$ | $CH_2$ | C—Cl |
| B1.99 | $CH_3$ | S | C—Cl | $CH_2C$=$CH_2$ | $CH_2$ | C—Cl |
| B1.100 | $CH_3$ | S | C—Cl | $CH_2C.CH$ | $CH_2$ | C—Cl |
| B1.101 | $CH_3$ | S | C—Cl | $CH_2OCH_3$ | $CH_2$ | C—Cl |

TABLE B1-continued

Table B1 provides 288 compounds of Formula B1 wherein $R^1$, D, E, $R^{11}$, A and J are as defined in Table B1 and $R^6$ is methyl.

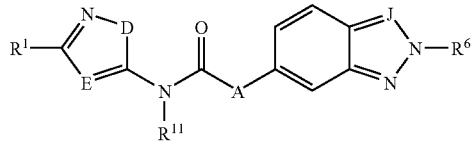

(B1)

| Compound No. | $R^1$ | D | E | $R^{11}$ | A | J |
|---|---|---|---|---|---|---|
| B1.102 | CH$_3$ | S | C—Cl | CH$_2$OCH$_2$CH$_3$ | CH$_2$ | C—Cl |
| B1.103 | CH$_3$ | S | C—Br | H | CH$_2$ | C—Cl |
| B1.104 | CH$_3$ | S | C—Br | CH$_2$CH$_3$ | CH$_2$ | C—Cl |
| B1.105 | CH$_3$ | S | C—Br | CH$_2$C═CH$_2$ | CH$_2$ | C—Cl |
| B1.106 | CH$_3$ | S | C—Br | CH$_2$C.CH | CH$_2$ | C—Cl |
| B1.107 | CH$_3$ | S | C—Br | CH$_2$OCH$_3$ | CH$_2$ | C—Cl |
| B1.108 | CH$_3$ | S | C—Br | CH$_2$OCH$_2$CH$_3$ | CH$_2$ | C—Cl |
| B1.109 | CH$_2$CH$_3$ | S | C—Cl | H | CH$_2$ | C—Cl |
| B1.110 | CH$_2$CH$_3$ | S | C—Cl | CH$_2$CH$_3$ | CH$_2$ | C—Cl |
| B1.111 | CH$_2$CH$_3$ | S | C—Cl | CH$_2$C═CH$_2$ | CH$_2$ | C—Cl |
| B1.112 | CH$_2$CH$_3$ | S | C—Cl | CH$_2$C.CH | CH$_2$ | C—Cl |
| B1.113 | CH$_2$CH$_3$ | S | C—Cl | CH$_2$OCH$_3$ | CH$_2$ | C—Cl |
| B1.114 | CH$_2$CH$_3$ | S | C—Cl | CH$_2$OCH$_2$CH$_3$ | CH$_2$ | C—Cl |
| B1.115 | CH$_2$CH$_3$ | S | C—Br | H | CH$_2$ | C—Cl |
| B1.116 | CH$_2$CH$_3$ | S | C—Br | CH$_2$CH$_3$ | CH$_2$ | C—Cl |
| B1.117 | CH$_2$CH$_3$ | S | C—Br | CH$_2$C═CH$_2$ | CH$_2$ | C—Cl |
| B1.118 | CH$_2$CH$_3$ | S | C—Br | CH$_2$C.CH | CH$_2$ | C—Cl |
| B1.119 | CH$_2$CH$_3$ | S | C—Br | CH$_2$OCH$_3$ | CH$_2$ | C—Cl |
| B1.120 | CH$_2$CH$_3$ | S | C—Br | CH$_2$OCH$_2$CH$_3$ | CH$_2$ | C—Cl |
| B1.121 | CH$_3$ | S | C—Cl | H | CH(CH$_3$) | C—Cl |
| B1.122 | CH$_3$ | S | C—Cl | CH$_2$CH$_3$ | CH(CH$_3$) | C—Cl |
| B1.123 | CH$_3$ | S | C—Cl | CH$_2$C═CH$_2$ | CH(CH$_3$) | C—Cl |
| B1.124 | CH$_3$ | S | C—Cl | CH$_2$C.CH | CH(CH$_3$) | C—Cl |
| B1.125 | CH$_3$ | S | C—Cl | CH$_2$OCH$_3$ | CH(CH$_3$) | C—Cl |
| B1.126 | CH$_3$ | S | C—Cl | CH$_2$OCH$_2$CH$_3$ | CH(CH$_3$) | C—Cl |
| B1.127 | CH$_3$ | S | C—Br | H | CH(CH$_3$) | C—Cl |
| B1.128 | CH$_3$ | S | C—Br | CH$_2$CH$_3$ | CH(CH$_3$) | C—Cl |
| B1.129 | CH$_3$ | S | C—Br | CH$_2$C═CH$_2$ | CH(CH$_3$) | C—Cl |
| B1.130 | CH$_3$ | S | C—Br | CH$_2$C.CH | CH(CH$_3$) | C—Cl |
| B1.131 | CH$_3$ | S | C—Br | CH$_2$OCH$_3$ | CH(CH$_3$) | C—Cl |
| B1.132 | CH$_3$ | S | C—Br | CH$_2$OCH$_2$CH$_3$ | CH(CH$_3$) | C—Cl |
| B1.133 | CH$_2$CH$_3$ | S | C—Cl | H | CH(CH$_3$) | C—Cl |
| B1.134 | CH$_2$CH$_3$ | S | C—Cl | CH$_2$CH$_3$ | CH(CH$_3$) | C—Cl |
| B1.135 | CH$_2$CH$_3$ | S | C—Cl | CH$_2$C═CH$_2$ | CH(CH$_3$) | C—Cl |
| B1.136 | CH$_2$CH$_3$ | S | C—Cl | CH$_2$C.CH | CH(CH$_3$) | C—Cl |
| B1.137 | CH$_2$CH$_3$ | S | C—Cl | CH$_2$OCH$_3$ | CH(CH$_3$) | C—Cl |
| B1.138 | CH$_2$CH$_3$ | S | C—Cl | CH$_2$OCH$_2$CH$_3$ | CH(CH$_3$) | C—Cl |
| B1.139 | CH$_2$CH$_3$ | S | C—Br | H | CH(CH$_3$) | C—Cl |
| B1.140 | CH$_2$CH$_3$ | S | C—Br | CH$_2$CH$_3$ | CH(CH$_3$) | C—Cl |
| B1.141 | CH$_2$CH$_3$ | S | C—Br | CH$_2$C═CH$_2$ | CH(CH$_3$) | C—Cl |
| B1.142 | CH$_2$CH$_3$ | S | C—Br | CH$_2$C.CH | CH(CH$_3$) | C—Cl |
| B1.143 | CH$_2$CH$_3$ | S | C—Br | CH$_2$OCH$_3$ | CH(CH$_3$) | C—Cl |
| B1.144 | CH$_2$CH$_3$ | S | C—Br | CH$_2$OCH$_2$CH$_3$ | CH(CH$_3$) | C—Cl |
| B1.145 | CH$_3$ | S | C—Cl | H | CHF | C—Cl |
| B1.146 | CH$_3$ | S | C—Cl | CH$_2$CH$_3$ | CHF | C—Cl |
| B1.147 | CH$_3$ | S | C—Cl | CH$_2$C═CH$_2$ | CHF | C—Cl |
| B1.148 | CH$_3$ | S | C—Cl | CH$_2$C.CH | CHF | C—Cl |
| B1.149 | CH$_3$ | S | C—Cl | CH$_2$OCH$_3$ | CHF | C—Cl |
| B1.150 | CH$_3$ | S | C—Cl | CH$_2$OCH$_2$CH$_3$ | CHF | C—Cl |
| B1.151 | CH$_3$ | S | C—Br | H | CHF | C—Cl |
| B1.152 | CH$_3$ | S | C—Br | CH$_2$CH$_3$ | CHF | C—Cl |
| B1.153 | CH$_3$ | S | C—Br | CH$_2$C═CH$_2$ | CHF | C—Cl |
| B1.154 | CH$_3$ | S | C—Br | CH$_2$C.CH | CHF | C—Cl |
| B1.155 | CH$_3$ | S | C—Br | CH$_2$OCH$_3$ | CHF | C—Cl |
| B1.156 | CH$_3$ | S | C—Br | CH$_2$OCH$_2$CH$_3$ | CHF | C—Cl |
| B1.157 | CH$_2$CH$_3$ | S | C—Cl | H | CHF | C—Cl |
| B1.158 | CH$_2$CH$_3$ | S | C—Cl | CH$_2$CH$_3$ | CHF | C—Cl |
| B1.159 | CH$_2$CH$_3$ | S | C—Cl | CH$_2$C═CH$_2$ | CHF | C—Cl |
| B1.160 | CH$_2$CH$_3$ | S | C—Cl | CH$_2$C.CH | CHF | C—Cl |
| B1.161 | CH$_2$CH$_3$ | S | C—Cl | CH$_2$OCH$_3$ | CHF | C—Cl |
| B1.162 | CH$_2$CH$_3$ | S | C—Cl | CH$_2$OCH$_2$CH$_3$ | CHF | C—Cl |
| B1.163 | CH$_2$CH$_3$ | S | C—Br | H | CHF | C—Cl |
| B1.164 | CH$_2$CH$_3$ | S | C—Br | CH$_2$CH$_3$ | CHF | C—Cl |
| B1.165 | CH$_2$CH$_3$ | S | C—Br | CH$_2$C═CH$_2$ | CHF | C—Cl |
| B1.166 | CH$_2$CH$_3$ | S | C—Br | CH$_2$C.CH | CHF | C—Cl |

TABLE B1-continued

Table B1 provides 288 compounds of Formula B1 wherein $R^1$, D, E, $R^{11}$, A and J are as defined in Table B1 and $R^6$ is methyl.

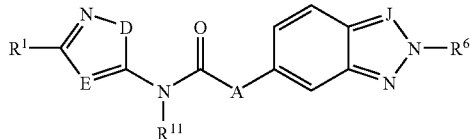

(B1)

| Compound No. | $R^1$ | D | E | $R^{11}$ | A | J |
| --- | --- | --- | --- | --- | --- | --- |
| B1.167 | $CH_2CH_3$ | S | C—Br | $CH_2OCH_3$ | CHF | C—Cl |
| B1.168 | $CH_2CH_3$ | S | C—Br | $CH_2OCH_2CH_3$ | CHF | C—Cl |
| B1.169 | $CH_3$ | S | C—Cl | H | $CH_2O$ | C—Cl |
| B1.170 | $CH_3$ | S | C—Cl | $CH_2CH_3$ | $CH_2O$ | C—Cl |
| B1.171 | $CH_3$ | S | C—Cl | $CH_2C=CH_2$ | $CH_2O$ | C—Cl |
| B1.172 | $CH_3$ | S | C—Cl | $CH_2C.CH$ | $CH_2O$ | C—Cl |
| B1.173 | $CH_3$ | S | C—Cl | $CH_2OCH_3$ | $CH_2O$ | C—Cl |
| B1.174 | $CH_3$ | S | C—Cl | $CH_2OCH_2CH_3$ | $CH_2O$ | C—Cl |
| B1.175 | $CH_3$ | S | C—Br | H | $CH_2O$ | C—Cl |
| B1.176 | $CH_3$ | S | C—Br | $CH_2CH_3$ | $CH_2O$ | C—Cl |
| B1.177 | $CH_3$ | S | C—Br | $CH_2C=CH_2$ | $CH_2O$ | C—Cl |
| B1.178 | $CH_3$ | S | C—Br | $CH_2C.CH$ | $CH_2O$ | C—Cl |
| B1.179 | $CH_3$ | S | C—Br | $CH_2OCH_3$ | $CH_2O$ | C—Cl |
| B1.180 | $CH_3$ | S | C—Br | $CH_2OCH_2CH_3$ | $CH_2O$ | C—Cl |
| B1.181 | $CH_2CH_3$ | S | C—Cl | H | $CH_2O$ | C—Cl |
| B1.182 | $CH_2CH_3$ | S | C—Cl | $CH_2CH_3$ | $CH_2O$ | C—Cl |
| B1.183 | $CH_2CH_3$ | S | C—Cl | $CH_2C=CH_2$ | $CH_2O$ | C—Cl |
| B1.184 | $CH_2CH_3$ | S | C—Cl | $CH_2C.CH$ | $CH_2O$ | C—Cl |
| B1.185 | $CH_2CH_3$ | S | C—Cl | $CH_2OCH_3$ | $CH_2O$ | C—Cl |
| B1.186 | $CH_2CH_3$ | S | C—Cl | $CH_2OCH_2CH_3$ | $CH_2O$ | C—Cl |
| B1.187 | $CH_2CH_3$ | S | C—Br | H | $CH_2O$ | C—Cl |
| B1.188 | $CH_2CH_3$ | S | C—Br | $CH_2CH_3$ | $CH_2O$ | C—Cl |
| B1.189 | $CH_2CH_3$ | S | C—Br | $CH_2C=CH_2$ | $CH_2O$ | C—Cl |
| B1.190 | $CH_2CH_3$ | S | C—Br | $CH_2C.CH$ | $CH_2O$ | C—Cl |
| B1.191 | $CH_2CH_3$ | S | C—Br | $CH_2OCH_3$ | $CH_2O$ | C—Cl |
| B1.192 | $CH_2CH_3$ | S | C—Br | $CH_2OCH_2CH_3$ | $CH_2O$ | C—Cl |
| B1.193 | $CH_3$ | CH=CH | C—Cl | H | $CH_2$ | C—H |
| B1.194 | $CH_3$ | CH=CH | C—Cl | $CH_2CH_3$ | $CH_2$ | C—H |
| B1.195 | $CH_3$ | CH=CH | C—Cl | $CH_2C=CH_2$ | $CH_2$ | C—H |
| B1.196 | $CH_3$ | CH=CH | C—Cl | $CH_2C.CH$ | $CH_2$ | C—H |
| B1.197 | $CH_3$ | CH=CH | C—Cl | $CH_2OCH_3$ | $CH_2$ | C—H |
| B1.198 | $CH_3$ | CH=CH | C—Cl | $CH_2OCH_2CH_3$ | $CH_2$ | C—H |
| B1.199 | $CH_2CH_3$ | CH=CH | C—Cl | H | $CH_2$ | C—H |
| B1.200 | $CH_2CH_3$ | CH=CH | C—Cl | $CH_2CH_3$ | $CH_2$ | C—H |
| B1.201 | $CH_2CH_3$ | CH=CH | C—Cl | $CH_2C=CH_2$ | $CH_2$ | C—H |
| B1.202 | $CH_2CH_3$ | CH=CH | C—Cl | $CH_2C.CH$ | $CH_2$ | C—H |
| B1.203 | $CH_2CH_3$ | CH=CH | C—Cl | $CH_2OCH_3$ | $CH_2$ | C—H |
| B1.204 | $CH_2CH_3$ | CH=CH | C—Cl | $CH_2OCH_2CH_3$ | $CH_2$ | C—H |
| B1.205 | $CH_3$ | CH=CH | C—Cl | H | $CH_2$ | C—Cl |
| B1.206 | $CH_3$ | CH=CH | C—Cl | $CH_2CH_3$ | $CH_2$ | C—Cl |
| B1.207 | $CH_3$ | CH=CH | C—Cl | $CH_2C=CH_2$ | $CH_2$ | C—Cl |
| B1.208 | $CH_3$ | CH=CH | C—Cl | $CH_2C.CH$ | $CH_2$ | C—Cl |
| B1.209 | $CH_3$ | CH=CH | C—Cl | $CH_2OCH_3$ | $CH_2$ | C—Cl |
| B1.210 | $CH_3$ | CH=CH | C—Cl | $CH_2OCH_2CH_3$ | $CH_2$ | C—Cl |
| B1.211 | $CH_2CH_3$ | CH=CH | C—Cl | H | $CH_2$ | C—Cl |
| B1.212 | $CH_2CH_3$ | CH=CH | C—Cl | $CH_2CH_3$ | $CH_2$ | C—Cl |
| B1.213 | $CH_2CH_3$ | CH=CH | C—Cl | $CH_2C=CH_2$ | $CH_2$ | C—Cl |
| B1.214 | $CH_2CH_3$ | CH=CH | C—Cl | $CH_2C.CH$ | $CH_2$ | C—Cl |
| B1.215 | $CH_2CH_3$ | CH=CH | C—Cl | $CH_2OCH_3$ | $CH_2$ | C—Cl |
| B1.216 | $CH_2CH_3$ | CH=CH | C—Cl | $CH_2OCH_2CH_3$ | $CH_2$ | C—Cl |
| B1.217 | $CH_3$ | CH=CH | C—Cl | H | $CH(CH_3)$ | C—H |
| B1.218 | $CH_3$ | CH=CH | C—Cl | $CH_2CH_3$ | $CH(CH_3)$ | C—H |
| B1.219 | $CH_3$ | CH=CH | C—Cl | $CH_2C=CH_2$ | $CH(CH_3)$ | C—H |
| B1.220 | $CH_3$ | CH=CH | C—Cl | $CH_2C.CH$ | $CH(CH_3)$ | C—H |
| B1.221 | $CH_3$ | CH=CH | C—Cl | $CH_2OCH_3$ | $CH(CH_3)$ | C—H |
| B1.222 | $CH_3$ | CH=CH | C—Cl | $CH_2OCH_2CH_3$ | $CH(CH_3)$ | C—H |
| B1.223 | $CH_2CH_3$ | CH=CH | C—Cl | H | $CH(CH_3)$ | C—H |
| B1.224 | $CH_2CH_3$ | CH=CH | C—Cl | $CH_2CH_3$ | $CH(CH_3)$ | C—H |
| B1.225 | $CH_2CH_3$ | CH=CH | C—Cl | $CH_2C=CH_2$ | $CH(CH_3)$ | C—H |
| B1.226 | $CH_2CH_3$ | CH=CH | C—Cl | $CH_2C.CH$ | $CH(CH_3)$ | C—H |
| B1.227 | $CH_2CH_3$ | CH=CH | C—Cl | $CH_2OCH_3$ | $CH(CH_3)$ | C—H |
| B1.228 | $CH_2CH_3$ | CH=CH | C—Cl | $CH_2OCH_2CH_3$ | $CH(CH_3)$ | C—H |
| B1.229 | $CH_3$ | CH=CH | C—Cl | H | $CH(CH_3)$ | C—Cl |
| B1.230 | $CH_3$ | CH=CH | C—Cl | $CH_2CH_3$ | $CH(CH_3)$ | C—Cl |
| B1.231 | $CH_3$ | CH=CH | C—Cl | $CH_2C=CH_2$ | $CH(CH_3)$ | C—Cl |

TABLE B1-continued

Table B1 provides 288 compounds of Formula B1 wherein $R^1$, D, E, $R^{11}$, A and J are as defined in Table B1 and $R^6$ is methyl.

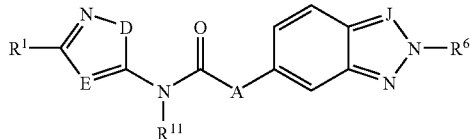

(B1)

| Compound No. | $R^1$ | D | E | $R^{11}$ | A | J |
|---|---|---|---|---|---|---|
| B1.232 | $CH_3$ | CH=CH | C—Cl | $CH_2C.CH$ | $CH(CH_3)$ | C—Cl |
| B1.233 | $CH_3$ | CH=CH | C—Cl | $CH_2OCH_3$ | $CH(CH_3)$ | C—Cl |
| B1.234 | $CH_3$ | CH=CH | C—Cl | $CH_2OCH_2CH_3$ | $CH(CH_3)$ | C—Cl |
| B1.235 | $CH_2CH_3$ | CH=CH | C—Cl | H | $CH(CH_3)$ | C—Cl |
| B1.236 | $CH_2CH_3$ | CH=CH | C—Cl | $CH_2CH_3$ | $CH(CH_3)$ | C—Cl |
| B1.237 | $CH_2CH_3$ | CH=CH | C—Cl | $CH_2C=CH_2$ | $CH(CH_3)$ | C—Cl |
| B1.238 | $CH_2CH_3$ | CH=CH | C—Cl | $CH_2C.CH$ | $CH(CH_3)$ | C—Cl |
| B1.239 | $CH_2CH_3$ | CH=CH | C—Cl | $CH_2OCH_3$ | $CH(CH_3)$ | C—Cl |
| B1.240 | $CH_2CH_3$ | CH=CH | C—Cl | $CH_2OCH_2CH_3$ | $CH(CH_3)$ | C—Cl |
| B1.241 | $CH_3$ | CH=CH | C—Cl | H | CHF | C—H |
| B1.242 | $CH_3$ | CH=CH | C—Cl | $CH_2CH_3$ | CHF | C—H |
| B1.243 | $CH_3$ | CH=CH | C—Cl | $CH_2C=CH_2$ | CHF | C—H |
| B1.244 | $CH_3$ | CH=CH | C—Cl | $CH_2C.CH$ | CHF | C—H |
| B1.245 | $CH_3$ | CH=CH | C—Cl | $CH_2OCH_3$ | CHF | C—H |
| B1.246 | $CH_3$ | CH=CH | C—Cl | $CH_2OCH_2CH_3$ | CHF | C—H |
| B1.247 | $CH_2CH_3$ | CH=CH | C—Cl | H | CHF | C—H |
| B1.248 | $CH_2CH_3$ | CH=CH | C—Cl | $CH_2CH_3$ | CHF | C—H |
| B1.249 | $CH_2CH_3$ | CH=CH | C—Cl | $CH_2C=CH_2$ | CHF | C—H |
| B1.250 | $CH_2CH_3$ | CH=CH | C—Cl | $CH_2C.CH$ | CHF | C—H |
| B1.251 | $CH_2CH_3$ | CH=CH | C—Cl | $CH_2OCH_3$ | CHF | C—H |
| B1.252 | $CH_2CH_3$ | CH=CH | C—Cl | $CH_2OCH_2CH_3$ | CHF | C—H |
| B1.253 | $CH_3$ | CH=CH | C—Cl | H | CHF | C—Cl |
| B1.254 | $CH_3$ | CH=CH | C—Cl | $CH_2CH_3$ | CHF | C—Cl |
| B1.255 | $CH_3$ | CH=CH | C—Cl | $CH_2C=CH_2$ | CHF | C—Cl |
| B1.256 | $CH_3$ | CH=CH | C—Cl | $CH_2C.CH$ | CHF | C—Cl |
| B1.257 | $CH_3$ | CH=CH | C—Cl | $CH_2OCH_3$ | CHF | C—Cl |
| B1.258 | $CH_3$ | CH=CH | C—Cl | $CH_2OCH_2CH_3$ | CHF | C—Cl |
| B1.259 | $CH_2CH_3$ | CH=CH | C—Cl | H | CHF | C—Cl |
| B1.260 | $CH_2CH_3$ | CH=CH | C—Cl | $CH_2CH_3$ | CHF | C—Cl |
| B1.261 | $CH_2CH_3$ | CH=CH | C—Cl | $CH_2C=CH_2$ | CHF | C—Cl |
| B1.262 | $CH_2CH_3$ | CH=CH | C—Cl | $CH_2C.CH$ | CHF | C—Cl |
| B1.263 | $CH_2CH_3$ | CH=CH | C—Cl | $CH_2OCH_3$ | CHF | C—Cl |
| B1.264 | $CH_2CH_3$ | CH=CH | C—Cl | $CH_2OCH_2CH_3$ | CHF | C—Cl |
| B1.265 | $CH_3$ | CH=CH | C—Cl | H | $CH_2O$ | C—H |
| B1.266 | $CH_3$ | CH=CH | C—Cl | $CH_2CH_3$ | $CH_2O$ | C—H |
| B1.267 | $CH_3$ | CH=CH | C—Cl | $CH_2C=CH_2$ | $CH_2O$ | C—H |
| B1.268 | $CH_3$ | CH=CH | C—Cl | $CH_2C.CH$ | $CH_2O$ | C—H |
| B1.269 | $CH_3$ | CH=CH | C—Cl | $CH_2OCH_3$ | $CH_2O$ | C—H |
| B1.270 | $CH_3$ | CH=CH | C—Cl | $CH_2OCH_2CH_3$ | $CH_2O$ | C—H |
| B1.271 | $CH_2CH_3$ | CH=CH | C—Cl | H | $CH_2O$ | C—H |
| B1.272 | $CH_2CH_3$ | CH=CH | C—Cl | $CH_2CH_3$ | $CH_2O$ | C—H |
| B1.273 | $CH_2CH_3$ | CH=CH | C—Cl | $CH_2C=CH_2$ | $CH_2O$ | C—H |
| B1.274 | $CH_2CH_3$ | CH=CH | C—Cl | $CH_2C.CH$ | $CH_2O$ | C—H |
| B1.275 | $CH_2CH_3$ | CH=CH | C—Cl | $CH_2OCH_3$ | $CH_2O$ | C—H |
| B1.276 | $CH_2CH_3$ | CH=CH | C—Cl | $CH_2OCH_2CH_3$ | $CH_2O$ | C—H |
| B1.277 | $CH_3$ | CH=CH | C—Cl | H | $CH_2O$ | C—Cl |
| B1.278 | $CH_3$ | CH=CH | C—Cl | $CH_2CH_3$ | $CH_2O$ | C—Cl |
| B1.279 | $CH_3$ | CH=CH | C—Cl | $CH_2C=CH_2$ | $CH_2O$ | C—Cl |
| B1.280 | $CH_3$ | CH=CH | C—Cl | $CH_2C.CH$ | $CH_2O$ | C—Cl |
| B1.281 | $CH_3$ | CH=CH | C—Cl | $CH_2OCH_3$ | $CH_2O$ | C—Cl |
| B1.282 | $CH_3$ | CH=CH | C—Cl | $CH_2OCH_2CH_3$ | $CH_2O$ | C—Cl |
| B1.283 | $CH_2CH_3$ | CH=CH | C—Cl | H | $CH_2O$ | C—Cl |
| B1.284 | $CH_2CH_3$ | CH=CH | C—Cl | $CH_2CH_3$ | $CH_2O$ | C—Cl |
| B1.285 | $CH_2CH_3$ | CH=CH | C—Cl | $CH_2C=CH_2$ | $CH_2O$ | C—Cl |
| B1.286 | $CH_2CH_3$ | CH=CH | C—Cl | $CH_2C.CH$ | $CH_2O$ | C—Cl |
| B1.287 | $CH_2CH_3$ | CH=CH | C—Cl | $CH_2OCH_3$ | $CH_2O$ | C—Cl |
| B1.288 | $CH_2CH_3$ | CH=CH | C—Cl | $CH_2OCH_2CH_3$ | $CH_2O$ | C—Cl |

Table B2

Table B2 provides 288 compounds of Formula B1 wherein $R^1$, D, E, $R^{11}$, A and J are as defined in Table B1 and $R^6$ is ethyl.

Table B3

Table B3 provides 288 compounds of Formula B1 wherein $R^1$, D, E, $R^{11}$, A and J are as defined in Table B1 and $R^6$ is n-propyl.

Table B4

Table B4 provides 288 compounds of Formula B1 wherein $R^1$, D, E, $R^{11}$, A and J are as defined in Table B1 and $R^6$ is iso-propyl.

Table B5

Table B5 provides 288 compounds of Formula B1 wherein $R^1$, D, E, $R^{11}$, A and J are as defined in Table B1 and $R^6$ is n-butyl.

Table B6

Table B6 provides 288 compounds of Formula B1 wherein $R^1$, D, E, $R^{11}$, A and J are as defined in Table B1 and $R^6$ is sec-butyl.

Table B7

Table B7 provides 288 compounds of Formula B1 wherein $R^1$, D, E, $R^{11}$, A and J are as defined in Table B1 and $R^6$ is iso-butyl.

Table B8

Table B8 provides 288 compounds of Formula B1 wherein $R^1$, D, E, $R^{11}$, A and J are as defined in Table B1 and $R^6$ is tert-butyl.

Table B9

Table B9 provides 288 compounds of Formula B1 wherein $R^1$, D, E, $R^{11}$, A and J are as defined in Table B1 and $R^6$ is n-pentyl.

Table B10

Table B10 provides 288 compounds of Formula B1 wherein $R^1$, D, E, $R^{11}$, A and J are as defined in Table B1 and $R^6$ is 1-methylbutyl.

Table B11

Table B11 provides 288 compounds of Formula B1 wherein $R^1$, D, E, $R^{11}$, A and J 40 are as defined in Table B1 and $R^6$ is 2-methylbutyl.

Table B12

Table B12 provides 288 compounds of Formula B1 wherein $R^1$, D, E, $R^{11}$, A and J are as defined in Table B1 and $R^6$ is 3-methylbutyl.

Table B13

Table B13 provides 288 compounds of Formula B1 wherein $R^1$, D, E, $R^{11}$, A and J are as defined in Table B1 and $R^6$ is neopentyl.

Table B14

Table B14 provides 288 compounds of Formula B1 wherein $R^1$, D, E, $R^{11}$, A and J are as defined in Table B1 and $R^6$ is 2,2-dimethylbutyl.

Table B15

Table B15 provides 288 compounds of Formula B1 wherein $R^1$, D, E, $R^{11}$, A and J are as defined in Table B1 and $R^6$ is 2,2,2-trifluoroethyl.

Table B16

Table B16 provides 288 compounds of Formula B1 wherein $R^1$, D, E, $R^{11}$, A and J are as defined in Table B1 and $R^6$ is 2,2-difluoro-2-methoxyethyl.

Table B17

Table B17 provides 288 compounds of Formula B1 wherein $R^1$, D, E, $R^{11}$, A and J are as defined in Table B1 and $R^6$ is 3,3,3-trifluoropropyl.

Table B18

Table B18 provides 288 compounds of Formula B1 wherein $R^1$, D, E, $R^{11}$, A and J are as defined in Table B1 and $R^6$ is para-fluorobenzyl.

Table B19

Table B19 provides 288 compounds of Formula B1 wherein $R^1$, D, E, $R^{11}$, A and J are as defined in Table B1 and $R^6$ is 2,4-dichlorophenyl.

Table B20

Table B20 provides 288 compounds of Formula B1 wherein $R^1$, D, E, $R^{11}$, A and J are as defined in Table B1 and $R^6$ is 2-chloro-4-trifluoromethylphenyl.

TABLE C1

Table C1 provides 144 compounds of Formula C1 wherein X, $R^{11}$, A and J are as defined in Table C1 and $R^6$ is methyl.

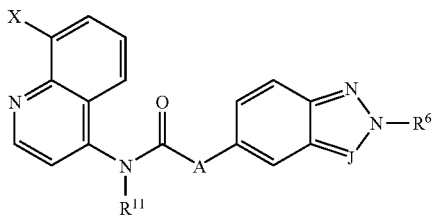

(C1)

| Compound No | X | $R^{11}$ | A | J |
|---|---|---|---|---|
| C1.1 | H | H | $CH_2$ | N |
| C1.2 | H | $CH_2CH_3$ | $CH_2$ | N |
| C1.3 | H | $CH_2C=CH_2$ | $CH_2$ | N |
| C1.4 | H | $CH_2C.CH$ | $CH_2$ | N |
| C1.5 | H | $CH_2OCH_3$ | $CH_2$ | N |
| C1.6 | H | $CH_2OCH_2CH_3$ | $CH_2$ | N |
| C1.7 | H | H | $CH(CH_3)$ | N |
| C1.8 | H | $CH_2CH_3$ | $CH(CH_3)$ | N |
| C1.9 | H | $CH_2C=CH_2$ | $CH(CH_3)$ | N |
| C1.10 | H | $CH_2C.CH$ | $CH(CH_3)$ | N |
| C1.11 | H | $CH_2OCH_3$ | $CH(CH_3)$ | N |
| C1.12 | H | $CH_2OCH_2CH_3$ | $CH(CH_3)$ | N |
| C1.13 | H | H | CHF | N |
| C1.14 | H | $CH_2CH_3$ | CHF | N |
| C1.15 | H | $CH_2C=CH_2$ | CHF | N |
| C1.16 | H | $CH_2C.CH$ | CHF | N |
| C1.17 | H | $CH_2OCH_3$ | CHF | N |
| C1.18 | H | $CH_2OCH_2CH_3$ | CHF | N |

TABLE C1-continued

Table C1 provides 144 compounds of Formula C1 wherein X, $R^{11}$, A and J are as defined in Table C1 and $R^6$ is methyl.

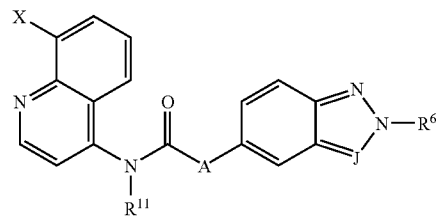
(C1)

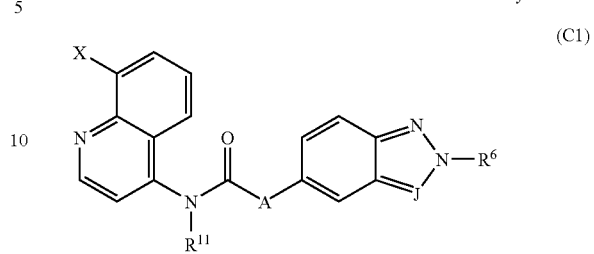
(C1)

| Compound No | X | $R^{11}$ | A | J |
|---|---|---|---|---|
| C1.19 | H | H | $CH_2O$ | N |
| C1.20 | H | $CH_2CH_3$ | $CH_2O$ | N |
| C1.21 | H | $CH_2C=CH_2$ | $CH_2O$ | N |
| C1.22 | H | $CH_2C.CH$ | $CH_2O$ | N |
| C1.23 | H | $CH_2OCH_3$ | $CH_2O$ | N |
| C1.24 | H | $CH_2OCH_2CH_3$ | $CH_2O$ | N |
| C1.25 | F | H | $CH_2$ | N |
| C1.26 | F | $CH_2CH_3$ | $CH_2$ | N |
| C1.27 | F | $CH_2C=CH_2$ | $CH_2$ | N |
| C1.28 | F | $CH_2C.CH$ | $CH_2$ | N |
| C1.29 | F | $CH_2OCH_3$ | $CH_2$ | N |
| C1.30 | F | $CH_2OCH_2CH_3$ | $CH_2$ | N |
| C1.31 | F | H | $CH(CH_3)$ | N |
| C1.32 | F | $CH_2CH_3$ | $CH(CH_3)$ | N |
| C1.33 | F | $CH_2C=CH_2$ | $CH(CH_3)$ | N |
| C1.34 | F | $CH_2C.CH$ | $CH(CH_3)$ | N |
| C1.35 | F | $CH_2OCH_3$ | $CH(CH_3)$ | N |
| C1.36 | F | $CH_2OCH_2CH_3$ | $CH(CH_3)$ | N |
| C1.37 | F | H | CHF | N |
| C1.38 | F | $CH_2CH_3$ | CHF | N |
| C1.39 | F | $CH_2C=CH_2$ | CHF | N |
| C1.40 | F | $CH_2C.CH$ | CHF | N |
| C1.41 | F | $CH_2OCH_3$ | CHF | N |
| C1.42 | F | $CH_2OCH_2CH_3$ | CHF | N |
| C1.43 | F | H | $CH_2O$ | N |
| C1.44 | F | $CH_2CH_3$ | $CH_2O$ | N |
| C1.45 | F | $CH_2C=CH_2$ | $CH_2O$ | N |
| C1.46 | F | $CH_2C.CH$ | $CH_2O$ | N |
| C1.47 | F | $CH_2OCH_3$ | $CH_2O$ | N |
| C1.48 | F | $CH_2OCH_2CH_3$ | $CH_2O$ | N |
| C1.49 | H | H | $CH_2$ | C—H |
| C1.50 | H | $CH_2CH_3$ | $CH_2$ | C—H |
| C1.51 | H | $CH_2C=CH_2$ | $CH_2$ | C—H |
| C1.52 | H | $CH_2C.CH$ | $CH_2$ | C—H |
| C1.53 | H | $CH_2OCH_3$ | $CH_2$ | C—H |
| C1.54 | H | $CH_2OCH_2CH_3$ | $CH_2$ | C—H |
| C1.55 | H | H | $CH(CH_3)$ | C—H |
| C1.56 | H | $CH_2CH_3$ | $CH(CH_3)$ | C—H |
| C1.57 | H | $CH_2C=CH_2$ | $CH(CH_3)$ | C—H |
| C1.58 | H | $CH_2C.CH$ | $CH(CH_3)$ | C—H |
| C1.59 | H | $CH_2OCH_3$ | $CH(CH_3)$ | C—H |
| C1.60 | H | $CH_2OCH_2CH_3$ | $CH(CH_3)$ | C—H |
| C1.61 | H | H | CHF | C—H |
| C1.62 | H | $CH_2CH_3$ | CHF | C—H |
| C1.63 | H | $CH_2C=CH_2$ | CHF | C—H |
| C1.64 | H | $CH_2C.CH$ | CHF | C—H |
| C1.65 | H | $CH_2OCH_3$ | CHF | C—H |
| C1.66 | H | $CH_2OCH_2CH_3$ | CHF | C—H |
| C1.67 | H | H | $CH_2O$ | C—H |
| C1.68 | H | $CH_2CH_3$ | $CH_2O$ | C—H |
| C1.69 | H | $CH_2C=CH_2$ | $CH_2O$ | C—H |
| C1.70 | H | $CH_2C.CH$ | $CH_2O$ | C—H |
| C1.71 | H | $CH_2OCH_3$ | $CH_2O$ | C—H |
| C1.72 | H | $CH_2OCH_2CH_3$ | $CH_2O$ | C—H |
| C1.73 | F | H | $CH_2$ | C—H |
| C1.74 | F | $CH_2CH_3$ | $CH_2$ | C—H |
| C1.75 | F | $CH_2C=CH_2$ | $CH_2$ | C—H |
| C1.76 | F | $CH_2C.CH$ | $CH_2$ | C—H |
| C1.77 | F | $CH_2OCH_3$ | $CH_2$ | C—H |
| C1.78 | F | $CH_2OCH_2CH_3$ | $CH_2$ | C—H |
| C1.79 | F | H | $CH(CH_3)$ | C—H |
| C1.80 | F | $CH_2CH_3$ | $CH(CH_3)$ | C—H |
| C1.81 | F | $CH_2C=CH_2$ | $CH(CH_3)$ | C—H |
| C1.82 | F | $CH_2C.CH$ | $CH(CH_3)$ | C—H |
| C1.83 | F | $CH_2OCH_3$ | $CH(CH_3)$ | C—H |
| C1.84 | F | $CH_2OCH_2CH_3$ | $CH(CH_3)$ | C—H |
| C1.85 | F | H | CHF | C—H |
| C1.86 | F | $CH_2CH_3$ | CHF | C—H |
| C1.87 | F | $CH_2C=CH_2$ | CHF | C—H |
| C1.88 | F | $CH_2C.CH$ | CHF | C—H |
| C1.89 | F | $CH_2OCH_3$ | CHF | C—H |
| C1.90 | F | $CH_2OCH_2CH_3$ | CHF | C—H |
| C1.91 | F | H | $CH_2O$ | C—H |
| C1.92 | F | $CH_2CH_3$ | $CH_2O$ | C—H |
| C1.93 | F | $CH_2C=CH_2$ | $CH_2O$ | C—H |
| C1.94 | F | $CH_2C.CH$ | $CH_2O$ | C—H |
| C1.95 | F | $CH_2OCH_3$ | $CH_2O$ | C—H |
| C1.96 | F | $CH_2OCH_2CH_3$ | $CH_2O$ | C—H |
| C1.97 | H | H | $CH_2$ | C—Cl |
| C1.98 | H | $CH_2CH_3$ | $CH_2$ | C—Cl |
| C1.99 | H | $CH_2C=CH_2$ | $CH_2$ | C—Cl |
| C1.100 | H | $CH_2C.CH$ | $CH_2$ | C—Cl |
| C1.101 | H | $CH_2OCH_3$ | $CH_2$ | C—Cl |
| C1.102 | H | $CH_2OCH_2CH_3$ | $CH_2$ | C—Cl |
| C1.103 | H | H | $CH(CH_3)$ | C—Cl |
| C1.104 | H | $CH_2CH_3$ | $CH(CH_3)$ | C—Cl |
| C1.105 | H | $CH_2C=CH_2$ | $CH(CH_3)$ | C—Cl |
| C1.106 | H | $CH_2C.CH$ | $CH(CH_3)$ | C—Cl |
| C1.107 | H | $CH_2OCH_3$ | $CH(CH_3)$ | C—Cl |
| C1.108 | H | $CH_2OCH_2CH_3$ | $CH(CH_3)$ | C—Cl |
| C1.109 | H | H | CHF | C—Cl |
| C1.110 | H | $CH_2CH_3$ | CHF | C—Cl |
| C1.111 | H | $CH_2C=CH_2$ | CHF | C—Cl |
| C1.112 | H | $CH_2C.CH$ | CHF | C—Cl |
| C1.113 | H | $CH_2OCH_3$ | CHF | C—Cl |
| C1.114 | H | $CH_2OCH_2CH_3$ | CHF | C—Cl |
| C1.115 | H | H | $CH_2O$ | C—Cl |
| C1.116 | H | $CH_2CH_3$ | $CH_2O$ | C—Cl |
| C1.117 | H | $CH_2C=CH_2$ | $CH_2O$ | C—Cl |
| C1.118 | H | $CH_2C.CH$ | $CH_2O$ | C—Cl |
| C1.119 | H | $CH_2OCH_3$ | $CH_2O$ | C—Cl |
| C1.120 | H | $CH_2OCH_2CH_3$ | $CH_2O$ | C—Cl |
| C1.121 | F | H | $CH_2$ | C—Cl |
| C1.122 | F | $CH_2CH_3$ | $CH_2$ | C—Cl |
| C1.123 | F | $CH_2C=CH_2$ | $CH_2$ | C—Cl |
| C1.124 | F | $CH_2C.CH$ | $CH_2$ | C—Cl |
| C1.125 | F | $CH_2OCH_3$ | $CH_2$ | C—Cl |
| C1.126 | F | $CH_2OCH_2CH_3$ | $CH_2$ | C—Cl |
| C1.127 | F | H | $CH(CH_3)$ | C—Cl |
| C1.128 | F | $CH_2CH_3$ | $CH(CH_3)$ | C—Cl |
| C1.129 | F | $CH_2C=CH_2$ | $CH(CH_3)$ | C—Cl |
| C1.130 | F | $CH_2C.CH$ | $CH(CH_3)$ | C—Cl |
| C1.131 | F | $CH_2OCH_3$ | $CH(CH_3)$ | C—Cl |
| C1.132 | F | $CH_2OCH_2CH_3$ | $CH(CH_3)$ | C—Cl |
| C1.133 | F | H | CHF | C—Cl |
| C1.134 | F | $CH_2CH_3$ | CHF | C—Cl |
| C1.135 | F | $CH_2C=CH_2$ | CHF | C—Cl |
| C1.136 | F | $CH_2C.CH$ | CHF | C—Cl |
| C1.137 | F | $CH_2OCH_3$ | CHF | C—Cl |
| C1.138 | F | $CH_2OCH_2CH_3$ | CHF | C—Cl |
| C1.139 | F | H | $CH_2O$ | C—Cl |
| C1.140 | F | $CH_2CH_3$ | $CH_2O$ | C—Cl |
| C1.141 | F | $CH_2C=CH_2$ | $CH_2O$ | C—Cl |
| C1.142 | F | $CH_2C.CH$ | $CH_2O$ | C—Cl |

TABLE C1-continued

Table C1 provides 144 compounds of Formula C1 wherein X, $R^{11}$, A and J are as defined in Table C1 and $R^6$ is methyl.

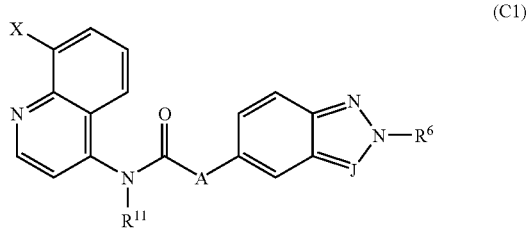

(C1)

| Compound No | X | $R^{11}$ | A | J |
|---|---|---|---|---|
| C1.143 | F | $CH_2OCH_3$ | $CH_2O$ | C—Cl |
| C1.144 | F | $CH_2OCH_2CH_3$ | $CH_2O$ | C—Cl |

Table C2

Table C2 provides 144 compounds of Formula C1 wherein X, $R^{11}$, A and J are as defined in Table C1 and $R^6$ is ethyl.

Table C3

Table C3 provides 144 compounds of Formula C1 wherein X, $R^{11}$, A and J are as defined in Table C1 and $R^6$ is n-propyl.

Table C4

Table C4 provides 144 compounds of Formula C1 wherein X, $R^{11}$, A and J are as defined in Table C1 and $R^6$ is iso-propyl.

Table C5

Table C5 provides 144 compounds of Formula C1 wherein X, $R^{11}$, A and J are as defined in Table C1 and $R^6$ is n-butyl.

Table C6

Table C6 provides 144 compounds of Formula C1 wherein X, $R^{11}$, A and J are as defined in Table C1 and $R^6$ is sec-butyl.

Table C7

Table C7 provides 144 compounds of Formula C1 wherein X, $R^{11}$, A and J are as defined in Table C1 and $R^6$ is iso-butyl.

Table C8

Table C8 provides 144 compounds of Formula C1 wherein X, $R^{11}$, A and J are as defined in Table C1 and $R^6$ is tert-butyl.

Table C9

Table C9 provides 144 compounds of Formula C1 wherein X, $R^{11}$, A and J are as defined in Table C1 and $R^6$ is n-pentyl.

Table C10

Table C10 provides 144 compounds of Formula C1 wherein X, $R^{11}$, A and J are as defined in Table C1 and $R^6$ is 1-methylbutyl.

Table C11

Table C11 provides 144 compounds of Formula C1 wherein X, $R^{11}$, A and J are as defined in Table C1 and $R^6$ is 2-methylbutyl.

Table C12

Table C12 provides 144 compounds of Formula C1 wherein X, $R^{11}$, A and J are as defined in Table C1 and $R^6$ is 3-methylbutyl.

Table C13

Table C13 provides 144 compounds of Formula C1 wherein X, $R^{11}$, A and J are as defined in Table C1 and $R^6$ is neopentyl.

Table C14

Table C14 provides 144 compounds of Formula C1 wherein X, $R^{11}$, A and J are as defined in Table C1 and $R^6$ is 2,2-dimethylbutyl.

Table C15

Table C15 provides 144 compounds of Formula C1 wherein X, $R^{11}$, A and J are as defined in Table C1 and $R^6$ is 2,2,2-trifluoroethyl.

Table C16

Table C16 provides 144 compounds of Formula C1 wherein X, $R^{11}$, A and J are as defined in Table C1 and $R^6$ is 2,2-difluoro-2-methoxyethyl.

Table C17

Table C17 provides 144 compounds of Formula C1 wherein X, $R^{11}$, A and J are as defined in Table C1 and $R^6$ is 3,3,3-trifluoropropyl.

Table C18

Table C18 provides 144 compounds of Formula C1 wherein X, $R^{11}$, A and J are as defined in Table C1 and $R^6$ is para-fluorobenzyl.

Table C19

Table C19 provides 144 compounds of Formula C1 wherein X, $R^{11}$, A and J are as defined in Table C1 and $R^6$ is 2,4-dichlorophenyl.

Table C20

Table C20 provides 144 compounds of Formula C1 wherein X, $R^{11}$, A and J are as defined in Table C1 and $R^6$ is 2-chloro-4-trifluoromethylphenyl.

TABLE D1

Table D1 provides 96 compounds of Formula D1 wherein X, $R^{11}$, A and J are as defined in Table D1 and $R^6$ is methyl.

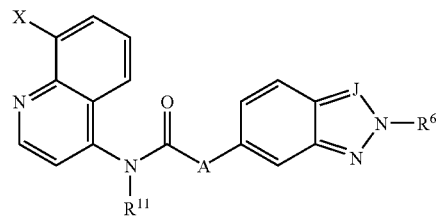

(D1)

| Compound No | X | $R^{11}$ | A | J |
|---|---|---|---|---|
| D1.1 | H | H | $CH_2$ | C—H |
| D1.2 | H | $CH_2CH_3$ | $CH_2$ | C—H |
| D1.3 | H | $CH_2C=CH_2$ | $CH_2$ | C—H |
| D1.4 | H | $CH_2C.CH$ | $CH_2$ | C—H |
| D1.5 | H | $CH_2OCH_3$ | $CH_2$ | C—H |
| D1.6 | H | $CH_2OCH_2CH_3$ | $CH_2$ | C—H |
| D1.7 | H | H | $CH(CH_3)$ | C—H |
| D1.8 | H | $CH_2CH_3$ | $CH(CH_3)$ | C—H |
| D1.9 | H | $CH_2C=CH_2$ | $CH(CH_3)$ | C—H |
| D1.10 | H | $CH_2C.CH$ | $CH(CH_3)$ | C—H |
| D1.11 | H | $CH_2OCH_3$ | $CH(CH_3)$ | C—H |
| D1.12 | H | $CH_2OCH_2CH_3$ | $CH(CH_3)$ | C—H |
| D1.13 | H | H | CHF | C—H |
| D1.14 | H | $CH_2CH_3$ | CHF | C—H |
| D1.15 | H | $CH_2C=CH_2$ | CHF | C—H |
| D1.16 | H | $CH_2C.CH$ | CHF | C—Cl |
| D1.17 | H | $CH_2OCH_3$ | CHF | C—H |
| D1.18 | H | $CH_2OCH_2CH_3$ | CHF | C—H |
| D1.19 | H | H | $CH_2O$ | C—H |
| D1.20 | H | $CH_2CH_3$ | $CH_2O$ | C—H |
| D1.21 | H | $CH_2C=CH_2$ | $CH_2O$ | C—H |
| D1.22 | H | $CH_2C.CH$ | $CH_2O$ | C—H |
| D1.23 | H | $CH_2OCH_3$ | $CH_2O$ | C—H |
| D1.24 | H | $CH_2OCH_2CH_3$ | $CH_2O$ | C—H |
| D1.25 | F | H | $CH_2$ | C—H |
| D1.26 | F | $CH_2CH_3$ | $CH_2$ | C—H |
| D1.27 | F | $CH_2C=CH_2$ | $CH_2$ | C—H |
| D1.28 | F | $CH_2C.CH$ | $CH_2$ | C—H |
| D1.29 | F | $CH_2OCH_3$ | $CH_2$ | C—H |
| D1.30 | F | $CH_2OCH_2CH_3$ | $CH_2$ | C—H |
| D1.31 | F | H | $CH(CH_3)$ | C—H |
| D1.32 | F | $CH_2CH_3$ | $CH(CH_3)$ | C—H |
| D1.33 | F | $CH_2C=CH_2$ | $CH(CH_3)$ | C—H |
| D1.34 | F | $CH_2C.CH$ | $CH(CH_3)$ | C—H |
| D1.35 | F | $CH_2OCH_3$ | $CH(CH_3)$ | C—H |
| D1.36 | F | $CH_2OCH_2CH_3$ | $CH(CH_3)$ | C—H |
| D1.37 | F | H | CHF | C—H |
| D1.38 | F | $CH_2CH_3$ | CHF | C—H |
| D1.39 | F | $CH_2C=CH_2$ | CHF | C—H |
| D1.40 | F | $CH_2C.CH$ | CHF | C—H |
| D1.41 | F | $CH_2OCH_3$ | CHF | C—H |
| D1.42 | F | $CH_2OCH_2CH_3$ | CHF | C—H |
| D1.43 | F | H | $CH_2O$ | C—H |
| D1.44 | F | $CH_2CH_3$ | $CH_2O$ | C—H |
| D1.45 | F | $CH_2C=CH_2$ | $CH_2O$ | C—H |
| D1.46 | F | $CH_2C.CH$ | $CH_2O$ | C—H |
| D1.47 | F | $CH_2OCH_3$ | $CH_2O$ | C—H |
| D1.48 | F | $CH_2OCH_2CH_3$ | $CH_2O$ | C—H |
| D1.49 | H | H | $CH_2$ | C—Cl |
| D1.50 | H | $CH_2CH_3$ | $CH_2$ | C—Cl |
| D1.51 | H | $CH_2C=CH_2$ | $CH_2$ | C—Cl |
| D1.52 | H | $CH_2C.CH$ | $CH_2$ | C—Cl |
| D1.53 | H | $CH_2OCH_3$ | $CH_2$ | C—Cl |
| D1.54 | H | $CH_2OCH_2CH_3$ | $CH_2$ | C—Cl |
| D1.55 | H | H | $CH(CH_3)$ | C—Cl |
| D1.56 | H | $CH_2CH_3$ | $CH(CH_3)$ | C—Cl |
| D1.57 | H | $CH_2C=CH_2$ | $CH(CH_3)$ | C—Cl |
| D1.58 | H | $CH_2C.CH$ | $CH(CH_3)$ | C—Cl |
| D1.59 | H | $CH_2OCH_3$ | $CH(CH_3)$ | C—Cl |
| D1.60 | H | $CH_2OCH_2CH_3$ | $CH(CH_3)$ | C—Cl |
| D1.61 | H | H | CHF | C—Cl |
| D1.62 | H | $CH_2CH_3$ | CHF | C—Cl |

TABLE D1-continued

Table D1 provides 96 compounds of Formula D1 wherein X, $R^{11}$, A and J are as defined in Table D1 and $R^6$ is methyl.

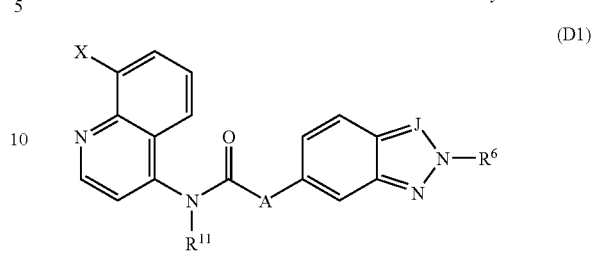

(D1)

| Compound No | X | $R^{11}$ | A | J |
|---|---|---|---|---|
| D1.63 | H | $CH_2C=CH_2$ | CHF | C—Cl |
| D1.64 | H | $CH_2C.CH$ | CHF | C—Cl |
| D1.65 | H | $CH_2OCH_3$ | CHF | C—Cl |
| D1.66 | H | $CH_2OCH_2CH_3$ | CHF | C—Cl |
| D1.67 | H | H | $CH_2O$ | C—Cl |
| D1.68 | H | $CH_2CH_3$ | $CH_2O$ | C—Cl |
| D1.69 | H | $CH_2C=CH_2$ | $CH_2O$ | C—Cl |
| D1.70 | H | $CH_2C.CH$ | $CH_2O$ | C—Cl |
| D1.71 | H | $CH_2OCH_3$ | $CH_2O$ | C—Cl |
| D1.72 | H | $CH_2OCH_2CH_3$ | $CH_2O$ | C—Cl |
| D1.73 | F | H | $CH_2$ | C—Cl |
| D1.74 | F | $CH_2CH_3$ | $CH_2$ | C—Cl |
| D1.75 | F | $CH_2C=CH_2$ | $CH_2$ | C—Cl |
| D1.76 | F | $CH_2C.CH$ | $CH_2$ | C—Cl |
| D1.77 | F | $CH_2OCH_3$ | $CH_2$ | C—Cl |
| D1.78 | F | $CH_2OCH_2CH_3$ | $CH_2$ | C—Cl |
| D1.79 | F | H | $CH(CH_3)$ | C—Cl |
| D1.80 | F | $CH_2CH_3$ | $CH(CH_3)$ | C—Cl |
| D1.81 | F | $CH_2C=CH_2$ | $CH(CH_3)$ | C—Cl |
| D1.82 | F | $CH_2C.CH$ | $CH(CH_3)$ | C—Cl |
| D1.83 | F | $CH_2OCH_3$ | $CH(CH_3)$ | C—Cl |
| D1.84 | F | $CH_2OCH_2CH_3$ | $CH(CH_3)$ | C—Cl |
| D1.85 | F | H | CHF | C—Cl |
| D1.86 | F | $CH_2CH_3$ | CHF | C—Cl |
| D1.87 | F | $CH_2C=CH_2$ | CHF | C—Cl |
| D1.88 | F | $CH_2C.CH$ | CHF | C—Cl |
| D1.89 | F | $CH_2OCH_3$ | CHF | C—Cl |
| D1.90 | F | $CH_2OCH_2CH_3$ | CHF | C—Cl |
| D1.91 | F | H | $CH_2O$ | C—Cl |
| D1.92 | F | $CH_2CH_3$ | $CH_2O$ | C—Cl |
| D1.93 | F | $CH_2C=CH_2$ | $CH_2O$ | C—Cl |
| D1.94 | F | $CH_2C.CH$ | $CH_2O$ | C—Cl |
| D1.95 | F | $CH_2OCH_3$ | $CH_2O$ | C—Cl |
| D1.96 | F | $CH_2OCH_2CH_3$ | $CH_2O$ | C—Cl |

Table D2

Table D2 provides 96 compounds of Formula D1 wherein X, $R^{11}$, A and J are as defined in Table D1 and $R^6$ is ethyl.

Table D3

Table D3 provides 96 compounds of Formula D1 wherein X, $R^{11}$, A and J are as defined in Table D1 and $R^6$ is n-propyl.

Table D4

Table D4 provides 96 compounds of Formula D1 wherein X, $R^{11}$, A and J are as defined in Table D1 and $R^6$ is iso-propyl.

Table D5

Table D5 provides 96 compounds of Formula D1 wherein X, $R^{11}$, A and J are as defined in Table D1 and $R^6$ is n-butyl.

Table D6

Table D6 provides 96 compounds of Formula D1 wherein X, $R^{11}$, A and J are as defined in Table D1 and $R^6$ is sec-butyl.

Table D7

Table D7 provides 96 compounds of Formula D1 wherein X, $R^{11}$, A and J are as defined in Table D1 and $R^6$ is iso-butyl.

Table D8

Table D8 provides 96 compounds of Formula D1 wherein X, $R^{11}$, A and J are as defined in Table D1 and $R^6$ is tert-butyl.

Table D9

Table D9 provides 96 compounds of Formula D1 wherein X, $R^{11}$, A and J are as defined in Table D1 and $R^6$ is n-pentyl.

Table D10

Table D10 provides 96 compounds of Formula D1 wherein X, $R^{11}$, A and J are as defined in Table D1 and $R^6$ is 1-methylbutyl.

Table D11

Table D11 provides 96 compounds of Formula D1 wherein X, $R^{11}$, A and J are as defined in Table D1 and $R^6$ is 2-methylbutyl.

Table D12

Table D12 provides 96 compounds of Formula D1 wherein X, $R^{11}$, A and J are as defined in Table D1 and $R^6$ is 3-methylbutyl.

Table D13

Table D13 provides 96 compounds of Formula D1 wherein X, $R^{11}$, A and J are as defined in Table D1 and $R^6$ is neopentyl.

Table D14

Table D14 provides 96 compounds of Formula D1 wherein X, $R^{11}$, A and J are as defined in Table D1 and $R^6$ is 2,2-dimethylbutyl.

Table D15

Table D15 provides 96 compounds of Formula D1 wherein X, $R^{11}$, A and J are as defined in Table D1 and $R^6$ is 2,2,2-trifluoroethyl.

Table D16

Table D16 provides 96 compounds of Formula D1 wherein X, $R^{11}$, A and J are as defined in Table D1 and $R^6$ is 2,2-difluoro-2-methoxyethyl.

Table D17

Table D17 provides 96 compounds of Formula D1 wherein X, $R^{11}$, A and J are as defined in Table D1 and $R^6$ is 3,3,3-trifluoropropyl.

Table D18

Table D18 provides 96 compounds of Formula D1 wherein X, $R^{11}$, A and J are as defined in Table D1 and $R^6$ is para-fluorobenzyl.

Table D19

Table D19 provides 96 compounds of Formula D1 wherein X, $R^{11}$, A and J are as defined in Table D1 and $R^6$ is 2,4-dichlorophenyl.

Table D20

Table D20 provides 96 compounds of Formula D1 wherein X, $R^{11}$, A and J are as defined in Table D1 and $R^6$ is 2-chloro-4-trifluoromethylphenyl.

Table E1

Table E1 provides 432 compounds of Formula E1 wherein $R^1$, D, E, $R^{11}$, A and J are as defined in Table A1 and $R^6$ is methyl.

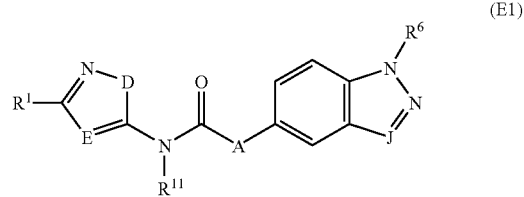

(E1)

Table E2

Table E2 provides 432 compounds of Formula E1 wherein $R^1$, D, E, $R^{11}$, A and J are as defined in Table A1 and $R^6$ is ethyl.

Table E3

Table E3 provides 432 compounds of Formula E1 wherein $R^1$, D, E, $R^{11}$, A and J are as defined in Table A1 and $R^6$ is n-propyl.

Table E4

Table E4 provides 432 compounds of Formula E1 wherein $R^1$, D, E, $R^{11}$, A and J are as defined in Table A1 and $R^6$ is iso-propyl.

Table E5

Table E5 provides 432 compounds of Formula E1 wherein $R^1$, D, E, $R^{11}$, A and J are as defined in Table A1 and $R^6$ is n-butyl.

Table E6

Table E6 provides 432 compounds of Formula E1 wherein $R^1$, D, E, $R^{11}$, A and J are as defined in Table A1 and $R^6$ is sec-butyl.

Table E7

Table E7 provides 432 compounds of Formula E1 wherein $R^1$, D, E, $R^{11}$, A and J are as defined in Table A1 and $R^6$ is iso-butyl.

Table E8

Table E8 provides 432 compounds of Formula E1 wherein $R^1$, D, E, $R^{11}$, A and J are as defined in Table A1 and $R^6$ is tert-butyl.

Table E9

Table E9 provides 432 compounds of Formula E1 wherein $R^1$, D, E, $R^{11}$, A and J are as defined in Table A1 and $R^6$ is n-pentyl.

Table E10

Table E10 provides 432 compounds of Formula E1 wherein $R^1$, D, E, $R^{11}$, A and J are as defined in Table A1 and $R^6$ is 1-methylbutyl.

Table E11

Table E11 provides 432 compounds of Formula E1 wherein $R^1$, D, E, $R^{11}$, A and J are as defined in Table A1 and $R^6$ is 2-methylbutyl.

Table E12

Table E12 provides 432 compounds of Formula E1 wherein $R^1$, D, E, $R^{11}$, A and J are as defined in Table A1 and $R^6$ is 3-methylbutyl.

Table E13

Table E13 provides 432 compounds of Formula E1 wherein $R^1$, D, E, $R^{11}$, A and J are as defined in Table A1 and $R^6$ is neopentyl.

Table E14

Table E14 provides 432 compounds of Formula E1 wherein $R^1$, D, E, $R^{11}$, A and J are as defined in Table A1 and $R^6$ is 2,2-dimethylbutyl.

Table E15

Table E15 provides 432 compounds of Formula E1 wherein $R^1$, D, E, $R^{11}$, A and J are as defined in Table A1 and $R^6$ is 2,2,2-trifluoroethyl.

Table E16

Table E16 provides 432 compounds of Formula E1 wherein $R^1$, D, E, $R^{11}$, A and J are as defined in Table A1 and $R^6$ is 2,2-difluoro-2-methoxyethyl.

Table E17

Table E17 provides 432 compounds of Formula E1 wherein $R^1$, D, E, $R^{11}$, A and J are as defined in Table A1 and $R^6$ is 3,3,3-trifluoropropyl.

Table E18

Table E18 provides 432 compounds of Formula E1 wherein $R^1$, D, E, $R^{11}$, A and J are as defined in Table A1 and $R^6$ is para-fluorobenzyl.

Table E19

Table E19 provides 432 compounds of Formula E1 wherein $R^1$, D, E, $R^{11}$, A and J are as defined in Table A1 and $R^6$ is 2,4-dichlorophenyl.

Table E20

Table E20 provides 432 compounds of Formula E1 wherein $R^1$, D, E, $R^{11}$, A and J are as defined in Table A1 and $R^6$ is 2-chloro-4-trifluoromethylphenyl.

Table E21

Table E21 provides 432 compounds of Formula E1 wherein $R^1$, D, E, $R^{11}$, A and J are as defined in Table A1 and $R^6$ is 4-trifluoromethylphenyl.

Table E22

Table E22 provides 432 compounds of Formula E1 wherein $R^1$, D, E, $R^{11}$, A and J are as defined in Table A1 and $R^6$ is $COCH_3$.

Table F1

Table F1 provides 432 compounds of Formula F1 wherein $R^1$, D, E, $R^{11}$, A and J are as defined in Table A1 and $R^6$ is methyl.

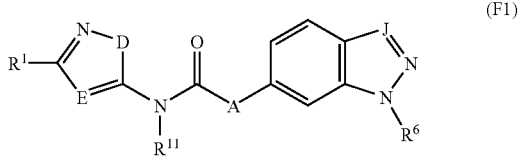

(F1)

Table F2

Table F2 provides 432 compounds of Formula F1 wherein $R^1$, D, E, $R^{11}$, A and J are as defined in Table A1 and $R^6$ is ethyl.

Table F3

Table F3 provides 432 compounds of Formula F1 wherein $R^1$, D, E, $R^{11}$, A and J are as defined in Table A1 and $R^6$ is n-propyl.

Table F4

Table F4 provides 432 compounds of Formula F1 wherein $R^1$, D, E, $R^{11}$, A and J are as defined in Table A1 and $R^6$ is iso-propyl.

Table F5

Table F5 provides 432 compounds of Formula F1 wherein $R^1$, D, E, $R^{11}$, A and J are as defined in Table A1 and $R^6$ is n-butyl.

Table F6

Table F6 provides 432 compounds of Formula F1 wherein $R^1$, D, E, $R^{11}$, A and J are as defined in Table A1 and $R^6$ is sec-butyl.

Table F7

Table F7 provides 432 compounds of Formula F1 wherein $R^1$, D, E, $R^{11}$, A and J are as defined in Table A1 and $R^6$ is iso-butyl.

Table F8

Table F8 provides 432 compounds of Formula F1 wherein $R^1$, D, E, $R^{11}$, A and J are as defined in Table A1 and $R^6$ is tert-butyl.

Table F9

Table F9 provides 432 compounds of Formula F1 wherein $R^1$, D, E, $R^{11}$, A and J are as defined in Table A1 and $R^6$ is n-pentyl.

Table F10

Table F10 provides 432 compounds of Formula F1 wherein $R^1$, D, E, $R^{11}$, A and J are as defined in Table A1 and $R^6$ is 1-methylbutyl.

Table F11

Table F11 provides 432 compounds of Formula F1 wherein $R^1$, D, E, $R^{11}$, A and J are as defined in Table A1 and $R^6$ is 2-methylbutyl.

Table F12

Table F12 provides 432 compounds of Formula F1 wherein $R^1$, D, E, $R^{11}$, A and J are as defined in Table A1 and $R^6$ is 3-methylbutyl.

Table F13

Table F13 provides 432 compounds of Formula F1 wherein $R^1$, D, E, $R^{11}$, A and J are as defined in Table A1 and $R^6$ is neopentyl.

Table F14

Table F14 provides 432 compounds of Formula F1 wherein $R^1$, D, E, $R^{11}$, A and J are as defined in Table A1 and $R^6$ is 2,2-dimethylbutyl.

Table F15

Table F15 provides 432 compounds of Formula F1 wherein $R^1$, D, E, $R^{11}$, A and J are as defined in Table A1 and $R^6$ is 2,2,2-trifluoroethyl.

Table F16

Table F16 provides 432 compounds of Formula F1 wherein $R^1$, D, E, $R^{11}$, A and J are as defined in Table A1 and $R^6$ is 2,2-difluoro-2-methoxyethyl.

Table F17

Table F17 provides 432 compounds of Formula F1 wherein $R^1$, D, E, $R^{11}$, A and J are as defined in Table A1 and $R^6$ is 3,3,3-trifluoropropyl.

Table F18

Table F18 provides 432 compounds of Formula F1 wherein $R^1$, D, E, $R^{11}$, A and J are as defined in Table A1 and $R^6$ is para-fluorobenzyl.

Table F19

Table F19 provides 432 compounds of Formula F1 wherein $R^1$, D, E, $R^{11}$, A and J are as defined in Table A1 and $R^6$ is 2,4-dichlorophenyl.

Table F20

Table F20 provides 432 compounds of Formula F1 wherein $R^1$, D, E, $R^{11}$, A and J are as defined in Table A1 and $R^6$ is 2-chloro-4-trifluoromethylphenyl.

Table F21

Table F21 provides 432 compounds of Formula F1 wherein $R^1$, D, E, $R^{11}$, A and J are as defined in Table A1 and $R^6$ is 4-trifluoromethylphenyl.

Table F22

Table F22 provides 432 compounds of Formula F1 wherein $R^1$, D, E, $R^{11}$, A and J are as defined in Table A1 and $R^6$ is $COCH_3$.

Table G1

Table G1 provides 144 compounds of Formula G1 wherein X, $R^{11}$, A and J are as defined in Table C1 and $R^6$ is methyl.

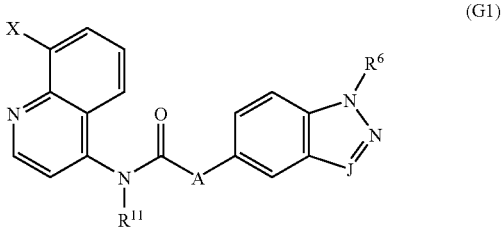

(G1)

Table G2

Table G2 provides 144 compounds of Formula G1 wherein X, $R^{11}$, A and J are as defined in Table C1 and $R^6$ is ethyl.

Table G3

Table G3 provides 144 compounds of Formula G1 wherein X, $R^{11}$, A and J are as defined in Table C1 and $R^6$ is n-propyl.

Table G4

Table G4 provides 144 compounds of Formula G1 wherein X, $R^{11}$, A and J are as defined in Table C1 and $R^6$ is iso-propyl.

Table G5

Table G5 provides 144 compounds of Formula G1 wherein X, $R^{11}$, A and J are as defined in Table C1 and $R^6$ is n-butyl.

Table G6

Table G6 provides 144 compounds of Formula G1 wherein X, $R^{11}$, A and J are as defined in Table C1 and $R^6$ is sec-butyl.

Table G7

Table G7 provides 144 compounds of Formula G1 wherein X, $R^{11}$, A and J are as defined in Table C1 and $R^6$ is iso-butyl.

Table G8

Table G8 provides 144 compounds of Formula G1 wherein X, $R^{11}$, A and J are as defined in Table C1 and $R^6$ is tert-butyl.

Table G9

Table G9 provides 144 compounds of Formula G1 wherein X, $R^{11}$, A and J are as defined in Table C1 and $R^6$ is n-pentyl.

Table G10

Table G10 provides 144 compounds of Formula G1 wherein X, $R^{11}$, A and J are as defined in Table C1 and $R^6$ is 1-methylbutyl.

Table G11

Table G12 provides 144 compounds of Formula G1 wherein X, $R^{11}$, A and J are as defined in Table C1 and $R^6$ is 2-methylbutyl.

Table G12

Table G12 provides 144 compounds of Formula G1 wherein X, $R^{11}$, A and J are as defined in Table C1 and $R^6$ is 3-methylbutyl.

Table G13

Table G13 provides 144 compounds of Formula G1 wherein X, $R^{11}$, A and J are as defined in Table C1 and $R^6$ is neopentyl.

Table G14

Table G14 provides 144 compounds of Formula G1 wherein X, $R^{11}$, A and J are as defined in Table C1 and $R^6$ is 2,2-dimethylbutyl.

Table G15

Table G15 provides 144 compounds of Formula G1 wherein X, $R^{11}$, A and J are as defined in Table C1 and $R^6$ is 2,2,2-trifluoroethyl.

Table G16

Table G16 provides 144 compounds of Formula G1 wherein X, $R^{11}$, A and J are as defined in Table C1 and $R^6$ is 2,2-difluoro-2-methoxyethyl.

Table G17

Table G17 provides 144 compounds of Formula G1 wherein X, $R^{11}$, A and J are as defined in Table C1 and $R^6$ is 3,3,3-trifluoropropyl.

Table G18

Table G18 provides 144 compounds of Formula G1 wherein X, $R^{11}$, A and J are as defined in Table C1 and $R^6$ is para-fluorobenzyl.

Table G19

Table G19 provides 144 compounds of Formula G1 wherein X, $R^{11}$, A and J are as defined in Table C1 and $R^6$ is 2,4-dichlorophenyl.

Table G20

Table G20 provides 144 compounds of Formula G1 wherein X, $R^{11}$, A and J are as defined in Table C1 and $R^6$ is 2-chloro-4-trifluoromethylphenyl.

Table H1

Table H1 provides 144 compounds of Formula H1 wherein X, $R^{11}$, A and J are as defined in Table C1 and $R^6$ is methyl.

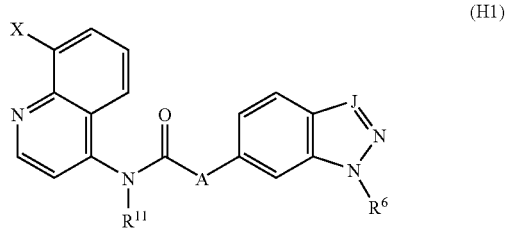

(H1)

Table H2

Table H2 provides 144 compounds of Formula H1 wherein X, $R^{11}$, A and J are as defined in Table C1 and $R^6$ is ethyl.

Table H3

Table H3 provides 144 compounds of Formula H1 wherein X, $R^{11}$, A and J are as defined in Table C1 and $R^6$ is n-propyl.

Table H4

Table H4 provides 144 compounds of Formula H1 wherein X, $R^{11}$, A and J are as defined in Table C1 and $R^6$ is iso-propyl.

Table H5

Table H5 provides 144 compounds of Formula H1 wherein X, $R^{11}$, A and J are as defined in Table C1 and $R^6$ is n-butyl.

Table H6

Table H6 provides 144 compounds of Formula H1 wherein X, $R^{11}$, A and J are as defined in Table C1 and $R^6$ is sec-butyl.

Table H7

Table H7 provides 144 compounds of Formula H1 wherein X, $R^{11}$, A and J are as defined in Table C1 and $R^6$ is iso-butyl.

Table H8

Table H8 provides 144 compounds of Formula H1 wherein X, $R^{11}$, A and J are as defined in Table C1 and $R^6$ is tert-butyl.

Table H9

Table H9 provides 144 compounds of Formula H1 wherein X, $R^{11}$, A and J are as defined in Table C1 and $R^6$ is n-pentyl.

Table H10

Table H10 provides 144 compounds of Formula H1 wherein X, $R^{11}$, A and J are as defined in Table C1 and $R^6$ is 1-methylbutyl.

Table H11

Table H11 provides 144 compounds of Formula H1 wherein X, $R^{11}$, A and J are as defined in Table C1 and $R^6$ is 2-methylbutyl.

Table H12

Table H12 provides 144 compounds of Formula H1 wherein X, $R^{11}$, A and J are as defined in Table C1 and $R^6$ is 3-methylbutyl.

Table H13

Table H13 provides 144 compounds of Formula H1 wherein X, $R^{11}$, A and J are as defined in Table C1 and $R^6$ is neopentyl.

Table H14

Table H14 provides 144 compounds of Formula H1 wherein X, $R^{11}$, A and J are as defined in Table C1 and $R^6$ is 2,2-dimethylbutyl.

Table H15

Table H15 provides 144 compounds of Formula H1 wherein X, $R^{11}$, A and J are as defined in Table C1 and $R^6$ is 2,2,2-trifluoroethyl.

Table H16

Table H16 provides 144 compounds of Formula H1 wherein X, $R^{11}$, A and J are as defined in Table C1 and $R^6$ is 2,2-difluoro-2-methoxyethyl.

Table H17

Table H17 provides 144 compounds of Formula H1 wherein X, $R^{11}$, A and J are as defined in Table C1 and $R^6$ is 3,3,3-trifluoropropyl.

Table H18

Table H18 provides 144 compounds of Formula H1 wherein X, $R^{11}$, A and J are as defined in Table C1 and $R^6$ is para-fluorobenzyl.

Table H19

Table H19 provides 144 compounds of Formula H1 wherein X, $R^{11}$, A and J are as defined in Table C1 and $R^6$ is 2,4-dichlorophenyl.

Table H20

Table H20 provides 144 compounds of Formula H1 wherein X, $R^{11}$, A and J are as defined in Table C1 and $R^6$ is 2-chloro-4-trifluoromethylphenyl.

TABLE I1

Table I1 provides 288 compounds of Formula I1, wherein $R^1$, D, E, $R^2$, A and J are as defined in Table I1 and $R^6$ is methyl.

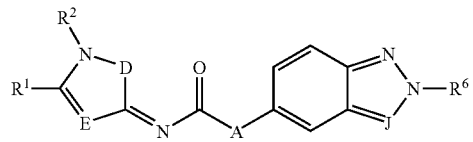

(I1)

| Compound No. | $R^1$ | D | E | $R^2$ | A | J |
|---|---|---|---|---|---|---|
| I1.1 | $CH_3$ | S | C—Cl | H | $CH_2$ | N |
| I1.2 | $CH_3$ | S | C—Cl | $CH_2CH_3$ | $CH_2$ | N |
| I1.3 | $CH_3$ | S | C—Cl | $CH_2C\!=\!CH_2$ | $CH_2$ | N |
| I1.4 | $CH_3$ | S | C—Cl | $CH_2C.CH$ | $CH_2$ | N |
| I1.5 | $CH_3$ | S | C—Cl | $CH_2OCH_3$ | $CH_2$ | N |
| I1.6 | $CH_3$ | S | C—Cl | $CH_2OCH_2CH_3$ | $CH_2$ | N |
| I1.7 | $CH_3$ | S | C—Br | H | $CH_2$ | N |
| I1.8 | $CH_3$ | S | C—Br | $CH_2CH_3$ | $CH_2$ | N |

TABLE I1-continued

Table I1 provides 288 compounds of Formula I1, wherein $R^1$, D, E, $R^2$, A and J are as defined in Table I1 and $R^6$ is methyl.

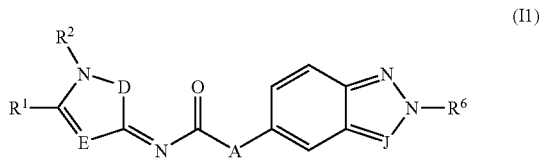

(I1)

| Compound No. | $R^1$ | D | E | $R^2$ | A | J |
|---|---|---|---|---|---|---|
| I1.9 | $CH_3$ | S | C—Br | $CH_2C=CH_2$ | $CH_2$ | N |
| I1.10 | $CH_3$ | S | C—Br | $CH_2C.CH$ | $CH_2$ | N |
| I1.11 | $CH_3$ | S | C—Br | $CH_2OCH_3$ | $CH_2$ | N |
| I1.12 | $CH_3$ | S | C—Br | $CH_2OCH_2CH_3$ | $CH_2$ | N |
| I1.13 | $CH_2CH_3$ | S | C—Cl | H | $CH_2$ | N |
| I1.14 | $CH_2CH_3$ | S | C—Cl | $CH_2CH_3$ | $CH_2$ | N |
| I1.15 | $CH_2CH_3$ | S | C—Cl | $CH_2C=CH_2$ | $CH_2$ | N |
| I1.16 | $CH_2CH_3$ | S | C—Cl | $CH_2C.CH$ | $CH_2$ | N |
| I1.17 | $CH_2CH_3$ | S | C—Cl | $CH_2OCH_3$ | $CH_2$ | N |
| I1.18 | $CH_2CH_3$ | S | C—Cl | $CH_2OCH_2CH_3$ | $CH_2$ | N |
| I1.19 | $CH_2CH_3$ | S | C—Br | H | $CH_2$ | N |
| I1.20 | $CH_2CH_3$ | S | C—Br | $CH_2CH_3$ | $CH_2$ | N |
| I1.21 | $CH_2CH_3$ | S | C—Br | $CH_2C=CH_2$ | $CH_2$ | N |
| I1.22 | $CH_2CH_3$ | S | C—Br | $CH_2C.CH$ | $CH_2$ | N |
| I1.23 | $CH_2CH_3$ | S | C—Br | $CH_2OCH_3$ | $CH_2$ | N |
| I1.24 | $CH_2CH_3$ | S | C—Br | $CH_2OCH_2CH_3$ | $CH_2$ | N |
| I1.25 | $CH_3$ | S | C—Cl | H | $CH(CH_3)$ | N |
| I1.26 | $CH_3$ | S | C—Cl | $CH_2CH_3$ | $CH(CH_3)$ | N |
| I1.27 | $CH_3$ | S | C—Cl | $CH_2C=CH_2$ | $CH(CH_3)$ | N |
| I1.28 | $CH_3$ | S | C—Cl | $CH_2C.CH$ | $CH(CH_3)$ | N |
| I1.29 | $CH_3$ | S | C—Cl | $CH_2OCH_3$ | $CH(CH_3)$ | N |
| I1.30 | $CH_3$ | S | C—Cl | $CH_2OCH_2CH_3$ | $CH(CH_3)$ | N |
| I1.31 | $CH_3$ | S | C—Br | H | $CH(CH_3)$ | N |
| I1.32 | $CH_3$ | S | C—Br | $CH_2CH_3$ | $CH(CH_3)$ | N |
| I1.33 | $CH_3$ | S | C—Br | $CH_2C=CH_2$ | $CH(CH_3)$ | N |
| I1.34 | $CH_3$ | S | C—Br | $CH_2C.CH$ | $CH(CH_3)$ | N |
| I1.35 | $CH_3$ | S | C—Br | $CH_2OCH_3$ | $CH(CH_3)$ | N |
| I1.36 | $CH_3$ | S | C—Br | $CH_2OCH_2CH_3$ | $CH(CH_3)$ | N |
| I1.37 | $CH_2CH_3$ | S | C—Cl | H | $CH(CH_3)$ | N |
| I1.38 | $CH_2CH_3$ | S | C—Cl | $CH_2CH_3$ | $CH(CH_3)$ | N |
| I1.39 | $CH_2CH_3$ | S | C—Cl | $CH_2C=CH_2$ | $CH(CH_3)$ | N |
| I1.40 | $CH_2CH_3$ | S | C—Cl | $CH_2C.CH$ | $CH(CH_3)$ | N |
| I1.41 | $CH_2CH_3$ | S | C—Cl | $CH_2OCH_3$ | $CH(CH_3)$ | N |
| I1.42 | $CH_2CH_3$ | S | C—Cl | $CH_2OCH_2CH_3$ | $CH(CH_3)$ | N |
| I1.43 | $CH_2CH_3$ | S | C—Br | H | $CH(CH_3)$ | N |
| I1.44 | $CH_2CH_3$ | S | C—Br | $CH_2CH_3$ | $CH(CH_3)$ | N |
| I1.45 | $CH_2CH_3$ | S | C—Br | $CH_2C=CH_2$ | $CH(CH_3)$ | N |
| I1.46 | $CH_2CH_3$ | S | C—Br | $CH_2C.CH$ | $CH(CH_3)$ | N |
| I1.47 | $CH_2CH_3$ | S | C—Br | $CH_2OCH_3$ | $CH(CH_3)$ | N |
| I1.48 | $CH_2CH_3$ | S | C—Br | $CH_2OCH_2CH_3$ | $CH(CH_3)$ | N |
| I1.49 | $CH_3$ | S | C—Cl | H | CHF | N |
| I1.50 | $CH_3$ | S | C—Cl | $CH_2CH_3$ | CHF | N |
| I1.51 | $CH_3$ | S | C—Cl | $CH_2C=CH_2$ | CHF | N |
| I1.52 | $CH_3$ | S | C—Cl | $CH_2C.CH$ | CHF | N |
| I1.53 | $CH_3$ | S | C—Cl | $CH_2OCH_3$ | CHF | N |
| I1.54 | $CH_3$ | S | C—Cl | $CH_2OCH_2CH_3$ | CHF | N |
| I1.55 | $CH_3$ | S | C—Br | H | CHF | N |
| I1.56 | $CH_3$ | S | C—Br | $CH_2CH_3$ | CHF | N |
| I1.57 | $CH_3$ | S | C—Br | $CH_2C=CH_2$ | CHF | N |
| I1.58 | $CH_3$ | S | C—Br | $CH_2C.CH$ | CHF | N |
| I1.59 | $CH_3$ | S | C—Br | $CH_2OCH_3$ | CHF | N |
| I1.60 | $CH_3$ | S | C—Br | $CH_2OCH_2CH_3$ | CHF | N |
| I1.61 | $CH_2CH_3$ | S | C—Cl | H | CHF | N |
| I1.62 | $CH_2CH_3$ | S | C—Cl | $CH_2CH_3$ | CHF | N |
| I1.63 | $CH_2CH_3$ | S | C—Cl | $CH_2C=CH_2$ | CHF | N |
| I1.64 | $CH_2CH_3$ | S | C—Cl | $CH_2C.CH$ | CHF | N |
| I1.65 | $CH_2CH_3$ | S | C—Cl | $CH_2OCH_3$ | CHF | N |
| I1.66 | $CH_2CH_3$ | S | C—Cl | $CH_2OCH_2CH_3$ | CHF | N |
| I1.67 | $CH_2CH_3$ | S | C—Br | H | CHF | N |
| I1.68 | $CH_2CH_3$ | S | C—Br | $CH_2CH_3$ | CHF | N |
| I1.69 | $CH_2CH_3$ | S | C—Br | $CH_2C=CH_2$ | CHF | N |
| I1.70 | $CH_2CH_3$ | S | C—Br | $CH_2C.CH$ | CHF | N |
| I1.71 | $CH_2CH_3$ | S | C—Br | $CH_2OCH_3$ | CHF | N |
| I1.72 | $CH_2CH_3$ | S | C—Br | $CH_2OCH_2CH_3$ | CHF | N |
| I1.73 | $CH_3$ | S | C—Cl | H | $CH_2O$ | N |

TABLE I1-continued

Table I1 provides 288 compounds of Formula I1, wherein $R^1$, D, E, $R^2$, A and J are as defined in Table I1 and $R^6$ is methyl.

(I1)

| Compound No. | $R^1$ | D | E | $R^2$ | A | J |
|---|---|---|---|---|---|---|
| I1.74 | $CH_3$ | S | C—Cl | $CH_2CH_3$ | $CH_2O$ | N |
| I1.75 | $CH_3$ | S | C—Cl | $CH_2C=CH_2$ | $CH_2O$ | N |
| I1.76 | $CH_3$ | S | C—Cl | $CH_2C.CH$ | $CH_2O$ | N |
| I1.77 | $CH_3$ | S | C—Cl | $CH_2OCH_3$ | $CH_2O$ | N |
| I1.78 | $CH_3$ | S | C—Cl | $CH_2OCH_2CH_3$ | $CH_2O$ | N |
| I1.79 | $CH_3$ | S | C—Br | H | $CH_2O$ | N |
| I1.80 | $CH_3$ | S | C—Br | $CH_2CH_3$ | $CH_2O$ | N |
| I1.81 | $CH_3$ | S | C—Br | $CH_2C=CH_2$ | $CH_2O$ | N |
| I1.82 | $CH_3$ | S | C—Br | $CH_2C.CH$ | $CH_2O$ | N |
| I1.83 | $CH_3$ | S | C—Br | $CH_2OCH_3$ | $CH_2O$ | N |
| I1.84 | $CH_3$ | S | C—Br | $CH_2OCH_2CH_3$ | $CH_2O$ | N |
| I1.85 | $CH_2CH_3$ | S | C—Cl | H | $CH_2O$ | N |
| I1.86 | $CH_2CH_3$ | S | C—Cl | $CH_2CH_3$ | $CH_2O$ | N |
| I1.87 | $CH_2CH_3$ | S | C—Cl | $CH_2C=CH_2$ | $CH_2O$ | N |
| I1.88 | $CH_2CH_3$ | S | C—Cl | $CH_2C.CH$ | $CH_2O$ | N |
| I1.89 | $CH_2CH_3$ | S | C—Cl | $CH_2OCH_3$ | $CH_2O$ | N |
| I1.90 | $CH_2CH_3$ | S | C—Cl | $CH_2OCH_2CH_3$ | $CH_2O$ | N |
| I1.91 | $CH_2CH_3$ | S | C—Br | H | $CH_2O$ | N |
| I1.92 | $CH_2CH_3$ | S | C—Br | $CH_2CH_3$ | $CH_2O$ | N |
| I1.93 | $CH_2CH_3$ | S | C—Br | $CH_2C=CH_2$ | $CH_2O$ | N |
| I1.94 | $CH_2CH_3$ | S | C—Br | $CH_2C.CH$ | $CH_2O$ | N |
| I1.95 | $CH_2CH_3$ | S | C—Br | $CH_2OCH_3$ | $CH_2O$ | N |
| I1.96 | $CH_2CH_3$ | S | C—Br | $CH_2OCH_2CH_3$ | $CH_2O$ | N |
| I1.97 | $CH_3$ | S | C—Cl | H | $CH_2$ | C—H |
| I1.98 | $CH_3$ | S | C—Cl | $CH_2CH_3$ | $CH_2$ | C—H |
| I1.99 | $CH_3$ | S | C—Cl | $CH_2C=CH_2$ | $CH_2$ | C—H |
| I1.100 | $CH_3$ | S | C—Cl | $CH_2C.CH$ | $CH_2$ | C—H |
| I1.101 | $CH_3$ | S | C—Cl | $CH_2OCH_3$ | $CH_2$ | C—H |
| I1.102 | $CH_3$ | S | C—Cl | $CH_2OCH_2CH_3$ | $CH_2$ | C—H |
| I1.103 | $CH_3$ | S | C—Br | H | $CH_2$ | C—H |
| I1.104 | $CH_3$ | S | C—Br | $CH_2CH_3$ | $CH_2$ | C—H |
| I1.105 | $CH_3$ | S | C—Br | $CH_2C=CH_2$ | $CH_2$ | C—H |
| I1.106 | $CH_3$ | S | C—Br | $CH_2C.CH$ | $CH_2$ | C—H |
| I1.107 | $CH_3$ | S | C—Br | $CH_2OCH_3$ | $CH_2$ | C—H |
| I1.108 | $CH_3$ | S | C—Br | $CH_2OCH_2CH_3$ | $CH_2$ | C—H |
| I1.109 | $CH_2CH_3$ | S | C—Cl | H | $CH_2$ | C—H |
| I1.110 | $CH_2CH_3$ | S | C—Cl | $CH_2CH_3$ | $CH_2$ | C—H |
| I1.111 | $CH_2CH_3$ | S | C—Cl | $CH_2C=CH_2$ | $CH_2$ | C—H |
| I1.112 | $CH_2CH_3$ | S | C—Cl | $CH_2C.CH$ | $CH_2$ | C—H |
| I1.113 | $CH_2CH_3$ | S | C—Cl | $CH_2OCH_3$ | $CH_2$ | C—H |
| I1.114 | $CH_2CH_3$ | S | C—Cl | $CH_2OCH_2CH_3$ | $CH_2$ | C—H |
| I1.115 | $CH_2CH_3$ | S | C—Br | H | $CH_2$ | C—H |
| I1.116 | $CH_2CH_3$ | S | C—Br | $CH_2CH_3$ | $CH_2$ | C—H |
| I1.117 | $CH_2CH_3$ | S | C—Br | $CH_2C=CH_2$ | $CH_2$ | C—H |
| I1.118 | $CH_2CH_3$ | S | C—Br | $CH_2C.CH$ | $CH_2$ | C—H |
| I1.119 | $CH_2CH_3$ | S | C—Br | $CH_2OCH_3$ | $CH_2$ | C—H |
| I1.120 | $CH_2CH_3$ | S | C—Br | $CH_2OCH_2CH_3$ | $CH_2$ | C—H |
| I1.121 | $CH_3$ | S | C—Cl | H | $CH(CH_3)$ | C—H |
| I1.122 | $CH_3$ | S | C—Cl | $CH_2CH_3$ | $CH(CH_3)$ | C—H |
| I1.123 | $CH_3$ | S | C—Cl | $CH_2C=CH_2$ | $CH(CH_3)$ | C—H |
| I1.124 | $CH_3$ | S | C—Cl | $CH_2C.CH$ | $CH(CH_3)$ | C—H |
| I1.125 | $CH_3$ | S | C—Cl | $CH_2OCH_3$ | $CH(CH_3)$ | C—H |
| I1.126 | $CH_3$ | S | C—Cl | $CH_2OCH_2CH_3$ | $CH(CH_3)$ | C—H |
| I1.127 | $CH_3$ | S | C—Br | H | $CH(CH_3)$ | C—H |
| I1.128 | $CH_3$ | S | C—Br | $CH_2CH_3$ | $CH(CH_3)$ | C—H |
| I1.129 | $CH_3$ | S | C—Br | $CH_2C=CH_2$ | $CH(CH_3)$ | C—H |
| I1.130 | $CH_3$ | S | C—Br | $CH_2C.CH$ | $CH(CH_3)$ | C—H |
| I1.131 | $CH_3$ | S | C—Br | $CH_2OCH_3$ | $CH(CH_3)$ | C—H |
| I1.132 | $CH_3$ | S | C—Br | $CH_2OCH_2CH_3$ | $CH(CH_3)$ | C—H |
| I1.133 | $CH_2CH_3$ | S | C—Cl | H | $CH(CH_3)$ | C—H |
| I1.134 | $CH_2CH_3$ | S | C—Cl | $CH_2CH_3$ | $CH(CH_3)$ | C—H |
| I1.135 | $CH_2CH_3$ | S | C—Cl | $CH_2C=CH_2$ | $CH(CH_3)$ | C—H |
| I1.136 | $CH_2CH_3$ | S | C—Cl | $CH_2C.CH$ | $CH(CH_3)$ | C—H |
| I1.137 | $CH_2CH_3$ | S | C—Cl | $CH_2OCH_3$ | $CH(CH_3)$ | C—H |
| I1.138 | $CH_2CH_3$ | S | C—Cl | $CH_2OCH_2CH_3$ | $CH(CH_3)$ | C—H |

TABLE I1-continued

Table I1 provides 288 compounds of Formula I1, wherein $R^1$, D, E, $R^2$, A and J are as defined in Table I1 and $R^6$ is methyl.

(I1)

| Compound No. | $R^1$ | D | E | $R^2$ | A | J |
|---|---|---|---|---|---|---|
| I1.139 | CH$_2$CH$_3$ | S | C—Br | H | CH(CH$_3$) | C—H |
| I1.140 | CH$_2$CH$_3$ | S | C—Br | CH$_2$CH$_3$ | CH(CH$_3$) | C—H |
| I1.141 | CH$_2$CH$_3$ | S | C—Br | CH$_2$C=CH$_2$ | CH(CH$_3$) | C—H |
| I1.142 | CH$_2$CH$_3$ | S | C—Br | CH$_2$C.CH | CH(CH$_3$) | C—H |
| I1.143 | CH$_2$CH$_3$ | S | C—Br | CH$_2$OCH$_3$ | CH(CH$_3$) | C—H |
| I1.144 | CH$_2$CH$_3$ | S | C—Br | CH$_2$OCH$_2$CH$_3$ | CH(CH$_3$) | C—H |
| I1.145 | CH$_3$ | S | C—Cl | H | CHF | C—H |
| I1.146 | CH$_3$ | S | C—Cl | CH$_2$CH$_3$ | CHF | C—H |
| I1.147 | CH$_3$ | S | C—Cl | CH$_2$C=CH$_2$ | CHF | C—H |
| I1.148 | CH$_3$ | S | C—Cl | CH$_2$C.CH | CHF | C—H |
| I1.149 | CH$_3$ | S | C—Cl | CH$_2$OCH$_3$ | CHF | C—H |
| I1.150 | CH$_3$ | S | C—Cl | CH$_2$OCH$_2$CH$_3$ | CHF | C—H |
| I1.151 | CH$_3$ | S | C—Br | H | CHF | C—H |
| I1.152 | CH$_3$ | S | C—Br | CH$_2$CH$_3$ | CHF | C—H |
| I1.153 | CH$_3$ | S | C—Br | CH$_2$C=CH$_2$ | CHF | C—H |
| I1.154 | CH$_3$ | S | C—Br | CH$_2$C.CH | CHF | C—H |
| I1.155 | CH$_3$ | S | C—Br | CH$_2$OCH$_3$ | CHF | C—H |
| I1.156 | CH$_3$ | S | C—Br | CH$_2$OCH$_2$CH$_3$ | CHF | C—H |
| I1.157 | CH$_2$CH$_3$ | S | C—Cl | H | CHF | C—H |
| I1.158 | CH$_2$CH$_3$ | S | C—Cl | CH$_2$CH$_3$ | CHF | C—H |
| I1.159 | CH$_2$CH$_3$ | S | C—Cl | CH$_2$C=CH$_2$ | CHF | C—H |
| I1.160 | CH$_2$CH$_3$ | S | C—Cl | CH$_2$C.CH | CHF | C—H |
| I1.161 | CH$_2$CH$_3$ | S | C—Cl | CH$_2$OCH$_3$ | CHF | C—H |
| I1.162 | CH$_2$CH$_3$ | S | C—Cl | CH$_2$OCH$_2$CH$_3$ | CHF | C—H |
| I1.163 | CH$_2$CH$_3$ | S | C—Br | H | CHF | C—H |
| I1.164 | CH$_2$CH$_3$ | S | C—Br | CH$_2$CH$_3$ | CHF | C—H |
| I1.165 | CH$_2$CH$_3$ | S | C—Br | CH$_2$C=CH$_2$ | CHF | C—H |
| I1.166 | CH$_2$CH$_3$ | S | C—Br | CH$_2$C.CH | CHF | C—H |
| I1.167 | CH$_2$CH$_3$ | S | C—Br | CH$_2$OCH$_3$ | CHF | C—H |
| I1.168 | CH$_2$CH$_3$ | S | C—Br | CH$_2$OCH$_2$CH$_3$ | CHF | C—H |
| I1.169 | CH$_3$ | S | C—Cl | H | CH$_2$O | C—H |
| I1.170 | CH$_3$ | S | C—Cl | CH$_2$CH$_3$ | CH$_2$O | C—H |
| I1.171 | CH$_3$ | S | C—Cl | CH$_2$C=CH$_2$ | CH$_2$O | C—H |
| I1.172 | CH$_3$ | S | C—Cl | CH$_2$C.CH | CH$_2$O | C—H |
| I1.173 | CH$_3$ | S | C—Cl | CH$_2$OCH$_3$ | CH$_2$O | C—H |
| I1.174 | CH$_3$ | S | C—Cl | CH$_2$OCH$_2$CH$_3$ | CH$_2$O | C—H |
| I1.175 | CH$_3$ | S | C—Br | H | CH$_2$O | C—H |
| I1.176 | CH$_3$ | S | C—Br | CH$_2$CH$_3$ | CH$_2$O | C—H |
| I1.177 | CH$_3$ | S | C—Br | CH$_2$C=CH$_2$ | CH$_2$O | C—H |
| I1.178 | CH$_3$ | S | C—Br | CH$_2$C.CH | CH$_2$O | C—H |
| I1.179 | CH$_3$ | S | C—Br | CH$_2$OCH$_3$ | CH$_2$O | C—H |
| I1.180 | CH$_3$ | S | C—Br | CH$_2$OCH$_2$CH$_3$ | CH$_2$O | C—H |
| I1.181 | CH$_2$CH$_3$ | S | C—Cl | H | CH$_2$O | C—H |
| I1.182 | CH$_2$CH$_3$ | S | C—Cl | CH$_2$CH$_3$ | CH$_2$O | C—H |
| I1.183 | CH$_2$CH$_3$ | S | C—Cl | CH$_2$C=CH$_2$ | CH$_2$O | C—H |
| I1.184 | CH$_2$CH$_3$ | S | C—Cl | CH$_2$C.CH | CH$_2$O | C—H |
| I1.185 | CH$_2$CH$_3$ | S | C—Cl | CH$_2$OCH$_3$ | CH$_2$O | C—H |
| I1.186 | CH$_2$CH$_3$ | S | C—Cl | CH$_2$OCH$_2$CH$_3$ | CH$_2$O | C—H |
| I1.187 | CH$_2$CH$_3$ | S | C—Br | H | CH$_2$O | C—H |
| I1.188 | CH$_2$CH$_3$ | S | C—Br | CH$_2$CH$_3$ | CH$_2$O | C—H |
| I1.189 | CH$_2$CH$_3$ | S | C—Br | CH$_2$C=CH$_2$ | CH$_2$O | C—H |
| I1.190 | CH$_2$CH$_3$ | S | C—Br | CH$_2$C.CH | CH$_2$O | C—H |
| I1.191 | CH$_2$CH$_3$ | S | C—Br | CH$_2$OCH$_3$ | CH$_2$O | C—H |
| I1.192 | CH$_2$CH$_3$ | S | C—Br | CH$_2$OCH$_2$CH$_3$ | CH$_2$O | C—H |
| I1.193 | CH$_3$ | S | C—Cl | H | CH$_2$ | C—Cl |
| I1.194 | CH$_3$ | S | C—Cl | CH$_2$CH$_3$ | CH$_2$ | C—Cl |
| I1.195 | CH$_3$ | S | C—Cl | CH$_2$C=CH$_2$ | CH$_2$ | C—Cl |
| I1.196 | CH$_3$ | S | C—Cl | CH$_2$C.CH | CH$_2$ | C—Cl |
| I1.197 | CH$_3$ | S | C—Cl | CH$_2$OCH$_3$ | CH$_2$ | C—Cl |
| I1.198 | CH$_3$ | S | C—Cl | CH$_2$OCH$_2$CH$_3$ | CH$_2$ | C—Cl |
| I1.199 | CH$_3$ | S | C—Br | H | CH$_2$ | C—Cl |
| I1.200 | CH$_3$ | S | C—Br | CH$_2$CH$_3$ | CH$_2$ | C—Cl |
| I1.201 | CH$_3$ | S | C—Br | CH$_2$C=CH$_2$ | CH$_2$ | C—Cl |
| I1.202 | CH$_3$ | S | C—Br | CH$_2$C.CH | CH$_2$ | C—Cl |
| I1.203 | CH$_3$ | S | C—Br | CH$_2$OCH$_3$ | CH$_2$ | C—Cl |

TABLE I1-continued

Table I1 provides 288 compounds of Formula I1, wherein $R^1$, D, E, $R^2$, A and J are as defined in Table I1 and $R^6$ is methyl.

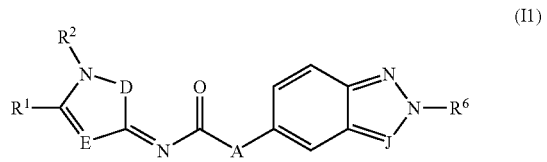

(I1)

| Compound No. | $R^1$ | D | E | $R^2$ | A | J |
|---|---|---|---|---|---|---|
| I1.204 | CH$_3$ | S | C—Br | CH$_2$OCH$_2$CH$_3$ | CH$_2$ | C—Cl |
| I1.205 | CH$_2$CH$_3$ | S | C—Cl | H | CH$_2$ | C—Cl |
| I1.206 | CH$_2$CH$_3$ | S | C—Cl | CH$_2$CH$_3$ | CH$_2$ | C—Cl |
| I1.207 | CH$_2$CH$_3$ | S | C—Cl | CH$_2$C=CH$_2$ | CH$_2$ | C—Cl |
| I1.208 | CH$_2$CH$_3$ | S | C—Cl | CH$_2$C.CH | CH$_2$ | C—Cl |
| I1.209 | CH$_2$CH$_3$ | S | C—Cl | CH$_2$OCH$_3$ | CH$_2$ | C—Cl |
| I1.210 | CH$_2$CH$_3$ | S | C—Cl | CH$_2$OCH$_2$CH$_3$ | CH$_2$ | C—Cl |
| I1.211 | CH$_2$CH$_3$ | S | C—Br | H | CH$_2$ | C—Cl |
| I1.212 | CH$_2$CH$_3$ | S | C—Br | CH$_2$CH$_3$ | CH$_2$ | C—Cl |
| I1.213 | CH$_2$CH$_3$ | S | C—Br | CH$_2$C=CH$_2$ | CH$_2$ | C—Cl |
| I1.214 | CH$_2$CH$_3$ | S | C—Br | CH$_2$C.CH | CH$_2$ | C—Cl |
| I1.215 | CH$_2$CH$_3$ | S | C—Br | CH$_2$OCH$_3$ | CH$_2$ | C—Cl |
| I1.216 | CH$_2$CH$_3$ | S | C—Br | CH$_2$OCH$_2$CH$_3$ | CH$_2$ | C—Cl |
| I1.217 | CH$_3$ | S | C—Cl | H | CH(CH$_3$) | C—Cl |
| I1.218 | CH$_3$ | S | C—Cl | CH$_2$CH$_3$ | CH(CH$_3$) | C—Cl |
| I1.219 | CH$_3$ | S | C—Cl | CH$_2$C=CH$_2$ | CH(CH$_3$) | C—Cl |
| I1.220 | CH$_3$ | S | C—Cl | CH$_2$C.CH | CH(CH$_3$) | C—Cl |
| I1.221 | CH$_3$ | S | C—Cl | CH$_2$OCH$_3$ | CH(CH$_3$) | C—Cl |
| I1.222 | CH$_3$ | S | C—Cl | CH$_2$OCH$_2$CH$_3$ | CH(CH$_3$) | C—Cl |
| I1.223 | CH$_3$ | S | C—Br | H | CH(CH$_3$) | C—Cl |
| I1.224 | CH$_3$ | S | C—Br | CH$_2$CH$_3$ | CH(CH$_3$) | C—Cl |
| I1.225 | CH$_3$ | S | C—Br | CH$_2$C=CH$_2$ | CH(CH$_3$) | C—Cl |
| I1.226 | CH$_3$ | S | C—Br | CH$_2$C.CH | CH(CH$_3$) | C—Cl |
| I1.227 | CH$_3$ | S | C—Br | CH$_2$OCH$_3$ | CH(CH$_3$) | C—Cl |
| I1.228 | CH$_3$ | S | C—Br | CH$_2$OCH$_2$CH$_3$ | CH(CH$_3$) | C—Cl |
| I1.229 | CH$_2$CH$_3$ | S | C—Cl | H | CH(CH$_3$) | C—Cl |
| I1.230 | CH$_2$CH$_3$ | S | C—Cl | CH$_2$CH$_3$ | CH(CH$_3$) | C—Cl |
| I1.231 | CH$_2$CH$_3$ | S | C—Cl | CH$_2$C=CH$_2$ | CH(CH$_3$) | C—Cl |
| I1.232 | CH$_2$CH$_3$ | S | C—Cl | CH$_2$C.CH | CH(CH$_3$) | C—Cl |
| I1.233 | CH$_2$CH$_3$ | S | C—Cl | CH$_2$OCH$_3$ | CH(CH$_3$) | C—Cl |
| I1.234 | CH$_2$CH$_3$ | S | C—Cl | CH$_2$OCH$_2$CH$_3$ | CH(CH$_3$) | C—Cl |
| I1.235 | CH$_2$CH$_3$ | S | C—Br | H | CH(CH$_3$) | C—Cl |
| I1.236 | CH$_2$CH$_3$ | S | C—Br | CH$_2$CH$_3$ | CH(CH$_3$) | C—Cl |
| I1.237 | CH$_2$CH$_3$ | S | C—Br | CH$_2$C=CH$_2$ | CH(CH$_3$) | C—Cl |
| I1.238 | CH$_2$CH$_3$ | S | C—Br | CH$_2$C.CH | CH(CH$_3$) | C—Cl |
| I1.239 | CH$_2$CH$_3$ | S | C—Br | CH$_2$OCH$_3$ | CH(CH$_3$) | C—Cl |
| I1.240 | CH$_2$CH$_3$ | S | C—Br | CH$_2$OCH$_2$CH$_3$ | CH(CH$_3$) | C—Cl |
| I1.241 | CH$_3$ | S | C—Cl | H | CHF | C—Cl |
| I1.242 | CH$_3$ | S | C—Cl | CH$_2$CH$_3$ | CHF | C—Cl |
| I1.243 | CH$_3$ | S | C—Cl | CH$_2$C=CH$_2$ | CHF | C—Cl |
| I1.244 | CH$_3$ | S | C—Cl | CH$_2$C.CH | CHF | C—Cl |
| I1.245 | CH$_3$ | S | C—Cl | CH$_2$OCH$_3$ | CHF | C—Cl |
| I1.246 | CH$_3$ | S | C—Cl | CH$_2$OCH$_2$CH$_3$ | CHF | C—Cl |
| I1.247 | CH$_3$ | S | C—Br | H | CHF | C—Cl |
| I1.248 | CH$_3$ | S | C—Br | CH$_2$CH$_3$ | CHF | C—Cl |
| I1.249 | CH$_3$ | S | C—Br | CH$_2$C=CH$_2$ | CHF | C—Cl |
| I1.250 | CH$_3$ | S | C—Br | CH$_2$C.CH | CHF | C—Cl |
| I1.251 | CH$_3$ | S | C—Br | CH$_2$OCH$_3$ | CHF | C—Cl |
| I1.252 | CH$_3$ | S | C—Br | CH$_2$OCH$_2$CH$_3$ | CHF | C—Cl |
| I1.253 | CH$_2$CH$_3$ | S | C—Cl | H | CHF | C—Cl |
| I1.254 | CH$_2$CH$_3$ | S | C—Cl | CH$_2$CH$_3$ | CHF | C—Cl |
| I1.255 | CH$_2$CH$_3$ | S | C—Cl | CH$_2$C=CH$_2$ | CHF | C—Cl |
| I1.256 | CH$_2$CH$_3$ | S | C—Cl | CH$_2$C.CH | CHF | C—Cl |
| I1.257 | CH$_2$CH$_3$ | S | C—Cl | CH$_2$OCH$_3$ | CHF | C—Cl |
| I1.258 | CH$_2$CH$_3$ | S | C—Cl | CH$_2$OCH$_2$CH$_3$ | CHF | C—Cl |
| I1.259 | CH$_2$CH$_3$ | S | C—Br | H | CHF | C—Cl |
| I1.260 | CH$_2$CH$_3$ | S | C—Br | CH$_2$CH$_3$ | CHF | C—Cl |
| I1.261 | CH$_2$CH$_3$ | S | C—Br | CH$_2$C=CH$_2$ | CHF | C—Cl |
| I1.262 | CH$_2$CH$_3$ | S | C—Br | CH$_2$C.CH | CHF | C—Cl |
| I1.263 | CH$_2$CH$_3$ | S | C—Br | CH$_2$OCH$_3$ | CHF | C—Cl |
| I1.264 | CH$_2$CH$_3$ | S | C—Br | CH$_2$OCH$_2$CH$_3$ | CHF | C—Cl |
| I1.265 | CH$_3$ | S | C—Cl | H | CH$_2$O | C—Cl |
| I1.266 | CH$_3$ | S | C—Cl | CH$_2$CH$_3$ | CH$_2$O | C—Cl |
| I1.267 | CH$_3$ | S | C—Cl | CH$_2$C=CH$_2$ | CH$_2$O | C—Cl |
| I1.268 | CH$_3$ | S | C—Cl | CH$_2$C.CH | CH$_2$O | C—Cl |

TABLE I1-continued

Table I1 provides 288 compounds of Formula I1, wherein $R^1$, D, E, $R^2$, A and J are as defined in Table I1 and $R^6$ is methyl.

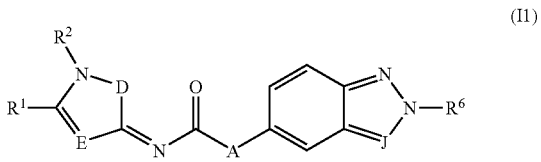
(I1)

| Compound No. | $R^1$ | D | E | $R^2$ | A | J |
|---|---|---|---|---|---|---|
| I1.269 | $CH_3$ | S | C—Cl | $CH_2OCH_3$ | $CH_2O$ | C—Cl |
| I1.270 | $CH_3$ | S | C—Cl | $CH_2OCH_2CH_3$ | $CH_2O$ | C—Cl |
| I1.271 | $CH_3$ | S | C—Br | H | $CH_2O$ | C—Cl |
| I1.272 | $CH_3$ | S | C—Br | $CH_2CH_3$ | $CH_2O$ | C—Cl |
| I1.273 | $CH_3$ | S | C—Br | $CH_2C═CH_2$ | $CH_2O$ | C—Cl |
| I1.274 | $CH_3$ | S | C—Br | $CH_2C.CH$ | $CH_2O$ | C—Cl |
| I1.275 | $CH_3$ | S | C—Br | $CH_2OCH_3$ | $CH_2O$ | C—Cl |
| I1.276 | $CH_3$ | S | C—Br | $CH_2OCH_2CH_3$ | $CH_2O$ | C—Cl |
| I1.277 | $CH_2CH_3$ | S | C—Cl | H | $CH_2O$ | C—Cl |
| I1.278 | $CH_2CH_3$ | S | C—Cl | $CH_2CH_3$ | $CH_2O$ | C—Cl |
| I1.279 | $CH_2CH_3$ | S | C—Cl | $CH_2C═CH_2$ | $CH_2O$ | C—Cl |
| I1.280 | $CH_2CH_3$ | S | C—Cl | $CH_2C.CH$ | $CH_2O$ | C—Cl |
| I1.281 | $CH_2CH_3$ | S | C—Cl | $CH_2OCH_3$ | $CH_2O$ | C—Cl |
| I1.282 | $CH_2CH_3$ | S | C—Cl | $CH_2OCH_2CH_3$ | $CH_2O$ | C—Cl |
| I1.283 | $CH_2CH_3$ | S | C—Br | H | $CH_2O$ | C—Cl |
| I1.284 | $CH_2CH_3$ | S | C—Br | $CH_2CH_3$ | $CH_2O$ | C—Cl |
| I1.285 | $CH_2CH_3$ | S | C—Br | $CH_2C═CH_2$ | $CH_2O$ | C—Cl |
| I1.286 | $CH_2CH_3$ | S | C—Br | $CH_2C.CH$ | $CH_2O$ | C—Cl |
| I1.287 | $CH_2CH_3$ | S | C—Br | $CH_2OCH_3$ | $CH_2O$ | C—Cl |
| I1.288 | $CH_2CH_3$ | S | C—Br | $CH_2OCH_2CH_3$ | $CH_2O$ | C—Cl |

Table I2

Table I2 provides 288 compounds of Formula I1 wherein X, $R^2$, A and J are as defined in Table I1 and $R^6$ is ethyl.

Table I3

Table I3 provides 288 compounds of Formula I1 wherein X, $R^2$, A and J are as defined in Table I1 and $R^6$ is n-propyl.

Table I4

Table I4 provides 288 compounds of Formula I1 wherein X, $R^2$, A and J are as defined in Table I1 and $R^6$ is iso-propyl.

Table I5

Table I5 provides 288 compounds of Formula I1 wherein X, $R^2$, A and J are as defined in Table I1 and $R^6$ is n-butyl.

Table I6

Table I6 provides 288 compounds of Formula I1 wherein X, $R^2$, A and J are as defined in Table I1 and $R^6$ is sec-butyl.

Table I7

Table I7 provides 288 compounds of Formula I1 wherein X, $R^2$, A and J are as defined in Table I1 and $R^6$ is iso-butyl.

Table I8

Table I8 provides 288 compounds of Formula I1 wherein X, $R^2$, A and J are as defined in Table I1 and $R^6$ is tert-butyl.

Table I9

Table I9 provides 288 compounds of Formula I1 wherein X, $R^2$, A and J are as defined in Table I1 and $R^6$ is n-pentyl.

Table I10

Table I10 provides 288 compounds of Formula I1 wherein X, $R^2$, A and J are as defined in Table I1 and $R^6$ is 1-methylbutyl.

Table I11

Table I11 provides 288 compounds of Formula I1 wherein X, $R^2$, A and J are as defined in Table I1 and $R^6$ is 2-methylbutyl.

Table I12

Table I12 provides 288 compounds of Formula I1 wherein X, $R^2$, A and J are as defined in Table I1 and $R^6$ is 3-methylbutyl.

Table I13

Table I13 provides 288 compounds of Formula I1 wherein X, $R^2$, A and J are as defined in Table I1 and $R^6$ is neopentyl.

Table I14

Table I14 provides 288 compounds of Formula I1 wherein X, $R^2$, A and J are as defined in Table I1 and $R^6$ is 2,2-dimethylbutyl.

Table I15

Table I15 provides 288 compounds of Formula I1 wherein X, $R^2$, A and J are as defined in Table I1 and $R^6$ is 2,2,2-trifluoroethyl.

Table I16

Table I16 provides 288 compounds of Formula I1 wherein X, $R^2$, A and J are as defined in Table I1 and $R^6$ is 2,2-difluoro-2-methoxyethyl.

Table I17

Table I17 provides 288 compounds of Formula I1 wherein X, $R^2$, A and J are as defined in Table I1 and $R^6$ is 3,3,3-trifluoropropyl.

Table I18

Table I18 provides 288 compounds of Formula I1 wherein X, $R^2$, A and J are as defined in Table I1 and $R^6$ is para-fluorobenzyl.

Table I19

Table I19 provides 288 compounds of Formula I1 wherein X, $R^2$, A and J are as defined in Table I1 and $R^6$ is 2,4-dichlorophenyl.

Table I20

Table I20 provides 288 compounds of Formula I1 wherein X, $R^2$, A and J are as defined in Table I1 and $R^6$ is 2-chloro-4-trifluoromethylphenyl.

Table J1

Table J1 provides 288 compounds of Formula J1, wherein $R^1$, D, E, $R^2$, A and J are as defined in Table I1 and $R^6$ is methyl.

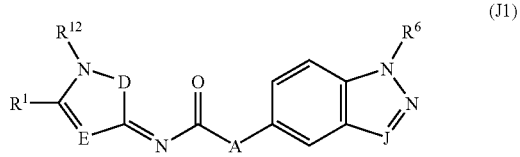

(J1)

Table J2

Table J2 provides 288 compounds of Formula J1 wherein $R^1$, D, E, $R^2$, A and J are as defined in Table I1 and $R^6$ is ethyl.

Table J3

Table J3 provides 288 compounds of Formula J1 wherein $R^1$, D, E, $R^2$, A and J are as defined in Table I1 and $R^6$ is n-propyl.

Table J4

Table J4 provides 288 compounds of Formula J1 wherein $R^1$, D, E, $R^2$, A and J are as defined in Table I1 and $R^6$ is iso-propyl.

Table J5

Table J5 provides 288 compounds of Formula J1 wherein $R^1$, D, E, $R^2$, A and J are as defined in Table I1 and $R^6$ is n-butyl.

Table J6

Table J6 provides 288 compounds of Formula J1 wherein $R^1$, D, E, $R^2$, A and J are as defined in Table J1 and $R^6$ is sec-butyl.

Table J7

Table J7 provides 288 compounds of Formula J1 wherein $R^1$, D, E, $R^2$, A and J are as defined in Table I1 and $R^6$ is iso-butyl.

Table J8

Table J8 provides 288 compounds of Formula J1 wherein $R^1$, D, E, $R^2$, A and J are as defined in Table I1 and $R^6$ is tert-butyl.

Table J9

Table J9 provides 288 compounds of Formula J1 wherein $R^1$, D, E, $R^2$, A and J are as defined in Table I1 and $R^6$ is n-pentyl.

Table J10

Table J10 provides 288 compounds of Formula J1 wherein $R^1$, D, E, $R^2$, A and J are as defined in Table I1 and $R^6$ is 1-methylbutyl.

Table J11

Table J11 provides 288 compounds of Formula J1 wherein $R^1$, D, E, $R^2$, A and J are as defined in Table I1 and $R^6$ is 2-methylbutyl.

Table J12

Table J12 provides 288 compounds of Formula J1 wherein $R^1$, D, E, $R^2$, A and J are as defined in Table I1 and $R^6$ is 3-methylbutyl.

Table J13

Table J13 provides 288 compounds of Formula J1 wherein $R^1$, D, E, $R^2$, A and J are as defined in Table I1 and $R^6$ is neopentyl.

Table J14

Table J14 provides 288 compounds of Formula J1 wherein $R^1$, D, E, $R^2$, A and J are as defined in Table I1 and $R^6$ is 2,2-dimethylbutyl.

Table J15

Table J15 provides 288 compounds of Formula J1 wherein $R^1$, D, E, $R^2$, A and J are as defined in Table I1 and $R^6$ is 2,2,2-trifluoroethyl.

Table J16

Table J16 provides 288 compounds of Formula J1 wherein $R^1$, D, E, $R^2$, A and J are as defined in Table I1 and $R^6$ is 2,2-difluoro-2-methoxyethyl.

Table J17

Table J17 provides 288 compounds of Formula J1 wherein $R^1$, D, E, $R^2$, A and J are as defined in Table I1 and $R^6$ is 3,3,3-trifluoropropyl.

Table J18

Table J18 provides 288 compounds of Formula J1 wherein $R^1$, D, E, $R^2$, A and J are as defined in Table I1 and $R^6$ is para-fluorobenzyl.

Table J19

Table J19 provides 288 compounds of Formula J1 wherein $R^1$, D, E, $R^2$, A and J are as defined in Table I1 and $R^6$ is 2,4-dichlorophenyl.

Table J20

Table J20 provides 288 compounds of Formula J1 wherein $R^1$, D, E, $R^2$, A and J are as defined in Table I1 and $R^6$ is 2-chloro-4-trifluoromethylphenyl.

Table K1

Table K1 provides 288 compounds of Formula K1, wherein $R^1$, D, E, $R^2$, A and J are as defined in Table I1 and $R^6$ is methyl.

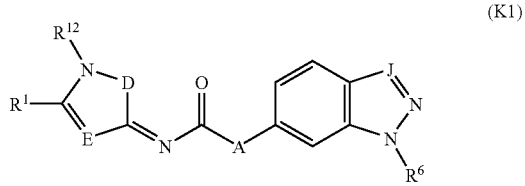

(K1)

Table K2

Table K2 provides 288 compounds of Formula K1 wherein $R^1$, D, E, $R^2$, A and J are as defined in Table I1 and $R^6$ is ethyl.

Table K3

Table K3 provides 288 compounds of Formula K1 wherein $R^1$, D, E, $R^2$, A and J are as defined in Table I1 and $R^6$ is n-propyl.

Table K4

Table K4 provides 288 compounds of Formula K1 wherein $R^1$, D, E, $R^2$, A and J are as defined in Table I1 and $R^6$ is iso-propyl.

Table K5

Table K5 provides 288 compounds of Formula K1 wherein $R^1$, D, E, $R^2$, A and J are as defined in Table I1 and $R^6$ is n-butyl.

Table K6

Table K6 provides 288 compounds of Formula K1 wherein $R^1$, D, E, $R^2$, A and J are as defined in Table I1 and $R^6$ is sec-butyl.

Table K7

Table K7 provides 288 compounds of Formula K1 wherein $R^1$, D, E, $R^2$, A and J are as defined in Table I1 and $R^6$ is iso-butyl.

Table K8

Table K8 provides 288 compounds of Formula K1 wherein $R^1$, D, E, $R^2$, A and J are as defined in Table I1 and $R^6$ is tert-butyl.

Table K9

Table K9 provides 288 compounds of Formula K1 wherein $R^1$, D, E, $R^2$, A and J are as defined in Table I1 and $R^6$ is n-pentyl.

Table K10

Table K10 provides 288 compounds of Formula K1 wherein $R^1$, D, E, $R^2$, A and J are as defined in Table I1 and $R^6$ is 1-methylbutyl.

Table K11

Table K11 provides 288 compounds of Formula K1 wherein $R^1$, D, E, $R^2$, A and J are as defined in Table I1 and $R^6$ is 2-methylbutyl.

Table K12

Table K12 provides 288 compounds of Formula K1 wherein. $R^1$, D, E, $R^2$, A and J are as defined in Table I1 and $R^6$ is 3-methylbutyl.

Table K13

Table K13 provides 288 compounds of Formula K1 wherein $R^1$, D, E, $R^2$, A and J are as defined in Table I1 and $R^6$ is neopentyl.

Table K14

Table K14 provides 288 compounds of Formula K1 wherein $R^1$, D, E, $R^2$, A and J are as defined in Table I1 and $R^6$ is 2,2-dimethylbutyl.

Table K15

Table K15 provides 288 compounds of Formula K1 wherein $R^1$, D, E, $R^2$, A and J are as defined in Table I1 and $R^6$ is 2,2,2-trifluoroethyl.

Table K16

Table K16 provides 288 compounds of Formula K1 wherein $R^1$, D, E, $R^2$, A and J are as defined in Table I1 and $R^6$ is 2,2-difluoro-2-methoxyethyl.

Table K17

Table K17 provides 288 compounds of Formula K1 wherein $R^1$, D, E, $R^2$, A and J are as defined in Table I1 and $R^6$ is 3,3,3-trifluoropropyl.

Table K18

Table K18 provides 288 compounds of Formula K1 wherein $R^1$, D, E, $R^2$, A and J are as defined in Table I1 and $R^6$ is para-fluorobenzyl.

Table K19

Table K19 provides 288 compounds of Formula K1 wherein $R^1$, D, E, $R^2$, A and J are as defined in Table I1 and $R^6$ is 2,4-dichlorophenyl.

Table K20

Table K20 provides 288 compounds of Formula K1 wherein $R^1$, D, E, $R^2$, A and J are as defined in Table I1 and $R^6$ is 2-chloro-4-trifluoromethylphenyl.

TABLE L1

Table L1 provides 192 compounds of Formula L1, wherein $R^1$, D, E, $R^2$, A and J are as defined in Table L1 and $R^6$ is methyl.

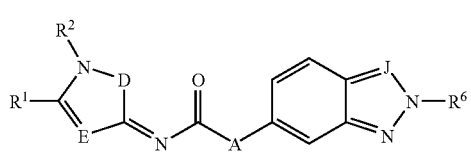

(L1)

| Compound No. | $R^1$ | D | E | $R^2$ | A | J |
|---|---|---|---|---|---|---|
| L1.1 | $CH_3$ | S | C—Cl | H | $CH_2$ | C—H |
| L1.2 | $CH_3$ | S | C—Cl | $CH_2CH_3$ | $CH_2$ | C—H |
| L1.3 | $CH_3$ | S | C—Cl | $CH_2C=CH_2$ | $CH_2$ | C—H |
| L1.4 | $CH_3$ | S | C—Cl | $CH_2C.CH$ | $CH_2$ | C—H |
| L1.5 | $CH_3$ | S | C—Cl | $CH_2OCH_3$ | $CH_2$ | C—H |
| L1.6 | $CH_3$ | S | C—Cl | $CH_2OCH_2CH_3$ | $CH_2$ | C—H |
| L1.7 | $CH_3$ | S | C—Br | H | $CH_2$ | C—H |
| L1.8 | $CH_3$ | S | C—Br | $CH_2CH_3$ | $CH_2$ | C—H |
| L1.9 | $CH_3$ | S | C—Br | $CH_2C=CH_2$ | $CH_2$ | C—H |
| L1.10 | $CH_3$ | S | C—Br | $CH_2C.CH$ | $CH_2$ | C—H |
| L1.11 | $CH_3$ | S | C—Br | $CH_2OCH_3$ | $CH_2$ | C—H |
| L1.12 | $CH_3$ | S | C—Br | $CH_2OCH_2CH_3$ | $CH_2$ | C—H |
| L1.13 | $CH_2CH_3$ | S | C—Cl | H | $CH_2$ | C—H |
| L1.14 | $CH_2CH_3$ | S | C—Cl | $CH_2CH_3$ | $CH_2$ | C—H |
| L1.15 | $CH_2CH_3$ | S | C—Cl | $CH_2C=CH_2$ | $CH_2$ | C—H |
| L1.16 | $CH_2CH_3$ | S | C—Cl | $CH_2C.CH$ | $CH_2$ | C—H |
| L1.17 | $CH_2CH_3$ | S | C—Cl | $CH_2OCH_3$ | $CH_2$ | C—H |
| L1.18 | $CH_2CH_3$ | S | C—Cl | $CH_2OCH_2CH_3$ | $CH_2$ | C—H |
| L1.19 | $CH_2CH_3$ | S | C—Br | H | $CH_2$ | C—H |
| L1.20 | $CH_2CH_3$ | S | C—Br | $CH_2CH_3$ | $CH_2$ | C—H |
| L1.21 | $CH_2CH_3$ | S | C—Br | $CH_2C=CH_2$ | $CH_2$ | C—H |
| L1.22 | $CH_2CH_3$ | S | C—Br | $CH_2C.CH$ | $CH_2$ | C—H |
| L1.23 | $CH_2CH_3$ | S | C—Br | $CH_2OCH_3$ | $CH_2$ | C—H |
| L1.24 | $CH_2CH_3$ | S | C—Br | $CH_2OCH_2CH_3$ | $CH_2$ | C—H |
| L1.25 | $CH_3$ | S | C—Cl | H | $CH(CH_3)$ | C—H |
| L1.26 | $CH_3$ | S | C—Cl | $CH_2CH_3$ | $CH(CH_3)$ | C—H |
| L1.27 | $CH_3$ | S | C—Cl | $CH_2C=CH_2$ | $CH(CH_3)$ | C—H |
| L1.28 | $CH_3$ | S | C—Cl | $CH_2C.CH$ | $CH(CH_3)$ | C—H |
| L1.29 | $CH_3$ | S | C—Cl | $CH_2OCH_3$ | $CH(CH_3)$ | C—H |
| L1.30 | $CH_3$ | S | C—Cl | $CH_2OCH_2CH_3$ | $CH(CH_3)$ | C—H |
| L1.31 | $CH_3$ | S | C—Br | H | $CH(CH_3)$ | C—H |
| L1.32 | $CH_3$ | S | C—Br | $CH_2CH_3$ | $CH(CH_3)$ | C—H |
| L1.33 | $CH_3$ | S | C—Br | $CH_2C=CH_2$ | $CH(CH_3)$ | C—H |
| L1.34 | $CH_3$ | S | C—Br | $CH_2C.CH$ | $CH(CH_3)$ | C—H |
| L1.35 | $CH_3$ | S | C—Br | $CH_2OCH_3$ | $CH(CH_3)$ | C—H |
| L1.36 | $CH_3$ | S | C—Br | $CH_2OCH_2CH_3$ | $CH(CH_3)$ | C—H |
| L1.37 | $CH_2CH_3$ | S | C—Cl | H | $CH(CH_3)$ | C—H |
| L1.38 | $CH_2CH_3$ | S | C—Cl | $CH_2CH_3$ | $CH(CH_3)$ | C—H |
| L1.39 | $CH_2CH_3$ | S | C—Cl | $CH_2C=CH_2$ | $CH(CH_3)$ | C—H |
| L1.40 | $CH_2CH_3$ | S | C—Cl | $CH_2C.CH$ | $CH(CH_3)$ | C—H |
| L1.41 | $CH_2CH_3$ | S | C—Cl | $CH_2OCH_3$ | $CH(CH_3)$ | C—H |
| L1.42 | $CH_2CH_3$ | S | C—Cl | $CH_2OCH_2CH_3$ | $CH(CH_3)$ | C—H |
| L1.43 | $CH_2CH_3$ | S | C—Br | H | $CH(CH_3)$ | C—H |

TABLE L1-continued

Table L1 provides 192 compounds of Formula L1, wherein $R^1$, D, E, $R^2$, A and J are as defined in Table L1 and $R^6$ is methyl.

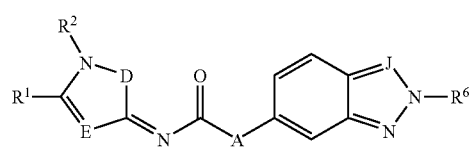

(L1)

| Compound No. | $R^1$ | D | E | $R^2$ | A | J |
|---|---|---|---|---|---|---|
| L1.44 | $CH_2CH_3$ | S | C—Br | $CH_2CH_3$ | $CH(CH_3)$ | C—H |
| L1.45 | $CH_2CH_3$ | S | C—Br | $CH_2C=CH_2$ | $CH(CH_3)$ | C—H |
| L1.46 | $CH_2CH_3$ | S | C—Br | $CH_2C.CH$ | $CH(CH_3)$ | C—H |
| L1.47 | $CH_2CH_3$ | S | C—Br | $CH_2OCH_3$ | $CH(CH_3)$ | C—H |
| L1.48 | $CH_2CH_3$ | S | C—Br | $CH_2OCH_2CH_3$ | $CH(CH_3)$ | C—H |
| L1.49 | $CH_3$ | S | C—Cl | H | CHF | C—H |
| L1.50 | $CH_3$ | S | C—Cl | $CH_2CH_3$ | CHF | C—H |
| L1.51 | $CH_3$ | S | C—Cl | $CH_2C=CH_2$ | CHF | C—H |
| L1.52 | $CH_3$ | S | C—Cl | $CH_2C.CH$ | CHF | C—H |
| L1.53 | $CH_3$ | S | C—Cl | $CH_2OCH_3$ | CHF | C—H |
| L1.54 | $CH_3$ | S | C—Cl | $CH_2OCH_2CH_3$ | CHF | C—H |
| L1.55 | $CH_3$ | S | C—Br | H | CHF | C—H |
| L1.56 | $CH_3$ | S | C—Br | $CH_2CH_3$ | CHF | C—H |
| L1.57 | $CH_3$ | S | C—Br | $CH_2C=CH_2$ | CHF | C—H |
| L1.58 | $CH_3$ | S | C—Br | $CH_2C.CH$ | CHF | C—H |
| L1.59 | $CH_3$ | S | C—Br | $CH_2OCH_3$ | CHF | C—H |
| L1.60 | $CH_3$ | S | C—Br | $CH_2OCH_2CH_3$ | CHF | C—H |
| L1.61 | $CH_2CH_3$ | S | C—Cl | H | CHF | C—H |
| L1.62 | $CH_2CH_3$ | S | C—Cl | $CH_2CH_3$ | CHF | C—H |
| L1.63 | $CH_2CH_3$ | S | C—Cl | $CH_2C=CH_2$ | CHF | C—H |
| L1.64 | $CH_2CH_3$ | S | C—Cl | $CH_2C.CH$ | CHF | C—H |
| L1.65 | $CH_2CH_3$ | S | C—Cl | $CH_2OCH_3$ | CHF | C—H |
| L1.66 | $CH_2CH_3$ | S | C—Cl | $CH_2OCH_2CH_3$ | CHF | C—H |
| L1.67 | $CH_2CH_3$ | S | C—Br | H | CHF | C—H |
| L1.68 | $CH_2CH_3$ | S | C—Br | $CH_2CH_3$ | CHF | C—H |
| L1.69 | $CH_2CH_3$ | S | C—Br | $CH_2C=CH_2$ | CHF | C—H |
| L1.70 | $CH_2CH_3$ | S | C—Br | $CH_2C.CH$ | CHF | C—H |
| L1.71 | $CH_2CH_3$ | S | C—Br | $CH_2OCH_3$ | CHF | C—H |
| L1.72 | $CH_2CH_3$ | S | C—Br | $CH_2OCH_2CH_3$ | CHF | C—H |
| L1.73 | $CH_3$ | S | C—Cl | H | $CH_2O$ | C—H |
| L1.74 | $CH_3$ | S | C—Cl | $CH_2CH_3$ | $CH_2O$ | C—H |
| L1.75 | $CH_3$ | S | C—Cl | $CH_2C=CH_2$ | $CH_2O$ | C—H |
| L1.76 | $CH_3$ | S | C—Cl | $CH_2C.CH$ | $CH_2O$ | C—H |
| L1.77 | $CH_3$ | S | C—Cl | $CH_2OCH_3$ | $CH_2O$ | C—H |
| L1.78 | $CH_3$ | S | C—Cl | $CH_2OCH_2CH_3$ | $CH_2O$ | C—H |
| L1.79 | $CH_3$ | S | C—Br | H | $CH_2O$ | C—H |
| L1.80 | $CH_3$ | S | C—Br | $CH_2CH_3$ | $CH_2O$ | C—H |
| L1.81 | $CH_3$ | S | C—Br | $CH_2C=CH_2$ | $CH_2O$ | C—H |
| L1.82 | $CH_3$ | S | C—Br | $CH_2C.CH$ | $CH_2O$ | C—H |
| L1.83 | $CH_3$ | S | C—Br | $CH_2OCH_3$ | $CH_2O$ | C—H |
| L1.84 | $CH_3$ | S | C—Br | $CH_2OCH_2CH_3$ | $CH_2O$ | C—H |
| L1.85 | $CH_2CH_3$ | S | C—Cl | H | $CH_2O$ | C—H |
| L1.86 | $CH_2CH_3$ | S | C—Cl | $CH_2CH_3$ | $CH_2O$ | C—H |
| L1.87 | $CH_2CH_3$ | S | C—Cl | $CH_2C=CH_2$ | $CH_2O$ | C—H |
| L1.88 | $CH_2CH_3$ | S | C—Cl | $CH_2C.CH$ | $CH_2O$ | C—H |
| L1.89 | $CH_2CH_3$ | S | C—Cl | $CH_2OCH_3$ | $CH_2O$ | C—H |
| L1.90 | $CH_2CH_3$ | S | C—Cl | $CH_2OCH_2CH_3$ | $CH_2O$ | C—H |
| L1.91 | $CH_2CH_3$ | S | C—Br | H | $CH_2O$ | C—H |
| L1.92 | $CH_2CH_3$ | S | C—Br | $CH_2CH_3$ | $CH_2O$ | C—H |
| L1.93 | $CH_2CH_3$ | S | C—Br | $CH_2C=CH_2$ | $CH_2O$ | C—H |
| L1.94 | $CH_2CH_3$ | S | C—Br | $CH_2C.CH$ | $CH_2O$ | C—H |
| L1.95 | $CH_2CH_3$ | S | C—Br | $CH_2OCH_3$ | $CH_2O$ | C—H |
| L1.96 | $CH_2CH_3$ | S | C—Br | $CH_2OCH_2CH_3$ | $CH_2O$ | C—H |
| L1.97 | $CH_3$ | S | C—Cl | H | $CH_2$ | C—Cl |
| L1.98 | $CH_3$ | S | C—Cl | $CH_2CH_3$ | $CH_2$ | C—Cl |
| L1.99 | $CH_3$ | S | C—Cl | $CH_2C=CH_2$ | $CH_2$ | C—Cl |
| L1.100 | $CH_3$ | S | C—Cl | $CH_2C.CH$ | $CH_2$ | C—Cl |
| L1.101 | $CH_3$ | S | C—Cl | $CH_2OCH_3$ | $CH_2$ | C—Cl |
| L1.102 | $CH_3$ | S | C—Cl | $CH_2OCH_2CH_3$ | $CH_2$ | C—Cl |
| L1.103 | $CH_3$ | S | C—Br | H | $CH_2$ | C—Cl |
| L1.104 | $CH_3$ | S | C—Br | $CH_2CH_3$ | $CH_2$ | C—Cl |
| L1.105 | $CH_3$ | S | C—Br | $CH_2C=CH_2$ | $CH_2$ | C—Cl |
| L1.106 | $CH_3$ | S | C—Br | $CH_2C.CH$ | $CH_2$ | C—Cl |
| L1.107 | $CH_3$ | S | C—Br | $CH_2OCH_3$ | $CH_2$ | C—Cl |
| L1.108 | $CH_3$ | S | C—Br | $CH_2OCH_2CH_3$ | $CH_2$ | C—Cl |

TABLE L1-continued

Table L1 provides 192 compounds of Formula L1, wherein $R^1$, D, E, $R^2$, A and J are as defined in Table L1 and $R^6$ is methyl.

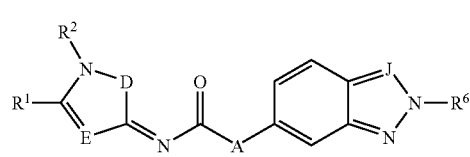

(L1)

| Compound No. | $R^1$ | D | E | $R^2$ | A | J |
|---|---|---|---|---|---|---|
| L1.109 | $CH_2CH_3$ | S | C—Cl | H | $CH_2$ | C—Cl |
| L1.110 | $CH_2CH_3$ | S | C—Cl | $CH_2CH_3$ | $CH_2$ | C—Cl |
| L1.111 | $CH_2CH_3$ | S | C—Cl | $CH_2C=CH_2$ | $CH_2$ | C—Cl |
| L1.112 | $CH_2CH_3$ | S | C—Cl | $CH_2C.CH$ | $CH_2$ | C—Cl |
| L1.113 | $CH_2CH_3$ | S | C—Cl | $CH_2OCH_3$ | $CH_2$ | C—Cl |
| L1.114 | $CH_2CH_3$ | S | C—Cl | $CH_2OCH_2CH_3$ | $CH_2$ | C—Cl |
| L1.115 | $CH_2CH_3$ | S | C—Br | H | $CH_2$ | C—Cl |
| L1.116 | $CH_2CH_3$ | S | C—Br | $CH_2CH_3$ | $CH_2$ | C—Cl |
| L1.117 | $CH_2CH_3$ | S | C—Br | $CH_2C=CH_2$ | $CH_2$ | C—Cl |
| L1.118 | $CH_2CH_3$ | S | C—Br | $CH_2C.CH$ | $CH_2$ | C—Cl |
| L1.119 | $CH_2CH_3$ | S | C—Br | $CH_2OCH_3$ | $CH_2$ | C—Cl |
| L1.120 | $CH_2CH_3$ | S | C—Br | $CH_2OCH_2CH_3$ | $CH_2$ | C—Cl |
| L1.121 | $CH_3$ | S | C—Cl | H | $CH(CH_3)$ | C—Cl |
| L1.122 | $CH_3$ | S | C—Cl | $CH_2CH_3$ | $CH(CH_3)$ | C—Cl |
| L1.123 | $CH_3$ | S | C—Cl | $CH_2C=CH_2$ | $CH(CH_3)$ | C—Cl |
| L1.124 | $CH_3$ | S | C—Cl | $CH_2C.CH$ | $CH(CH_3)$ | C—Cl |
| L1.125 | $CH_3$ | S | C—Cl | $CH_2OCH_3$ | $CH(CH_3)$ | C—Cl |
| L1.126 | $CH_3$ | S | C—Cl | $CH_2OCH_2CH_3$ | $CH(CH_3)$ | C—Cl |
| L1.127 | $CH_3$ | S | C—Br | H | $CH(CH_3)$ | C—Cl |
| L1.128 | $CH_3$ | S | C—Br | $CH_2CH_3$ | $CH(CH_3)$ | C—Cl |
| L1.129 | $CH_3$ | S | C—Br | $CH_2C=CH_2$ | $CH(CH_3)$ | C—Cl |
| L1.130 | $CH_3$ | S | C—Br | $CH_2C.CH$ | $CH(CH_3)$ | C—Cl |
| L1.131 | $CH_3$ | S | C—Br | $CH_2OCH_3$ | $CH(CH_3)$ | C—Cl |
| L1.132 | $CH_3$ | S | C—Br | $CH_2OCH_2CH_3$ | $CH(CH_3)$ | C—Cl |
| L1.133 | $CH_2CH_3$ | S | C—Cl | H | $CH(CH_3)$ | C—Cl |
| L1.134 | $CH_2CH_3$ | S | C—Cl | $CH_2CH_3$ | $CH(CH_3)$ | C—Cl |
| L1.135 | $CH_2CH_3$ | S | C—Cl | $CH_2C=CH_2$ | $CH(CH_3)$ | C—Cl |
| L1.136 | $CH_2CH_3$ | S | C—Cl | $CH_2C.CH$ | $CH(CH_3)$ | C—Cl |
| L1.137 | $CH_2CH_3$ | S | C—Cl | $CH_2OCH_3$ | $CH(CH_3)$ | C—Cl |
| L1.138 | $CH_2CH_3$ | S | C—Cl | $CH_2OCH_2CH_3$ | $CH(CH_3)$ | C—Cl |
| L1.139 | $CH_2CH_3$ | S | C—Br | H | $CH(CH_3)$ | C—Cl |
| L1.140 | $CH_2CH_3$ | S | C—Br | $CH_2CH_3$ | $CH(CH_3)$ | C—Cl |
| L1.141 | $CH_2CH_3$ | S | C—Br | $CH_2C=CH_2$ | $CH(CH_3)$ | C—Cl |
| L1.142 | $CH_2CH_3$ | S | C—Br | $CH_2C.CH$ | $CH(CH_3)$ | C—Cl |
| L1.143 | $CH_2CH_3$ | S | C—Br | $CH_2OCH_3$ | $CH(CH_3)$ | C—Cl |
| L1.144 | $CH_2CH_3$ | S | C—Br | $CH_2OCH_2CH_3$ | $CH(CH_3)$ | C—Cl |
| L1.145 | $CH_3$ | S | C—Cl | H | CHF | C—Cl |
| L1.146 | $CH_3$ | S | C—Cl | $CH_2CH_3$ | CHF | C—Cl |
| L1.147 | $CH_3$ | S | C—Cl | $CH_2C=CH_2$ | CHF | C—Cl |
| L1.148 | $CH_3$ | S | C—Cl | $CH_2C.CH$ | CHF | C—Cl |
| L1.149 | $CH_3$ | S | C—Cl | $CH_2OCH_3$ | CHF | C—Cl |
| L1.150 | $CH_3$ | S | C—Cl | $CH_2OCH_2CH_3$ | CHF | C—Cl |
| L1.151 | $CH_3$ | S | C—Br | H | CHF | C—Cl |
| L1.152 | $CH_3$ | S | C—Br | $CH_2CH_3$ | CHF | C—Cl |
| L1.153 | $CH_3$ | S | C—Br | $CH_2C=CH_2$ | CHF | C—Cl |
| L1.154 | $CH_3$ | S | C—Br | $CH_2C.CH$ | CHF | C—Cl |
| L1.155 | $CH_3$ | S | C—Br | $CH_2OCH_3$ | CHF | C—Cl |
| L1.156 | $CH_3$ | S | C—Br | $CH_2OCH_2CH_3$ | CHF | C—Cl |
| L1.157 | $CH_2CH_3$ | S | C—Cl | H | CHF | C—Cl |
| L1.158 | $CH_2CH_3$ | S | C—Cl | $CH_2CH_3$ | CHF | C—Cl |
| L1.159 | $CH_2CH_3$ | S | C—Cl | $CH_2C=CH_2$ | CHF | C—Cl |
| L1.160 | $CH_2CH_3$ | S | C—Cl | $CH_2C.CH$ | CHF | C—Cl |
| L1.161 | $CH_2CH_3$ | S | C—Cl | $CH_2OCH_3$ | CHF | C—Cl |
| L1.162 | $CH_2CH_3$ | S | C—Cl | $CH_2OCH_2CH_3$ | CHF | C—Cl |
| L1.163 | $CH_2CH_3$ | S | C—Br | H | CHF | C—Cl |
| L1.164 | $CH_2CH_3$ | S | C—Br | $CH_2CH_3$ | CHF | C—Cl |
| L1.165 | $CH_2CH_3$ | S | C—Br | $CH_2C=CH_2$ | CHF | C—Cl |
| L1.166 | $CH_2CH_3$ | S | C—Br | $CH_2C.CH$ | CHF | C—Cl |
| L1.167 | $CH_2CH_3$ | S | C—Br | $CH_2OCH_3$ | CHF | C—Cl |
| L1.168 | $CH_2CH_3$ | S | C—Br | $CH_2OCH_2CH_3$ | CHF | C—Cl |
| L1.169 | $CH_3$ | S | C—Cl | H | $CH_2O$ | C—Cl |
| L1.170 | $CH_3$ | S | C—Cl | $CH_2CH_3$ | $CH_2O$ | C—Cl |
| L1.171 | $CH_3$ | S | C—Cl | $CH_2C=CH_2$ | $CH_2O$ | C—Cl |
| L1.172 | $CH_3$ | S | C—Cl | $CH_2C.CH$ | $CH_2O$ | C—Cl |
| L1.173 | $CH_3$ | S | C—Cl | $CH_2OCH_3$ | $CH_2O$ | C—Cl |

TABLE L1-continued

Table L1 provides 192 compounds of Formula L1, wherein $R^1$, D, E, $R^2$, A and J are as defined in Table L1 and $R^6$ is methyl.

(L1)

| Compound No. | $R^1$ | D | E | $R^2$ | A | J |
|---|---|---|---|---|---|---|
| L1.174 | $CH_3$ | S | C—Cl | $CH_2OCH_2CH_3$ | $CH_2O$ | C—Cl |
| L1.175 | $CH_3$ | S | C—Br | H | $CH_2O$ | C—Cl |
| L1.176 | $CH_3$ | S | C—Br | $CH_2CH_3$ | $CH_2O$ | C—Cl |
| L1.177 | $CH_3$ | S | C—Br | $CH_2C=CH_2$ | $CH_2O$ | C—Cl |
| L1.178 | $CH_3$ | S | C—Br | $CH_2C.CH$ | $CH_2O$ | C—Cl |
| L1.179 | $CH_3$ | S | C—Br | $CH_2OCH_3$ | $CH_2O$ | C—Cl |
| L1.180 | $CH_3$ | S | C—Br | $CH_2OCH_2CH_3$ | $CH_2O$ | C—Cl |
| L1.181 | $CH_2CH_3$ | S | C—Cl | H | $CH_2O$ | C—Cl |
| L1.182 | $CH_2CH_3$ | S | C—Cl | $CH_2CH_3$ | $CH_2O$ | C—Cl |
| L1.183 | $CH_2CH_3$ | S | C—Cl | $CH_2C=CH_2$ | $CH_2O$ | C—Cl |
| L1.184 | $CH_2CH_3$ | S | C—Cl | $CH_2C.CH$ | $CH_2O$ | C—Cl |
| L1.185 | $CH_2CH_3$ | S | C—Cl | $CH_2OCH_3$ | $CH_2O$ | C—Cl |
| L1.186 | $CH_2CH_3$ | S | C—Cl | $CH_2OCH_2CH_3$ | $CH_2O$ | C—Cl |
| L1.187 | $CH_2CH_3$ | S | C—Br | H | $CH_2O$ | C—Cl |
| L1.188 | $CH_2CH_3$ | S | C—Br | $CH_2CH_3$ | $CH_2O$ | C—Cl |
| L1.189 | $CH_2CH_3$ | S | C—Br | $CH_2C=CH_2$ | $CH_2O$ | C—Cl |
| L1.190 | $CH_2CH_3$ | S | C—Br | $CH_2C.CH$ | $CH_2O$ | C—Cl |
| L1.191 | $CH_2CH_3$ | S | C—Br | $CH_2OCH_3$ | $CH_2O$ | C—Cl |
| L1.192 | $CH_2CH_3$ | S | C—Br | $CH_2OCH_2CH_3$ | $CH_2O$ | C—Cl |

Table L2

Table L2 provides 192 compounds of Formula L1 wherein $R^1$, D, E, $R^2$, A and J are as defined in Table L1 and $R^6$ is ethyl.

Table L3

Table L3 provides 192 compounds of Formula L1 wherein $R^1$, D, E, $R^2$, A and J are as defined in Table L1 and $R^6$ is n-propyl.

Table L4

Table L4 provides 192 compounds of Formula L1 wherein $R^1$, D, E, $R^2$, A and J are as defined in Table L1 and $R^6$ is iso-propyl.

Table L5

Table L5 provides 192 compounds of Formula L1 wherein $R^1$, D, E, $R^2$, A and J are as defined in Table L1 and $R^6$ is n-butyl.

Table L6

Table L6 provides 192 compounds of Formula L1 wherein $R^1$, D, E, $R^2$, A and J are as defined in Table L1 and $R^6$ is sec-butyl.

Table L7

Table L7 provides 192 compounds of Formula L1 wherein $R^1$, D, E, $R^2$, A and J are as defined in Table L1 and $R^6$ is iso-butyl.

Table L8

Table L8 provides 192 compounds of Formula L1 wherein $R^1$, D, E, $R^2$, A and J are as defined in Table L1 and $R^6$ is tert-butyl.

Table L9

Table L9 provides 192 compounds of Formula L1 wherein $R^1$, D, E, $R^2$, A and J are as defined in Table L1 and $R^6$ is n-pentyl.

Table L10

Table L10 provides 192 compounds of Formula L1 wherein $R^1$, D, E, $R^2$, A and J are as defined in Table L1 and $R^6$ is 1-methylbutyl.

Table L11

Table L11 provides 192 compounds of Formula L1 wherein $R^1$, D, E, $R^2$, A and J are as defined in Table L1 and $R^6$ is 2-methylbutyl.

Table L12

Table L12 provides 192 compounds of Formula L1 wherein $R^1$, D, E, $R^2$, A and J are as defined in Table L1 and $R^6$ is 3-methylbutyl.

Table L13

Table L13 provides 192 compounds of Formula L1 wherein $R^1$, D, E, $R^2$, A and J are as defined in Table L1 and $R^6$ is neopentyl.

Table L14

Table L14 provides 192 compounds of Formula L1 wherein $R^1$, D, E, $R^2$, A and J are as defined in Table L1 and $R^6$ is 2,2-dimethylbutyl.

Table L15

Table L15 provides 192 compounds of Formula L1 wherein $R^1$, D, E, $R^2$, A and J are as defined in Table L1 and $R^6$ is 2,2,2-trifluoroethyl.

Table L16

Table L16 provides 192 compounds of Formula L1 wherein $R^1$, D, E, $R^2$, A and J are as defined in Table L1 and $R^6$ is 2,2-difluoro-2-methoxyethyl.

Table L17

Table L17 provides 192 compounds of Formula L1 wherein $R^1$, D, E, $R^2$, A and J are as defined in Table L1 and $R^6$ is 3,3,3-trifluoropropyl.

Table L18

Table L18 provides 192 compounds of Formula L1 wherein $R^1$, D, E, $R^2$, A and J are as defined in Table L1 and $R^6$ is para-fluorobenzyl.

Table L19

Table L19 provides 192 compounds of Formula L1 wherein $R_1$, D, E, $R^2$, A and J are as defined in Table L1 and $R^6$ is 2,4-dichlorophenyl.

Table L20

Table L20 provides 192 compounds of Formula L1 wherein $R^1$, D, E, $R^2$, A and J are as defined in Table L1 and $R^6$ is 2-chloro-4-trifluoromethylphenyl.

---

The following abbreviations are used throughout this description:

| | |
|---|---|
| m.p. = melting point | ppm = parts per million |
| s = singlet | br = broad |
| d = doublet | dd = doublet of doublets |
| t = triplet | q = quartet |
| m = multiplet | |

Table 1 shows selected NMR data, all with $CDCl_3$, as the solvent (unless otherwise stated; if a mixture of solvents is present, this is indicated as, for example ($CDCl_3/d_6$-DMSO)), (no attempt is made to list all characterising data in all cases) for compounds of Tables A1 to L20.

TABLE 1

| Compound No. | $^1$H NMR ($CDCl_3$ unless otherwise stated) |
|---|---|
| A3.1 | 1.0(t, 3H); 2.15(m, 2H); 2.35(s, 3H); 4.0(s, 2H); 4.7(t, 2H); 7.35(dd, 1H); 7.85(d, 1H); 7.95(d, 1H); 8.15(br, 1H). |
| A1.1 | 2.35(s, 3H); 4.0(s, 2H); 4.5(s, 3H); 7.35(dd, 1H); 7.8(d, 1H); 7.9(d, 1H); 8.05(br, 1H). |
| A18.1 | ($d_6$-DMSO): 2.35(s, 3H); 4.05(s, 2H); 5.8(s, 2H); 7.0(m, 2H); 7.4(m, 3H); 7.8(m, 2H); 10.9(br, 1H). |

TABLE 1-continued

| Compound No. | $^1$H NMR ($CDCl_3$ unless otherwise stated) |
|---|---|
| A15.1 | 2.4(s, 3H); 4.0(s, 2H); 5.3(q, 2H); 7.4(dd, 1H); 7.85(d, 1H); 7.95(d, 1H); 8.15(br, 1H). |
| A9.1 | 0.9(t, 3H); 1.35(m, 4H); 2.15(m, 2H); 2.4(s, 3H); 4.05(s, 2H); 4.7(t, 2H); 7.35(dd, 1H); 7.85(d, 1H); 7.9(d, 1H); 8.15(br, 1H). |
| A20.1 | 2.4(s, 3H); 4.05(s, 2H); 7.45(dd, 1H); 7.75(dd, 1H); 7.95(m, 3H); 8.05(m, 1H); 8.2(br, 1H). |
| A7.1 | 0.85(t, 3H); 1.7(d, 3H); 2.0–2.2(m, 2H); 2.35(s, 3H); 4.0(s, 2H); 4.9(m, 1H); 7.3(dd, 1H); 7.85(d, 1H); 7.9(d, 1H); 8.15(br, 1H). |
| A2.1 | 1.75(t, 3H); 2.35(s, 3H); 4.0(s, 2H); 4.8(q, 2H); 7.35(dd, 1H); 7.8(br, 1H); 7.9(d, 1H); 8.1(br, 1H). |
| A3.103 | 1.0(t, 3H); 1.25(t, 3H); 2.15(m, 2H); 2.85(q, 2H); 3.95(s, 2H); 4.7(t, 2H); 7.35(m, 1H); 7.85(d, 1H); 7.95(d, 1H); 7.95(br, 1H); 8.2(d, 1H); 8.3 5(d, 1H). |
| A13.1 | 1.05(s, 9H); 2.4(s, 3H); 4.05(s, 2H); 4.55(s, 2H); 7.35(dd, 1H); 7.85(br, 1H); 7.95(d, 1H); 8.15(br, 1H). |
| A3.2 | 0.95(t, 3H); 1.2(t, 3H); 2.13(m, 2H); 2.5(s, 3H); 3.65(br, 2H); 3.8(br, 2H); 4.65(t, 2H); 7.15(br.d, 1H); 7.5(br, 1H); 7.78(dd, 1H). |
| A3.6 | 0.95(t, 3H); 1.2(t, 3H); 2.1 (m, 2H); 2.5(s, 3H); 3.6(q, 2H); 3.7(br, 2H); 4.7(t, 2H); 5.1 (br, 2H); 7.15(br, 1H); 7.55(br, 1H); 7.8 (d, 1H). |
| A21.1 | 2.4(s, 3H); 4.1(s, 2H); 7.5(m, 1H); 7.8–7.9(m, 4H); 8.5(br.d, 2H); 10.35(s, 1H). |
| A16.1 | 2.39(s, 3H); 3.61 (s, 3H); 4.03(s, 2H); 5.19(t, 2H); 7.40(dd, 1H); 7.88(s, 1H); 7.97(d, 1H); 8.16(s, 1H). |
| A10.1 | 1.0(d, 6H); 2.03(q, 2H); 2.37(s, 3H); 2.37(m, 1H); 4.0(s, 2H); 4.77(dd, 2H); 7.34(dd, 1H); 7.83(s, 1H); 7.92(d, 1H); 8.16(s, 1H). |
| A6.1 | 1.0(d, 6H); 2.37(s, 3H); 2.54(septet, 1H); 4.03(s, 2H); 4.56(d, 2H); 7.36(dd, 1H); 7.84(s, 1H); 7.94(d, 1H). |
| I3.2 | 0.95(t, 3H); 1.4(t, 3H); 2.12(m, 2H); 2.5(s, 3H); 3.9(q, 2H); 4.2(s, 2H); 4.65(t, 2H); 7.42(dd, 1H); 7.8(br, 1H); 7.81 (br, 1H). |
| I3.6 | 0.95(t, 3H); 1.15(t, 3H); 2.1(m, 2H); 2.55(s, 3H); 3.5(q, 2H); 4.2(s, 2H); 4.7(t, 2H); 5.2(s, 2H); 7.4(dd, 1H); 7.8(m, 2H). |
| E1.1 | 2.35(s, 3H); 4.1 (s, 2H); 4.3(s, 3H); 7.55(m, 2H); 8.0(d, 1H); 8.3(br.s, 1H). |
| E15.1 | 2.4(s, 3H); 4.05(s, 2H); 5.25(q, 2H); 7.4(dd, 1H); 7.6(d, 1H); 8.15(d, 1H); 8.3(br, 1H). |
| F15.1 | 2.4(s, 3H); 4.1 (s, 2H); 5.25(q, 1H); 7.6(m, 2H); 8.1 (br.s, 1H); 8.25(br, 1H). |
| E22.1 | 2.40(s, 3H); 3.03(s, 3H); 4.10(s, 2H); 7.52(dd, 2H); 8.19(d, 1H); 8.2(br, 1H); 8.3(d, 1H). |
| F1.1 | 2.35(s, 3H); 4.1 (s, 2H); 4.3(s, 3H); 7.3(d, 1H); 7.55(d, 1H); 8.1 (d, 1H); 8.3(br.s, 1H). |
| F22.1 | 2.40(s, 3H); 3.03(s, 3H); 4.09(s, 2H); 7.66(dd, 2H); 8.10(d, 1H); 8.2(br, 1H); 8.34(d, 1H). |
| E6.145 | 0.94(d, 6H); 2.36(m, 1H); 2.36(s, 3H); 3.98(s, 2H); 4.22(d, 2H); 7.32(m, 1H); 7.48(m, 1H); 7.70(m, 1H); 8.02(s, 1H); 8.1 (br, 1H). |
| A6.145 | 0.96(d, 6H); 2.36(s, 3H); 2.42(m, 1H); 3.96(s, 2H); 4.24(d, 2H); 7.21 (in, 1 H); 7.64(s, 1H); 7.80(d, 1H); 7.92(s, 1H); 8.14(br, 1H). |
| E6.150 | 0.92(d, 6H); 1.14(t, 3H); 2.33(m, 1H); 2.50(s, 3H); 3.60(q, 2H); 3.72(br, 2H); 4.16(d, 2H); 5.10(br, 2H); 7.13(m, 1H); 7.37(m, 1H); 7.90(s, 1H). |
| J6.102 | 0.92(d, 6H); 1.17(t, 3H); 2.34(m, 1H); 2.56(s, 3H); 3.50(q, 2H); 4.12–4.18(m, 4H); 5.20(s, 2H); 7.32–7.44(m, 2H); 7.70(s, 1H); 7.92(s, 1H). |
| A6.150 | 0.94(d, 6H); 1.19(t, 3H); 2.38(m, 1H); 2.50(s, 3H); 3.60(q, 2H); 3.68(br, 2H); 4.18(d, 2H); 5.10(br, 2H); 7.02(m, 1H); 7.32(br, 1H); 7.62(d, 1H); 7.80(s, 1H). |
| I6.102 | 0.92(d, 6H); 1.15(t, 3H); 2.39(m, 1H); 2.54(s, 3H); 3.50(q, 2H); 4.14–4.20(m, 4H); 5.20(s, 2H); 7.32(m, 1H); 7.60–7.68(m, 2H); 7.82(s, 1H). |

The compounds of the invention may be made in a variety of ways. For example, as shown in Scheme 1, compounds (Ia) wherein Y is O and A is alkylene, alkenylene, alkylenoxy, alkylenamino or alkylenethio may be prepared by reacting amine (II) with an appropriate carboxylic ester (III) ($X^1$=alkoxy or aryloxy) or with a carboxylic acid (III, $X^1$=OH) optionally in the presence of a known coupling agent such as 1,3-dicyclohexylcarbodiimide or 1-(3-dimethylaminopropyl)-3-ethylcarbodiimide. Alternatively the carboxylic acid (III, $X^1$=OH) may first be converted to an acid chloride, anhydride or chloroformate suitable for reaction with an amine to form an amide; such procedures are well known to those skilled in the art and are described, for example in J. March, Advanced Organic Chemistry, Third Edition, John Wiley and Sons, New York, 1985, pps 370–376 and references therein.

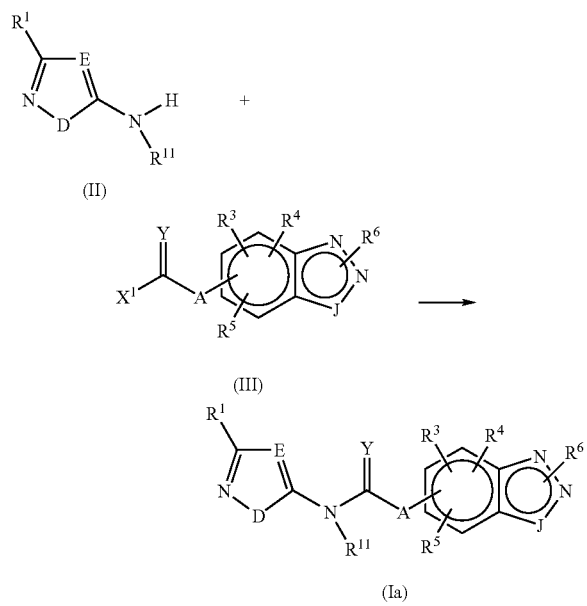

Therefore in a further aspect the invention provides a process for preparing a compound of formula (I) where Y is oxygen comprising reacting a compound of formula (II) with a compound of formula (III) where Y is oxygen and $X^1$ is a leaving group (such as alkoxy, aryloxy, OH, chloro or ClC(O)O or such that the compound of formula (III) is a dianhydride).

Compounds of formula (II) are known compounds, or may be prepared from commercially available starting materials by methods described in the literature (see, for example, C. Oliver Kappe, Robert Flammang, and Curt Wentrup, Heterocycles, Vol. 37, No. 3, 1615, (1994), A. Adams and R. Slack, J. Chem. Soc., 3061, (1959) and Ronald E Hackler, Kenneth W. Burow, Jr., Sylvester V. Kaster and David I. Wickiser, J. Heterocyclic Chem, 26, 1575, (1989), Ronald E Hackler, Glen P Jourdan, Peter L Johnson, Brian R Thoreen and Jack G Samaritoni, PCT Int. Appl., WO9304580 A1, and references therein).

The syntheses of substituted benzotriazoles and indazoles is described in the chemical literature (see, for example Alan R. Katritzky and Charles W. Rees, Comprehensive Heterocyclic Chemistry, Pergamon Press, 1984; Christoph Ruchardt and Volker Hassmann, Liebis Ann. Chem., 1980, 908; Jean-Jacques Vandenbossche and Alain Lagrange, Eur. Pat. Appl., EP904769; F. Halley and X. Sava, Synth. Commun. 1997, 27 (7), 1199; Donald R. James, Don R. Baker, Steven D. Mielich, William J. Michaely, Steven Fitzjohn, Christopher G. Knudsen, Christopher Mathews and John M. Gerdes, PCT Int. Appl., WO9318008 A1, Donald Richard James and Raymond Anthony Felix, PCT Int. Appl., WO9425446 A1) and similar methods may be used to prepare compounds of formula (III) starting from known appropriately substituted anilines. Alternatively, halobenzotriazoles and haloindazoles (especially where the halogen is bromo or iodo), which may be prepared by the above methods, may be converted into compounds of formula (III) via procedures involving transition-metal catalysed transformations analogous to those described by Nitya G. Kundu et al., Tetrahedron, 53 (39), 13397, (1997), Takao Sakamoto et al. Heterocycles, 36 (11), 2509 (1993), Motoi Kawatsura and John F. Hartwig, JACS, 1999, 121, 1473, and others.

A compound of formula (Ia), wherein Y is sulphur, may be prepared by reacting a compound of formula (Ia), wherein Y is oxygen, with a suitable thionating agent such as 2,4-bis(4-methoxyphenyl)-1,3-dithia-2,4-diphosphetane-2,4-disulfide (Lawesson's reagent), 2,4-bis(methylthio)-1,3-dithia-2,4-diphosphetane-2,4-disulfide (Davy reagent methyl), 2,4-bis(para-tolyl)-1,3-dithia-2,4-diphosphetane-2,4-disulfide (Davy reagent p-tolyl) or phosphorus pentasulfide in a suitable solvent such as toluene or fluorobenzene.

Therefore in a further aspect the invention provides a process for preparing a compound of formula (I) where Y is sulphur comprising preparing a compound of formula (I) where Y is oxygen (by reacting a compound of formula (II) with a compound of formula (III) where Y is oxygen and $X^1$ is a leaving group) and then reacting this compound with a thionating agent.

A compound of formula (IV) may be made from a compound of formula (V) by treatment with N,N-dimethylformamide dialkyl acetal in a suitable solvent such as toluene or N,N-dimethylformamide. Frequently this reaction produces a mixture of E and Z isomers which are sometimes separable by standard techniques such as flash column chromatography and recrystallisation. This invention covers isolated isomers together with mixtures of isomers.

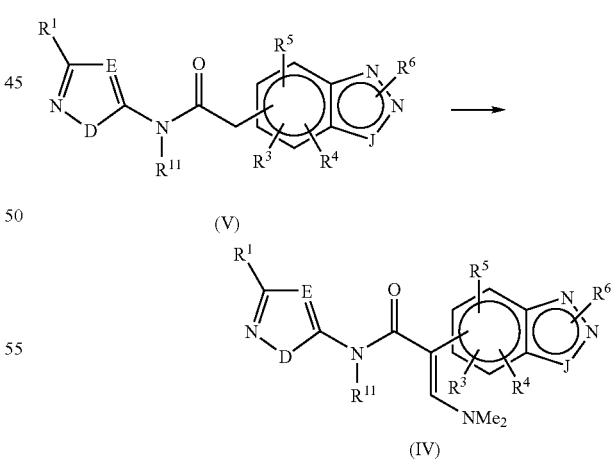

A compound of formula (IV) may be treated subsequently with an amine (HNRaRb) to give a compound of formula (VI); a compound of formula (V) may be treated in an analogous manner with a trialkylorthoformate (HC(ORd)$_3$) to afford a compound of formula (VII):

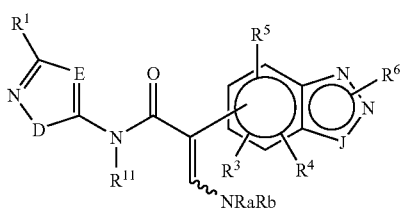

(VI)

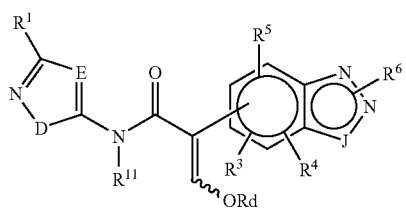

(VII)

A compound of formula (Ia), wherein $R^{11}$ is hydrogen, may be treated with an optionally substituted alkylating agent (such as an alkyl halide, chloromethylether, dialkyl sulfate or trialkyloxonium salt) optionally in the presence of a base to give an additional compound of formula (Ia) wherein $R^{11}$ is optionally substituted alkyl, which forms a further part of this invention. When Y is O, this reaction usually produces a mixture of isomeric products of formulae (Ia) and (Ib). In contrast, when Y is S, a compound of formula (Ic) is the predominant product.

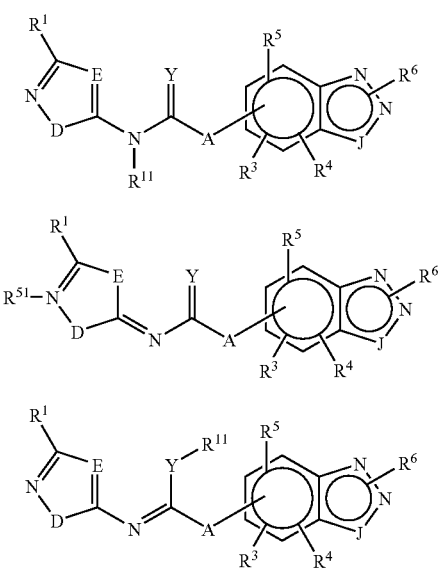

Those skilled in the art will recognise that analogous reactions involving sulfenylation, sulfonylation and acylation are possible when Y is O.

A compound of formula (Ia), where $R^{11}$ is alkoxymethyl or acyloxymethyl, may also be prepared from a compound of formula (Ia), where $R^{11}$ is hydrogen, by sequential reaction with formaldehyde and an alkylating or acylating agent.

Additional compounds of formula (Ia) may be prepared from a compound of formula (I), where $R^{11}$ is hydrogen, by reaction with hydroxymethylbenzotriazole or benzotriazoles and aldehydes according to the method of A. R. Katritzky et al., J. Org. Chem., (1993), 58, 2086.

A compound of formula (Ic) where Y=S may be reacted with an alcohol, amine, O-alkylhydroxyl-amine or hydrazine, optionally in the presence of a mercuric salt (such as mercuric chloride), according to known procedures to give a compound of formula (1d) or (Ie) respectively:

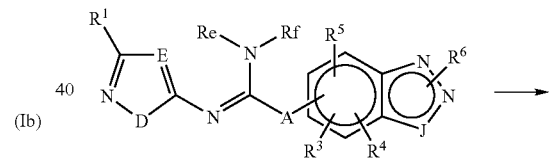

where Re is H, optionally substituted alkyl, alkenyl or alkynyl, Rf is substituted alkyl, alkenyl alkynyl, amino, substituted amino or alkoxy and Rg is optionally substituted alkyl, alkenyl or alkynyl.

A compound of formula (1d) where Re is hydrogen may be treated with an optionally substituted alkylating agent (such as an alkyl halide, chloromethylether, dialkyl sulfate or trialkyloxonium salt) optionally in the presence of a base to give a compound of formula (If).

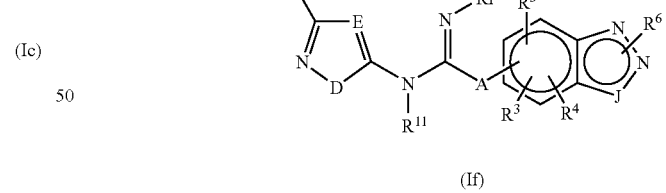

Heteroaryl N-oxides can be produced by methods known to the skilled person.

It will be appreciated that compounds of fomula (Ia), (Ib), (Ic), (Id), (Ie), (If), (IV), (V), (VI) and (VII) are all compounds of formula (I).

The compounds of formula (I) can be used to combat and control infestations of insect pests such as *Lepidoptera, Diptera, Hemiptera, Thysanoptera, Orthoptera, Dictyoptera, Coleoptera, Siphonaptera, Hymenoptera* and *Isoptera* and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (1) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus,* and *R. santonensis*) and the *Termitidae* (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp.(citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The compounds of formula (I) are also active fungicides and may be used to control one or more of the following pathogens: *Pyricularia oryzae* (*Magnaporthe grisea*) on rice and wheat and other *Pyricularia* spp. on other hosts; *Puccinia recondita, Puccinia striiformis* and other rusts on wheat, *Puccinia hordei, Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Erysiphe graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Cochliobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerella cingulata*), black rot or frogeye leaf spot (*Botryosphaeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; other downy mildews, such as *Bremia lactucae* on lettuce, *Peronospora* spp. on soybeans, tobacco, onions and other hosts, *Pseudoperonospora humuli* on hops and *Pseudoperonospora cubensis* on cucurbits; *Pythium* spp. (including *Pythium ultimum*) on turf and other hosts; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and turf and other *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp., *Typhula* spp., *Microdochium nivale, Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; post-harvest diseases particularly of fruit (for example *Penicillium digitatum, Penicillium italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodermium seditiosum*) or lumber, notably

*Cephaloascus fragrans, Ceratocystis* spp., *Ophiostoma piceae, Penicillium* spp., *Trichoderma pseudokoningii, Trichoderma viride, Trichoderma harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

A compound of formula (I) may move acropetally, basipetally or locally in plant tissue to be active against one or more fungi. Moreover, a compound of formula (I) may be volatile enough to be active in the vapour phase against one or more fungi on the plant.

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, and a method of combating and controlling fungi which comprises applying a fungicidally effective amount of a compound of formula (I), or a composition containing a compound of formula (I), to a plant, to a seed of a plant, to the locus of the plant or seed, to soil or to any other growth medium (for example a nutrient solution). The compounds of formula (I) are preferably used against insects, acarines, nematodes or fungi.

The term "plant" as used herein includes seedlings, bushes and trees. Furthermore, the fungicidal method of the invention includes protectant, curative, systemic, eradicant and antisporulant treatments.

As fungicides, the compounds of formula (I) are preferably used for agricultural, horticultural and turfgrass purposes in the form of a composition.

In order to apply a compound of formula (I) as an insecticide, acaricide, nematicide or molluscicide to a pest, a locus of pest, or to a plant susceptible to attack by a pest, or, as a fungicide to a plant, to a seed of a plant, to the locus of the plant or seed, to soil or to any other growth medium, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests or fungi such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal, molluscicidal or fungicidal composition comprising an insecticidally, acaricidally, nematicidally, molluscicidally or fungicidally effective amount of a compound of formula (I) and a suitable carrier or diluent therefor. The composition is preferably an insecticidal, acaricidal, nematicidal or fungicidal composition.

In a still further aspect the invention provides a method of combating and controlling pests or fungi at a locus which comprises treating the pests or fungi or the locus of the pests or fungi with an insecticidally, acaricidally, nematicidally, molluscicidally or fungicidally effective amount of a composition comprising a compound of formula (I). The compounds of formula (I) are preferably used against insects, acarines, nematodes or fungi.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder. Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_9$–$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium diisopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal or fungicidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (I) alone. Further the other fungicide may have a synergistic effect on the fungicidal activity of the compound of formula (I).

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr; or q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethyl-benzimidazole-1-sulphonamide, α-[N-(3-chloro-2,6-xylyl)-2-methoxy-acetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl (methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothalisopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-A1, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples.

EXAMPLE 1

This Example illustrates the preparation of N-(4-chloro-3-methylisothiazol-5-yl)-(2-propylbenzotriazol-5-yl)acetamide (Compound No. A3.1).

Step 1—Preparation of methyl 4-aminophenylacetate

4-Aminophenylacetic acid (100 g) was suspended in methanol (1000 ml) and gaseous hydrogen chloride was passed through until the mixture was saturated. The mixture was heated at 50° C. for 2 hours and was then allowed to cool to room temperature. The solvent was evaporated in vacuo and the residue was taken up in aqueous sodium bicarbonate solution and extracted with ethyl acetate. The organic extract was washed with brine, dried over anhydrous magnesium sulfate, filtered and the filtrate evaporated in vacuo to afford methyl 4-aminophenylacetate as a pale brown liquid.

$^1$H NMR (CDCl$_3$) δ ppm: 3.5(s,2H); 3.7(s,3H); 6.65(m, 2H); 7.05(m,2H).

Step 2—Preparation of methyl 4-acetamido-3-nitrophenylacetate

Methyl 4-aminophenylacetate (110 g, 0.667 mol) was added dropwise to acetic anhydride (600 ml), maintaining the temperature of the reaction mixture below 30° C. by external cooling. Once the addition was complete the mixture was cooled to below 10° C. and concentrated nitric acid (85 ml) was added dropwise. Once the addition of the acid was complete, the mixture was allowed to warm to room temperature and poured onto a mixture of ice and water. The precipitated solid was collected by filtration and dried to give methyl 4-acetamido-3-nitrophenylacetate (120 g) as a pale yellow solid.

$^1$H NMR (CDCl$_3$) δ ppm: 2.3(s,3H); 3.65(s,2H); 3.7(s, 3H); 7.55(dd,1H); 8.1(d,1H); 8.7(d,1H); 10.3(b,1H).

Step 3—Preparation of methyl
4-acetamido-3-aminophenylacetate

Methyl 4-acetamido-3-nitrophenylacetate (40 g, 0.159 mol)) was dissolved in methanol (400 ml) and hydrogenated at 5 bar over a 5% palladium on carbon catalyst. The catalyst was removed by filtration and the filtrate evaporated in vacuo to give methyl 4-acetamido-3-aminophenylacetate.

Step 4—Preparation of methyl
(benzotriazol-5-yl)acetate

Methyl 4-acetamido-3-aminophenylacetate (77 g, 0.373 mol) was taken up in a mixture of acetic acid (210 ml) and water (210 ml) and cooled to below 5° C. A solution of sodium nitrite (38.63 g, 0.559 mol) in water (200 ml) was added dropwise, and once the addition was complete the mixture was stirred for 4 hours, warming slowly to room temperature. The mixture was diluted with ethyl acetate and the insoluble material removed by filtration. The filtrate was washed with brine, dried over anhydrous magnesium sulfate, filtered and the solvent evaporated in vacuo, to give a viscous residue (51 g) which was then dissolved in a solution of methanol (400 ml) previously saturated with hydrogen chloride and the mixture stirred for 2 hours. The solvent was removed in vacuo, the residue taken up in water, neutralised with saturated aqueous sodium bicarbonate solution and extracted with ethyl acetate. The organic extract was washed with brine, dried over anhydrous magnesium sulfate, filtered and the filtrate evaporated in vacuo to afford methyl 5-benzotriazoleacetate (35 g) as a reddish liquid which crystallised on standing.

$^1$H NMR (CDCl$_3$) δ ppm: 3.7(s,3H); 3.8(s, 2H); 7.35(d, 1H); 7.8(b,2H); 13.6(b,1H).

Step 5—Preparation of methyl
(2-propylbenzotriazol-5-yl)acetate

A solution of methyl 5-benzotriazoleacetate (10 g, 0.0523 mol) in N,N-dimethylformamide was added dropwise to a chilled (ice-bath) suspension of sodium hydride (60% dispersion in oil, 2.3 g, 0.0575 mol) in N,N-dimethylformamide. When the addition was complete, the ice-bath was removed and the mixture stirred for 1 hour. N-Propyl iodide (9.78 g, 0.0575 mol) was added dropwise, and once the addition was complete the mixture was stirred at room temperature for 3 hours. The reaction mixture was poured onto ice/water, and extracted with ethyl acetate. The organic extract was washed with brine, dried over anhydrous magnesium sulfate, filtered and the filtrate evaporated in vacuo. The residue was further purified by column chromatography to afford methyl (2-propylbenzotriazol-5-yl)acetate (4.8 g).

$^1$H NMR (CDCl$_3$) δ ppm: 0.9(t,3H); 2.1(m,2H); 3.7(s, 3H); 3.8(s,2H); 4.65(t,2H); 7.3(dd,1H); 7.7(d,1H); 7.8(d, 1H).

Step 6—Preparation of
(2-propylbenzotriazol-5-yl)acetic acid

The acetate prepared in Step 5 above (4.8 g, 0.0206 mol) was dissolved in methanol (60 ml) and potassium hydroxide flakes (1.27 g, 0.0226 mol) added. The mixture was refluxed for 2 hours, then cooled and the solvent evaporated in vacuo. The residual solid was dissolved in water and extracted with diethyl ether. The aqueous solution was acidified to pH 1 by addition of dilute aqueous hydrochloric acid and extracted with ethyl acetate. The ethyl acetate extract was washed with brine, dried over anhydrous magnesium sulfate, filtered and the filtrate evaporated in vacuo to afford (2-propylbenzotriazol-5-yl)acetic acid (3.6 g) as a colourless solid.

Step 7

The acid prepared in Step 6 (0.438 g, 0.002 mol) was dissolved in dichloromethane (5 ml) and one drop of N,N-dimethyl formamide was added. Oxalyl chloride (0.307 g, 0.0022 mol) was added dropwise, and the mixture stirred at room temperature for 2 hours. The solvent was removed in vacuo, the residue taken up in xylene and added to a mixture of 5-amino-4-chloro-3-methylisothiazole (0.446 g, 0.003 mol) in xylene and heated at reflux for 2 hours. The mixture was cooled to room temperature and the solvent evaporated in vacuo. The residue was taken up in ethyl acetate, washed sequentially with saturated aqueous sodium bicarbonate solution and brine, dried over anhydrous magnesium sulfate, filtered and the filtrate evaporated in vacuo. The residue was further purified by flash column chromatography, eluting with 2:1 hexane:ethyl acetate, to give the title compound (0.34 g) as a sandy-coloured solid.

EXAMPLE 2

This Example illustrates the preparation of N-(4-chloro-3-methylisothiazol-5-yl)-N-(ethoxymethyl)-(2-propylbenzotriazol-5-yl)acetamide (Compound No. A3.6) and N-[2-ethoxymethyl-4-chloro-3-methylisothiazolin-5-ylidene]-(2-propylbenzo-triazol-5-yl)acetamide(Compound No. I3.6).

Lithium bis(trimethylsilyl)amide (1.0 M solution in tetrahydrofuran, 3.3 ml, 0.0033 mol) was added dropwise to a solution of N-(4-chloro-3-methylisothiazol-5-yl)-(2-propylbenzotriazol-5-yl)acetamide (Compound No. A3.1) (0.699 g, 0.002 mol) in tetrahydrofuran (10 ml) and once the addition was complete the mixture was stirred at room temperature for 30 minutes. Chloromethylethyl ether (0.620 g, 0.0066 mol) was added and the mixture was stirred at room temperature for 2 hours. The mixture was poured into water, neutralised, and extracted with ethyl acetate. The organic extract was dried over anhydrous magnesium sulfate, filtered and the filtrate was evaporated in vacuo. The residue was further purified by flash column chromatography, eluting initially with 2:1 hexane:ethyl acetate and then with ethyl acetate to give N-(4-chloro-3-methylisothiazol-5-yl)-N-(ethoxymethyl)-(2-propylbenzotriazol-5-yl)acetamide (0.135 g) as an orange gum and N-[2-ethoxymethyl-4-chloro-3-methylisothiazolin-5-ylidene]-(2-propylbenzotriazol-5-yl)-acetamide (0.128 g) as a colourless solid, m.p. 108–109° C.

EXAMPLE 3

This Example illustrates the preparation of N-(4-chloro-3-methylisothiazol-5-yl)-[2-(2-methylpropyl)indazol-5-yl] acetamide (Compound No. A6.145).

Step 1—Preparation of
4-bromo-2-methylacetanilide

Acetic anhydride (15.2 ml, 0.16 mol) was added dropwise to a stirred mixture of 4-bromo-2-methylaniline (10.0 g, 0.054 mol) and sodium acetate (2.52 g, 0.056 mol) in toluene (150 ml). Once the addition was complete the mixture was warmed to 85° C. and stirred for 40 minutes. The mixture was cooled to room temperature, diluted with ethyl acetate and washed with water. The organic solution was evaporated in vacuo, a further quantity of toluene was added and then the solvent was evaporated to give 4-bromo-2-methylacetanilide (12.3 g), as a colourless solid.

Step 2—Preparation of 5-bromoindazole tert-Butyl nitrite (8.34 g, 0.081 mol) was added dropwise, over 30 minutes, to a suspension of 4-bromo-2-methylacetanilide (12.3 g) in toluene (300 ml) at 65° C. and the mixture was stirred at 65° C. for 45 minutes and then at 90° C. for 3 hours. The mixture was cooled to room temperature and the solvent was removed in vacuo. The residue was purified by flash column chromatography on silica gel eluting with 2:1 diethyl ether:hexane to give 5-bromoindazole (4.12 g), as a sand-coloured solid.

$^1$H NMR (CDCl$_3$) δ: 7.27(m,1H); 7.40–7.54(m,2H); 7.94 (m,1H); 8.06(br,1H)ppm.

Step 3—Preparation of 5-bromo-1-(2-methylpropyl) indazole and 5-bromo-2-(2-methylpropyl)indazole Sodium hydride (80% suspension in oil, 0.7 g, 0.023 mol) was suspended in N,N-dimethylformamide (DMF) (10 ml) and then a solution of 5-bromoindazole (4.1 g, 0.021 mol) in DMF (40 ml) was added dropwise over 30 minutes. Once the addition was complete the mixture was stirred at ambient temperature for 75 minutes and then a solution of 1-bromo-2-methylpropane (3.7 g, 0.027 mol) in DMF (25 ml) was added over 10 minutes. The mixture was stirred for 5 hours and was then allowed to stand at ambient temperature overnight. The mixture was poured into water, extracted with diethyl ether and then the organic extract was washed further with water, dried over anhydrous magnesium sulfate, filtered and the filtrate was evaporated in vacuo. The residue was purified by flash column chromatography on silica gel eluting with 1:1 diethyl ether:hexane to give 5-bromo-1-(2-methylpropyl)indazole (2.67 g) and 5-bromo-2-(2-methylpropyl)indazole (1.49 g), each as an orange oil.

5-Bromo-1-(2-methylpropyl)indazole:

$^1$H NMR (CDCl$_3$) δ: 0.92(d,6H); 2.32(m,1H); 4.16(d, 2H); 7.28(m,1H); 7.44(m,1H); 7.86(m,1H); 7.92(s,1H)ppm.

5-Bromo-2-(2-methylpropyl)indazole:

$^1$H NMR (CDCl$_3$) δ: 0.94(d,6H); 2.38(m,1H); 4.18(d, 2H); 7.32(m,1H); 7.58(m,1H); 7.82(m,2H)ppm.

Step 4—Preparation of ethyl [2-(2-methylpropyl)indazol-5-yl]acetate

5-Bromo-2-(2-methylpropyl)indazole (1.41 g, 0.0056 mol) and palladium acetate (0.063 g, 0.00028 mol) were stirred in toluene (10 ml) under an atmosphere of nitrogen. Ethyl trimethylsilylacetate (2.35 ml, 0.0115 mol), potassium tert-butoxide (0.66 g, 0.059 mol) and a 10% w/v solution of tri-tert-butylphosphine in toluene (0.97 ml, 0.00048 mol) were added sequentially and then the mixture was heated to 90° C. for 105 minutes. The mixture was cooled to room temperature, diluted with diethyl ether and filtered through diatomaceous earth and the filtrate was evaporated in vacuo. The residue was purified by flash column chromatography on silica gel eluting with 2:1 diethyl ether:hexane to give ethyl[2-(2-methylpropyl)indazol-5-yl]acetate (1.85 g), as a yellow oil.

$^1$H NMR (CDCl$_3$) δ: 0.96(d,6H); 1.27(t,3H); 2.39(m,1H); 3.68(s,2H); 4.12–4.22(m,4H); 7.22(m,1H); 7.54(m,1H); 7.68(m,1H); 7.84(s,1H) ppm.

Step 5—Preparation of N-(4-chloro-3-methyl-isothiazol-5-yl)-[2-(2-methylpropyl)indazol-5-yl] acetamide Sodium methoxide (0.42 g, 0.0078 mol) was added to a solution of 5-amino-4-chloro-3-methylisothiazole (0.46 g, 0.0031 mol) in tetrahydrofuran (THF) (15 ml) and the mixture was stirred at ambient temperature for 15 minutes. A solution of ethyl[2-(2-methylpropyl)indazol-5-yl]acetate (0.80 g, 0.0031 mol) in THF was added dropwise and, once the addition was complete, the mixture was stirred at ambient temperature for 3 hours. The mixture was partitioned between ethyl acetate and saturated aqueous ammonium chloride solution and then the organic extract was dried over anhydrous magnesium sulfate, filtered and the filtrate was evaporated in vacuo. The residue was triturated with diethyl ether to give N-(4-chloro-3-methylisothiazol-5-yl)-[2-(2-methylpropyl)indazol-5-yl]acetamide (0.78 g) as a pale-brown solid (m.p. 133–135° C.).

EXAMPLE 4

This Example illustrates the preparation of N-(4-chloro-3-methylisothiazol-5-yl)-N-(ethoxymethyl)-[2-(2-methylpropyl)indazol-5-yl]acetamide (Compound No. A6.150) and N-[2-ethoxymethyl-4-chloro-3-methylisothiazolin-5-ylidene]-[2-(2-methylpropyl)indazol-5-yl) acetamide (Compound No. I6.102).

N-(4-chloro-3-methylisothiazol-5-yl)-[2-(2-methylpropyl)indazol-5-yl]acetamide (0.50 g, 0.0014 mol) was dissolved in dichloromethane (15 ml) and the solution was cooled to 5° C. Chloromethyl ethyl ether (0.32 ml, 0.0035 mol), 50% aqueous sodium hydroxide solution (0.56 ml) and benzyltriethylammonium chloride (0.018 g) were added sequentially and then the mixture was stirred for 2 hours. The mixture was diluted with dichloromethane, washed with water, dried over anhydrous magnesium sulfate, filtered and the filtrate was evaporated in vacuo. The residue was purified by flash column chromatography on silica gel, initially eluting with 3:1 diethyl ether:hexane, then with diethyl ether and finally with ethyl acetate to give N-(4-chloro-3-methylisothiazol-5-yl)-N-(ethoxymethyl)-[2-(2-methylpropyl)indazol-5-yl]acetamide (0.16 g) as a yellow oil and N-[2-ethoxymethyl-4-chloro-3-methylisothiazolin-5-ylidene]-[2-(2-methylpropyl)indazol-5-yl) acetamide (0.20 g) as a cream-coloured solid (m.p. 105–106° C.).

EXAMPLE 5

This Example illustrates the pesticidal/insecticidal properties of compounds of formula (I). The activities of samples of individual compounds of formula (I) or of mixtures of compounds of formula (I) were determined using a variety of pests. The pests were treated with a liquid composition containing 500 parts per million (ppm) by weight of a compound. Each composition was made by dissolving the compound in an acetone and ethanol (50:50 by volume) mixture and diluting the solution with water containing 0.05% by volume of a wetting agent, SYNPERONIC NP8, until the liquid composition contained the required concentration of the compound.

Samples used were as shown in Table 2.

TABLE 2

| Sample No. | Component A (Compound No.) | Component B (Compound No.) | Molar Ratio A:B |
|---|---|---|---|
| 1 | A3.1 | | |
| 2 | A1.1 | | |
| 3 | F1.1 | E1.1 | 1:3 |
| 4 | A18.1 | | |
| 5 | E18.1 | F18.1 | 1:1 |
| 6 | F15.1 | E15.1 | 8:92 |
| 7 | F15.1 | E15.1 | 1:2 |
| 8 | A15.1 | | |
| 9 | A9.1 | | |
| 10 | E9.1 | F9.1 | 1:1 |
| 11 | A20.1 | | |
| 12 | E20.1 | F20.1 | 1:1 |
| 13 | A7.1 | | |
| 14 | E7.1 | F7.1 | 1:1 |
| 15 | A2.1 | | |
| 16 | E2.1 | F2.1 | 1:1 |
| 17 | A13.1 | | |
| 18 | E13.1 | F13.1 | 3:2 |
| 19 | A3.2 | | |
| 20 | A3.6 | | |
| 21 | A21.1 | | |
| 22 | F21.1 | | |
| 23 | E21.1 | F21.1 | 1:1 |
| 24 | E3.1 | F3.1 | 1:1 |
| 25 | E21.1 | F21.1 | 9:1 |
| 26 | F21.1 | | |
| 27 | E22.1 | | |
| 29 | A16.1 | | |
| 30 | A10.1 | | |
| 31 | A6.1 | | |
| 32 | A3.103 | | |
| 33 | I3.2 | | |
| 34 | I3.6 | | |
| 35 | E6.145 | | |
| 36 | A6.145 | | |
| 37 | E6.150 | | |
| 38 | J6.102 | | |
| 39 | A6.150 | | |
| 40 | I6.102 | | |

The test procedure adopted with regard to each pest, was essentially the same and comprised supporting a number of the pests on a medium which was usually a substrate, a host plant or a foodstuff on which the pests feed, and treating either or both the medium and the pests with a composition. Pest mortality was assessed usually between two and five days after treatment.

The results of the tests against peach aphid (*Myzus persicae*) are presented below. In this test Chinese cabbage leaves were infested with aphids, the infested leaves were sprayed with the test composition, and the mortality assessed after three days. The results indicate a grading of mortality (score) designated as 9, 5 or 0 wherein 9 indicates 80–100% mortality, 5 indicates 40–79% mortality and 0 indicates less than 40% mortality.

Sample Nos. 2, 13, 15, 19, 20, 30, 31, 32, 36, 37, 39 and 40 each gave a mortality score of 9 whilst Sample Nos. 8, 9, 11, 17, 29, 34, 35 and 38 each gave a score of 5.

In addition, in a similar test against two-spotted spider mites (*Tetranychus urticae*) Sample Nos. 1, 8, 11, 12, 13, 17, 18, 19, 20 and 30 each gave a mortality score of 9 whilst Sample No. 9 gave a score of 5.

EXAMPLE 6

This Example illustrates the fungicidal properties of compounds of formula (I). The compounds were tested against a variety of foliar fungal diseases of plants. The technique employed was as follows.

Plants were grown in John Innes Potting Compost (No. 1 or 2) in 4 cm diameter, 3.5 cm depth minipots. The test samples were individually formulated as a solution either in acetone or acetone/ethanol (1:1 by volume) which was diluted in deionised water to a concentration of 100 ppm (that is, 1 mg of compound in a final volume of 10 ml) immediately before use. When foliar sprays were applied to monocotyledonous crops, TWEEN 20 (0.1% by volume) was added. TWEEN is a registered trade mark.

Individual compounds of formula (I), or mixtures of compounds of formula (1), were applied as a foliar (Folr) application (where the chemical solution was applied to the foliage of the test plants by spraying the plant to maximum droplet retention.)

These tests were carried out against *Uncinula necator* (UNCINE), on vines; *Phytophthora infestans lycopersici* (PHYTIN) on tomatoes; *Puccinia recondita* (PUCCRT), on wheat; and *Pyricularia oryzae* (PYRIOR) on rice. Each treatment was applied to two or more replicate plants for *Phytophthora infestans lycopersici* and *Uncinula necator*. For tests on *Puccinia recondita* and *Pyricularia oryzae* two replicate pots each containing 6 to 10 plants were used for each treatment. The plants were inoculated one day before (Erad) or one day after (Prot) chemical application. The *Phytophthora infestans lycopersici, Puccinia recondita* and *Pyricularia oryzae* plants were inoculated with a calibrated fungal spore suspension. The *Uncinula necator* plants were inoculated using a 'blowing' inoculation technique.

After chemical application and inoculation, the plants were incubated under high humidity conditions and then put into an appropriate environment to allow infection to proceed, until the disease was ready for assessment. The time period between chemical application and assessment varied from five to fourteen days according to the disease and environment. However, each individual disease was assessed after the same time period for all samples.

Assessments were performed on each of two leaves on each of the replicate plants for *Phytophthora infestans lycopersici*. Assessments were performed on a single leaf of each of the replicate plants for *Uncinula necator*. For *Puccinia recondita* and *Pyricularia recondita* assessments were carried out collectively on the plants in each replicate pot.

The disease level present (that is, the percentage leaf area covered by actively sporulating disease) was assessed visually. For each treatment, the assessed values for all its replicates were meaned to provide mean disease values. Untreated control plants were assessed in the same manner. The data were then processed by the method, described hereinafter, to provide PRCO (Percentage Reduction from Control) values.

An example of a typical calculation is as follows:
Mean disease level for treatment A=25%
Mean disease level on untreated controls=85%

$$PRCO = 100 - \frac{\{\text{Mean disease level for treatment } A\}}{\{\text{Mean disease level on untreated controls}\}} \times 100$$

$$= 100 - \left(\frac{25}{85} \times 100\right) = 70.6$$

The PRCO is then rounded to the nearest whole number; therefore, in this particular example, the PRCO result is 71.

It is possible for negative PRCO values to be obtained.

PRCO results are shown below in Table 3, where the Sample Nos. are as defined in Example 5.

TABLE 3

| Sample No. | PHYTIN Prot | PUCCRT Prot | PYRIOR Prot | UNCINE Erad |
|---|---|---|---|---|
| 1 | 100 | 100 | 100 | |
| 2 | | | 87 | |
| 3 | | | 40 | |
| 4 | | | 92 | |
| 6 | 75 | 16 | 6 | 11 |
| 7 | | | 96 | |
| 8 | | | 100 | |
| 9 | 100 | 99 | 100 | |
| 11 | | | 100 | |
| 12 | | | 98 | |
| 19 | 81 | 87 | | |
| 30 | 100 | 100 | | 100 |
| 31 | 100 | 100 | | 100 |
| 33 | 30 | 36 | | |
| 34 | 81 | | 93 | 100 |

The invention claimed is:
1. A compound of formula (I):

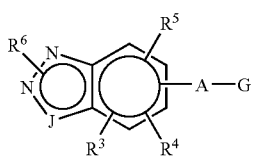

wherein G is either

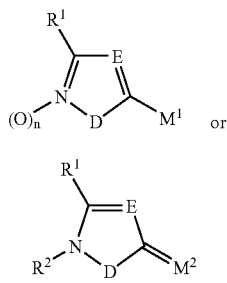

where $M^1$ or $M^2$ is bonded to A; n is 0 or 1; A is optionally substituted $C_{1-6}$ alkylene, optionally substituted $C_{2-6}$ alkenylene, optionally substituted $C_{2-6}$ alkynylene, optionally substituted $C_{1-6}$ alkylenoxy, optionally substituted oxy($C_{1-6}$)alkylene, optionally substituted $C_{1-6}$ alkylenethio, optionally substituted thio($C_{1-6}$)alkylene, optionally substituted $C_{1-6}$ alkylenamino, optionally substituted amino($C_{1-6}$)alkylene, optionally substituted [$C_{1-6}$ alkyleneoxy($C_{1-6}$)alkylene], optionally substituted —[$C_{1-6}$ alkylenethio($C_{1-6}$)alkylene], optionally substituted [$C_{1-6}$ alkylenesulfinyl-($C_{1-6}$)alkylene], optionally substituted [$C_{1-6}$ alkylenesulfonyl($C_{1-6}$)alkylene] or optionally substituted [$C_{1-6}$ alkyleneamino($C_{1-6}$)alkylene]; when G is (i), D is S, $NR^7$, $CR^8$=$CR^9$, $CR^8$=N, $CR^8$=N(O), N=$CR^9$ or N(O)=$CR^9$; when G is (ii), D is S or $NR^7$; E is N, N-oxide or $CR^{10}$; $M^1$ is OC(=Y), N($R^{11}$)C(=Y), N=C($OR^{12}$), N=C($SR^{13}$) or N=C($NR^{14}R^{15}$) where O or N is the atom of attachment to the ring containing D and E; $M^2$ is N—C(=Y) where N is the atom of attachment to the ring containing D and E; Y is O, S or $NR^{16}$; J is N or $CR^{17}$; $R^1$ is hydrogen, halogen, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ alkylthio, optionally substituted $C_{3-7}$ cycloalkyl, cyano, nitro or $SF_5$; $R^2$ is optionally substituted $C_{1-10}$ alkyl, optionally substituted [$C_{2-6}$ alkenyl($C_{1-6}$)alkyl], optionally substituted [$C_{2-6}$ alkynyl-($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$)alkylaminocarbonyl, optionally substituted phenoxycarbonyl, optionally substituted $C_{1-6}$ alkylthio, optionally substituted $C_{1-6}$ alkylsulfinyl, optionally substituted $C_{1-6}$ alkylsulfonyl, optionally substituted arylthio, optionally substituted arylsulfinyl, optionally substituted arylsulfonyl or $R^{18}R^{19}NS$; $R^3$, $R^4$ and $R^5$ are, independently, hydrogen, halogen, optionally substituted $C_{1-6}$ alkyl, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, cyano, nitro, optionally substituted $C_{1-6}$ alkylcarbonyl, optionally substituted $C_{1-6}$ alkoxycarbonyl or $SF_5$; $R^6$ is hydrogen, cyano, optionally substituted $C_{1-20}$ alkyl, optionally substituted substituted $C_{2-20}$ alkenyl($C_{1-6}$)alkyl, optionally substituted $C_{2-20}$ alkynyl ($C_{1-6}$)alkyl, optionally substituted $C_{3-7}$ cycloalkyl, optionally substituted $C_{5-6}$ cycloalkenyl, formyl, optionally substituted $C_{1-20}$ alkoxycarbonyl, optionally substituted $C_{1-20}$ alkylcarbonyl, aminocarbonyl, optionally substituted $C_{1-20}$ alkylaminocarbonyl, optionally substituted di($C_{1-20}$)alkylaminocarbonyl, optionally substituted aryloxycarbonyl, optionally substituted arylcarbonyl, optionally substituted arylaminocarbonyl, optionally substituted N-alkyl-N-arylaminocarbonyl, optionally substituted diarylaminocarbonyl, optionally substituted heteroaryloxycarbonyl, optionally substituted heteroarylcarbonyl, optionally substituted heteroarylaminocarbonyl, optionally substituted alkylheteroarylaminocarbonyl, optionally substituted diheteroarylaminocarbonyl, optionally substituted phenyl, optionally substituted heteroaryl, optionally substituted heterocyclyl, optionally substituted $C_{1-20}$ alkylsulfonyl or optionally substituted arylsulfonyl; $R^7$ is $C_{1-6}$ alkyl; $R^8$ and $R^9$ are, independently, hydrogen, halogen, cyano, nitro, optionally substituted $C_{1-6}$ alkyl, optionally substituted $C_{2-6}$ alkenyl, optionally substituted $C_{2-6}$ alkynyl or optionally substituted $C_{1-6}$ alkoxy; $R^{10}$ is hydrogen, halogen, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ alkylthio, optionally substituted —$C_{1-6}$ alkylsulfinyl, optionally substituted $C_{1-6}$ alkylsulfonyl, cyano, nitro, formyl, $R^{20}ON$=C($R^{21}$), optionally substituted $C_{1-6}$ alkylcarbonyl, optionally substituted $C_{1-6}$ alkoxycarbonyl or $SF_5$; or $R^1$ and $R^{10}$ together with the atoms to which they are attached may be joined to form a five, six or seven-membered saturated or unsaturated ring carbocylic or heterocyclic ring which may contain one or two hetero atoms selected from O, N or S and which may be optionally substituted by $C_{1-6}$ alkyl, $C_{1-6}$ haloalkyl or halogen; $R^{11}$ is hydrogen, optionally substituted $C_{1-10}$ alkyl, optionally substituted [$C_{2-6}$ alkenyl($C_{1-6}$)alkyl], optionally substituted [$C_{2-6}$ alkynyl-($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$)alkylamino-carbonyl, optionally substituted phenoxycarbonyl, optionally substituted $C_{1-6}$ alkylthio, optionally substituted $C_{1-6}$ alkylsulfinyl, optionally substituted $C_{1-6}$ alkylsulfonyl, optionally substituted arylthio, optionally substituted arylsulfinyl, optionally substituted arylsulfonyl or $R^{22}R^{23}NS$; $R^{12}$ is optionally substituted C$_{1-10}$ alkyl, optionally substituted [C$_{2-6}$ alkenyl(C$_{1-6}$)alkyl], optionally substituted [C$_{2-6}$ alkynyl(C$_{1-6}$)alkyl], optionally substituted C$_{3-7}$ cycloalkyl, optionally substituted C$_{1-10}$ alkylcarbonyl, optionally substituted C$_{1-10}$ alkoxycarbonyl, formyl, optionally substituted C$_{1-10}$ alkylaminocarbonyl, optionally substituted di(C$_{1-10}$)alkylamino-carbonyl, amino, optionally substituted C$_{1-6}$ alkylamino, optionally substituted di-(C$_{1-6}$)alkylamino, optionally substituted phenoxycarbonyl, tri(C$_{1-4}$)alkylsilyl, aryldi(C$_{1-4}$)alkylsilyl, (C$_{1-4}$)alkyldiarylsilyl or triarylsilyl; R$^{13}$ is optionally substituted C$_{1-10}$ alkyl, optionally substituted [C$_{2-6}$ alkenyl(C$_{1-6}$)alkyl], optionally substituted [C$_{2-6}$ alkynyl(C$_{1-6}$)alkyl], optionally substituted C$_{3-7}$ cycloalkyl, optionally substituted C$_{1-10}$ alkylcarbonyl, optionally substituted C$_{1-10}$ alkoxycarbonyl, optionally substituted C$_{1-10}$ alkylaminocarbonyl, optionally substituted di(C$_{1-10}$)alkylaminocarbonyl or optionally substituted phenoxycarbonyl); R$^{14}$ and R$^{15}$ are, independently optionally substituted C$_{1-10}$ alkyl, optionally substituted C$_{1-6}$ alkoxy, optionally substituted [C$_{2-6}$ alkenyl-(C$_{1-6}$)alkyl], optionally substituted [C$_{2-6}$ alkynyl(C$_{1-6}$)alkyl], optionally substituted C$_{3-7}$ cycloalkyl, optionally substituted C$_{1-10}$ alkylcarbonyl, optionally substituted C$_{1-10}$ alkoxycarbonyl, formyl, optionally substituted C$_{1-10}$ alkylaminocarbonyl, optionally substituted di(C$_{1-10}$)alkylaminocarbonyl, hydroxy, amino, optionally substituted C$_{1-6}$ alkylamino, optionally substituted di(C$_{1-6}$)alkylamino, or optionally substituted phenoxycarbonyl; R$^{16}$ is hydrogen, cyano, nitro, optionally substituted C$_{1-6}$ alkyl, optionally substituted C$_{3-7}$ cycloalkyl, optionally substituted (C$_{2-6}$)alkenyl(C$_{1-6}$)alkyl, optionally substituted (C$_{2-6}$)alkynyl(C$_{1-6}$)alkyl, optionally substituted phenyl, optionally substituted heteroaryl, optionally substituted C$_{1-6}$ alkylcarbonyl, optionally substituted C$_{1-6}$ alkoxycarbonyl, optionally substituted C$_{1-6}$ alkylamino, optionally substituted di(C$_{1-6}$)alkylamino, optionally substituted C$_{1-6}$ alkylcarbonylamino, optionally substituted C$_{1-6}$ alkoxycarbonylamino, optionally substituted C$_{1-6}$ alkoxy, optionally substituted C$_{1-6}$ alkylthio, optionally substituted C$_{1-6}$ alkylsulfinyl, optionally substituted C$_{1-6}$ alkylsulfonyl, optionally substituted arylthio, optionally substituted arylsulfinyl, optionally substituted arylsulfonyl or C$_{1-6}$ acyloxy; R$^{17}$ is hydrogen, halogen, nitro, cyano, optionally substituted C$_{1-8}$ alkyl, optionally substituted C$_{2-6}$ alkenyl, optionally substituted C$_{2-6}$ alkynyl, optionally substituted C$_{3-7}$ cycloalkyl, optionally substituted C$_{1-6}$ alkoxycarbonyl, optionally substituted C$_{1-6}$ alkylcarbonyl, optionally substituted C$_{1-6}$ alkylaminocarbonyl, optionally substituted di(C$_{1-6}$)alkylaminocarbonyl, optionally substituted phenyl or optionally substituted heteroaryl; R$^{18}$ and R$^{19}$ are, independently, optionally substituted C$_{1-6}$ alkyl or R$^{18}$ and R$^{19}$ together with the N atom to which they are attached form a five, six or seven-membered heterocyclic ring which may contain one or two further hetero atoms selected from O, N or S and which may be optionally substituted by one or two C$_{1-6}$ alkyl groups; R$^{20}$ is hydrogen, optionally substituted phenyl, optionally substituted phenyl (C$_{1-4}$)alkyl or optionally substituted C$_{1-20}$ alkyl; R$^{21}$ is hydrogen, optionally substituted phenyl or optionally substituted C$_{1-6}$ alkyl; and R$^{22}$ and R$^{23}$ are, independently, optionally substituted C$_{1-6}$ alkyl or R$^{22}$ and R$^{23}$ together with the N atom to which they are attached form a five, six or seven-membered heterocyclic ring which may contain one or two further hetero atoms selected from O, N or S and which may be optionally substituted by one or two C$_{1-6}$ alkyl groups.

2. A compound as claimed in claim 1 of formula (IA):

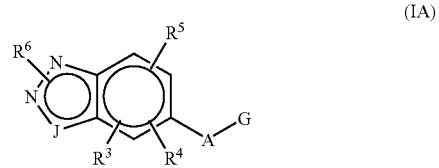

(IA)

wherein A, G, J, R$^3$, R$^4$, R$^5$ and R$^6$ are as claimed in claim 1.

3. A compound of formula (I) as claimed in claim 1 or a compound of formula (IA) as claimed in claim 2 wherein, when G is (i) as defined in claim 1, D is S or CR$^8$═CR$^9$, where R$^8$ and R$^9$ are, independently, hydrogen, halogen, C$_{1-6}$ alkyl, C$_{1-6}$ haloalkyl C$_{2-6}$ alkenyl, C$_{1-6}$ alkynyl, C$_{1-6}$ alkoxy or C$_{1-6}$ haloalkoxy; when G is (ii) as defined in claim 1, D is S; E is N or CR$^{10}$ where R$^{10}$ is hydrogen, halogen, C$_{1-6}$ alkyl, C$_{1-6}$ haloalkyl, —C$_{1-6}$ alkoxy, C$_{1-6}$ haloalkoxy, C$_{1-6}$ alkoxy (C$_{1-6}$)alkyl, C$_{1-6}$ alkylthio or SF$_5$; or R$^1$ and R$^{10}$ together with the atoms to which they are attached form a benzene ring optionally substituted by C$_{1-6}$ alkyl, C$_{1-6}$ haloalkyl or halogen; and M$^1$ is N(R$^{11}$)C(═O) where R$^{11}$ is hydrogen, C$_{1-6}$ alkyl, C$_{1-6}$ alkoxy(C$_{1-6}$)alkyl, benzyloxymethyl or benzoyloxymethyl.

4. A compound of formula (I) as claimed in claim 1 or a compound of formula (IA) as claimed in claim 2 wherein A is C$_{1-4}$ alkylene, —C(O)— or C$_{1-4}$ alkyleneoxy.

5. A compound of formula (I) as claimed in claim 1 or a compound of formula (IA) as claimed in claim 2 wherein G is (i) as defined in claim 1 and n is 0.

6. A compound of formula (I) as claimed in claim 1 or a compound of formula (IA) as claimed in claim 2 wherein R$^3$, R$^4$ and R$^5$ are, independently, hydrogen, C$_{1-3}$ alkyl or halogen.

7. A compound of formula (I) as claimed in claim 1 or a compound of formula (IA) as claimed in claim 2 wherein R$^6$ is C$_{1-10}$ alkyl or C$_{1-10}$ haloalkyl (each one of which may be substituted with a C$_{1-6}$ alkyloxime, C$_{1-6}$ haloalkyloxime, C$_{1-6}$ alkylhydrazone or C$_{1-6}$ haloalkylhydrazone group) or C$_{1-6}$ cyanoalkyl, C$_{2-6}$ alkenyl(C$_{1-6}$)alkyl, C$_{2-6}$ alkynyl(C$_{1-6}$)alkyl, C$_{3-7}$ cycloalkyl, C$_{3-7}$ halocycloalkyl, C$_{3-7}$ cyanocycloalkyl, C$_{1-3}$ alkyl(C$_{3-7}$)cycloalkyl, C$_{1-3}$ alkyl(C$_{3-7}$)halocycloalkyl, C$_{5-6}$ cycloalkenyl, C$_{3-7}$ cycloalkyl(C$_{1-6}$)alkyl, C$_{5-6}$ cycloalkenyl(C$_{1-6}$)alkyl, C$_{2-6}$ haloalkenyl(C$_{1-6}$)alkyl, C$_{1-6}$ cyanoalkenyl(C$_{1-6}$)alkyl, C$_{1-6}$ alkoxy(C$_{1-6}$)alkyl, C$_{3-6}$ alkenyloxy(C$_{1-6}$)alkyl, C$_{3-6}$ alkynyloxy(C$_{1-6}$)alkyl, aryloxy (C$_{1-6}$)alkyl, C$_{1-6}$ carboxyalkyl, C$_{1-6}$ alkylcarbonyl(C$_{1-6}$)alkyl, C$_{2-6}$ alkenylcarbonyl(C$_{1-6}$)alkyl, C$_{2-6}$ alkynylcarbonyl(C$_{1-6}$)alkyl, C$_{1-6}$ alkoxycarbonyl(C$_{1-6}$)alkyl, C$_{3-6}$ alkenyloxycarbonyl(C$_{1-6}$)alkyl, C$_{3-6}$ alkynyloxycarbonyl(C$_{1-6}$)alkyl, aryloxycarbonyl(C$_{1-6}$)alkyl, C$_{1-6}$ alkylthio(C$_{1-6}$)alkyl, C$_{1-6}$ alkylsulfinyl(C$_{1-6}$)alkyl, C$_{1-6}$ alkylsulfonyl(C$_{1-6}$)alkyl, aminocarbonyl(C$_{1-6}$)alkyl, aminocarbonyl(C$_{2-6}$)alkenyl, aminocarbonyl(C$_{2-6}$)alkynyl, C$_{1-6}$ alkylaminocarbonyl(C$_{1-6}$)alkyl, di(C$_{1-6}$)alkylaminocarbonyl(C$_{1-6}$)alkyl, C$_{1-6}$ alkylaminocarbonyl(C$_{1-6}$)alkenyl(C$_{1-6}$)alkyl, di-(C$_{1-6}$)alkylaminocarbonyl(C$_{1-6}$)alkenyl(C$_{1-6}$)alkyl, alkylaminocarbonyl(C$_{1-6}$)alkynyl-(C$_{1-6}$)alkyl, di(C$_{1-6}$)alkylaminocarbonyl(C$_{1-6}$)alkynyl(C$_{1-6}$)alkyl, phenyl (optionally substituted by halo, nitro, cyano, C$_{1-6}$ alkyl, C$_{1-6}$ haloalkyl, C$_{1-6}$ alkoxy or C$_{1-6}$ haloalkoxy), phenyl(C$_{1-4}$)alkyl (wherein the phenyl group is optionally substituted by halo, nitro, cyano, C$_{1-6}$ alkyl, C$_{1-6}$ haloalkyl, C$_{1-6}$ alkoxy or C$_{1-6}$ haloalkoxy), phenyl(C$_{2-4}$)alkenyl(C$_{1-6}$)alkyl, (wherein the phenyl group is optionally substituted by halo, nitro, cyano, $C_{1-6}$ alkyl, $C_{1-6}$ haloalkyl, $C_{1-6}$ alkoxy, $C_{1-6}$ alkylsulfonyl or $C_{1-6}$ haloalkoxy), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl($C_{1-4}$) alkyl (wherein the heteroaryl group is optionally substituted by halo, nitro, cyano, $C_{1-6}$ alkyl, $C_{1-6}$ haloalkyl, $C_{1-6}$ alkoxy, $C_{1-6}$ alkylsulfonyl or $C_{1-6}$ haloalkoxy)or heterocyclyl($C_{1-4}$) alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy).

8. A compound of formula (I) as claimed in claim 1 or a compound of formula (IA) as claimed in claim 2 wherein J is N or $CR^{17}$ where $R^{17}$ is hydrogen, $C_{1-6}$ alkyl, $C_{1-6}$ haloalkyl, cyano, halogen or nitro.

9. A process for preparing a compound of formula (I) as claimed in claim 1 comprising (a) where Y is oxygen, reacting a compound of formula (II)

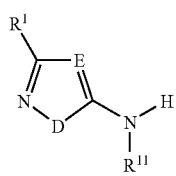

where D, E, $R^1$ and $R^{11}$ are as defined in claim 1 with a compound of formula (III)

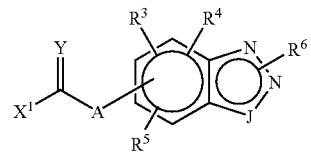

where Y is oxygen, $X^1$ is a leaving group and A, J, $R^3$, $R^4$, $R^5$ and $R^6$ are as defined in claim 1; or (b) where Y is sulphur, preparing a compound of formula (I) as claimed in claim 1 where Y is oxygen using the method described in (a) and then reacting this compound with a thionating agent.

10. A fungicidal, insecticidal, acaricidal, molluscicidal or nematicidal composition comprising a fungicidally, insecticidally, acaricidally, molluscicidally or nematicidally effective amount of a compound of formula (I) as claimed in claim 1 and a carrier or diluent therefor.

11. A method of combating and controlling fungi comprising applying to a plant, to a seed of a plant, to the locus of the plant or seed or to the soil a fungicidally effective amount of either a compound of formula (I) as claimed in claim 1.

12. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of either a compound of formula (I) as claimed in claim 1.

* * * * *